(12) United States Patent
Grieb et al.

(10) Patent No.: US 6,696,060 B2
(45) Date of Patent: Feb. 24, 2004

(54) METHODS FOR STERILIZING PREPARATIONS OF MONOCLONAL IMMUNOGLOBULINS

(75) Inventors: Teri Grieb, Damascus, MD (US); Wilson H. Burgess, Clifton, VA (US); William N. Drohan, Springfield, VA (US); Ren-Yo Forng, Potomac, MD (US); Martin J. MacPhee, Montgomery Village, MD (US); David M. Mann, Gaithersburg, MD (US); Anna McBain, Derwood, MD (US)

(73) Assignee: Clearant, Inc., Los Angeles, CA (US)

( * ) Notice: Subject to any disclaimer, the term of this patent is extended or adjusted under 35 U.S.C. 154(b) by 0 days.

(21) Appl. No.: 09/880,052

(22) Filed: Jun. 14, 2001

(65) Prior Publication Data

US 2003/0012779 A1 Jan. 16, 2003

(51) Int. Cl.⁷ .................. A61K 39/395; C07K 16/00
(52) U.S. Cl. .................. 424/176.1; 422/21; 422/22; 422/23; 436/548; 530/390.1
(58) Field of Search .................. 422/21–23; 424/176.1; 436/548; 530/390.1

(56) References Cited

U.S. PATENT DOCUMENTS

| | | |
|---|---|---|
| RE23,195 E | 2/1950 | Brasch |
| 2,832,689 A | 4/1958 | Procter et al. |
| 2,920,969 A | 1/1960 | Stoddard |
| 2,962,380 A | 11/1960 | Wertheim |
| 3,620,944 A | 11/1971 | Tanito .................. 204/158 |
| 3,743,480 A | 7/1973 | Falk |
| 3,779,706 A | 12/1973 | Nablo |
| 4,136,094 A | 1/1979 | Condie .................. 530/390.1 |
| 4,251,437 A | 2/1981 | Rasmussen et al. |
| 4,282,863 A | 8/1981 | Beigler et al. |
| 4,330,626 A | 5/1982 | Blair et al. .................. 435/173 |
| 4,336,247 A | 6/1982 | Eriksen |
| 4,370,264 A | 1/1983 | Kotitschke et al. |
| 4,409,105 A | 10/1983 | Hayashi et al. .................. 210/679 |
| 4,472,840 A | 9/1984 | Jefferies |
| 4,620,908 A * | 11/1986 | Van Duzer .................. 204/157.68 |
| 4,727,027 A | 2/1988 | Wiesehahn et al. .................. 435/173 |
| 4,784,850 A | 11/1988 | Abraham .................. 424/87 |
| 4,798,611 A | 1/1989 | Freeman, Jr. .................. 623/66 |
| 4,865,602 A | 9/1989 | Smestad et al. .................. 623/16 |
| 4,931,361 A | 6/1990 | Baldeschwieler et al. |
| 4,933,145 A | 6/1990 | Uchida et al. .................. 422/61 |
| 4,946,648 A | 8/1990 | Dichtelmüller et al. .................. 422/24 |
| 4,963,356 A | 10/1990 | Calenoff et al. .................. 424/91 |
| 4,994,237 A | 2/1991 | Login et al. .................. 422/21 |
| 5,000,951 A | 3/1991 | Bass et al. .................. 424/89 |
| 5,012,503 A | 4/1991 | Nambu et al. |
| 5,044,091 A | 9/1991 | Ueda et al. |
| 5,106,619 A | 4/1992 | Wiesehahn et al. .................. 424/89 |
| 5,134,295 A | 7/1992 | Wälischmiller .................. 250/455.11 |
| 5,185,371 A | 2/1993 | Rubinstein .................. 422/28 |
| 5,226,065 A | 7/1993 | Held et al. .................. 378/64 |
| 5,283,034 A * | 2/1994 | Okrongly et al. .................. 422/22 |
| 5,362,442 A | 11/1994 | Kent .................. 422/22 |
| 5,418,130 A | 5/1995 | Platz et al. .................. 435/2 |
| 5,460,962 A | 10/1995 | Kemp .................. 435/238 |
| 5,510,122 A | 4/1996 | Sreebny et al. .................. 424/537 |
| 5,548,066 A | 8/1996 | Leneau et al. .................. 530/390.5 |
| 5,603,894 A | 2/1997 | Aikus et al. .................. 422/23 |
| 5,609,864 A | 3/1997 | Shanbrom .................. 424/78.08 |
| 5,637,451 A | 6/1997 | Ben-Hur et al. .................. 435/2 |

(List continued on next page.)

FOREIGN PATENT DOCUMENTS

| | | |
|---|---|---|
| CA | 2056619 | 10/1991 |
| EP | 0 310 316 | 4/1989 |
| EP | 0 334 679 | 9/1989 |
| EP | 919 918 A3 | 6/1999 |
| EP | 919 918 A2 | 6/1999 |
| EP | 0808167 B1 | 6/2002 |
| EP | 0820301 B1 | 7/2002 |
| JP | 11-216147 | 8/1999 |
| RU | 1321420 A | 7/1987 |
| WO | WO 90/00907 | 2/1990 |
| WO | WO 91/16060 | 10/1991 |
| WO | WO 95/03071 | 2/1995 |
| WO | WO 00/25839 | 3/2000 |
| WO | WO 00/28552 | 5/2000 |
| WO | WO 01/08611 A1 | 2/2001 |
| WO | WO 01/12318 A1 | 2/2001 |
| WO | WO 01/32107 A2 | 5/2001 |
| WO | WO 01/32110 A2 | 5/2001 |
| WO | WO 01/45720 A1 | 6/2001 |
| WO | WO 01/49219 A1 | 7/2001 |
| WO | WO 01/72233 A1 | 10/2001 |
| WO | WO 01/72244 A1 | 10/2001 |
| WO | WO 01/91818 A1 | 12/2001 |

OTHER PUBLICATIONS

Chin et al, Photochemistry and Photobiology, 65, 432–435, 1997.*

AABB FDA Liaison Meeting, ABC Newsletter, Dec. 12, 1997, pp. 14.

Tikvah Alper et al., The Exceptionally Small Size of the Scrapie Agent, 1966, pp. 278–284, Biochemical and Biophysical Research Communications, vol. 22, No. 3.

Tikvah Alper et al., Protection by Anoxia of the Scrapie Agent and Some DNA and RNA Viruses Irradiated as Dry Preparations, 1968, pp. 157–166, J. gen. Virol., vol. 3.

Tikvah Alper et al., Does the Agent of Scrapie Replicate Without Nucleic Acid? May 20, 1967, pp. 764–766, Nature, vol. 214.

(List continued on next page.)

*Primary Examiner*—David Saunders
(74) *Attorney, Agent, or Firm*—Fleshner & Kim, LLP

(57) ABSTRACT

Methods are disclosed for sterilizing preparation of monoclonal immunoglobulins to reduce the level of active biological contaminants such as viruses, bacteria, yeasts, molds, mycoplasmas, prions and parasites.

78 Claims, 42 Drawing Sheets

U.S. PATENT DOCUMENTS

| | | | |
|---|---|---|---|
| 5,643,464 A | 7/1997 | Rhee et al. | 210/748 |
| 5,712,086 A | 1/1998 | Horowitz et al. | 435/2 |
| 5,730,933 A | 3/1998 | Peterson | 422/22 |
| 5,817,528 A | 10/1998 | Böhm et al. | 436/529 |
| 5,856,172 A | 1/1999 | Greenwood et al. | |
| 5,989,498 A | 11/1999 | Odland | 422/22 |
| 6,010,719 A | 1/2000 | Remon et al. | |
| 6,060,233 A | 5/2000 | Wiggins | |
| 6,171,549 B1 * | 1/2001 | Kent | 422/22 |
| 6,187,572 B1 | 2/2001 | Platz et al. | 435/173.3 |
| 6,190,855 B1 | 2/2001 | Herman et al. | 435/2 |
| 6,197,207 B1 | 3/2001 | Chapman et al. | 210/767 |
| 6,203,544 B1 | 3/2001 | Gotzen | 606/72 |
| 6,214,534 B1 | 4/2001 | Horowitz et al. | 435/2 |
| 6,235,508 B1 | 5/2001 | Sowemimo-Coker et al. | 435/173.1 |
| 6,258,821 B1 | 7/2001 | Stogniew et al. | |
| 6,312,931 B1 * | 11/2001 | O'Dwyer | 435/173.1 |
| 6,346,216 B1 * | 2/2002 | Kent | 422/22 |
| 6,358,284 B1 | 3/2002 | Fearnot et al. | 623/23.72 |
| 6,375,989 B1 | 4/2002 | Badylak et al. | 424/551 |
| 6,383,732 B1 | 5/2002 | Stone | 435/1.1 |
| 6,384,419 B1 | 5/2002 | Purtle | 250/526 |
| 6,461,630 B1 | 10/2002 | Tucker et al. | 424/423 |
| 6,485,723 B1 | 11/2002 | Badylak et al. | 424/93.7 |
| 6,548,242 B2 | 4/2003 | Horowitz et al. | 435/2 |
| 2002/0064807 A1 | 5/2002 | Badylak et al. | 435/34 |
| 2002/0068267 A1 | 6/2002 | Horowitz et al. | 435/2 |
| 2002/0106394 A1 | 8/2002 | Tucker et al. | 424/423 |
| 2002/0188319 A1 | 12/2002 | Morris et al. | 606/213 |
| 2003/0068815 A1 | 4/2003 | Stone et al. | 435/325 |

OTHER PUBLICATIONS

Tikvah Alper et al., The Scrapie Agent: Evidence Against its Dependence For Replication on Intrinsic Nucleic Acid, 1978, pp. 503–516, J. gen. Virol., vol. 41.

Michael L. Baldwin et al., Irradiation of Blood Components, 1992, pp. 1–78, American Association of Blood Banks.

R.H. Bassin et al., Abrogation of Fv–1$^b$ Restriction With Murine Leukemia Viruses Inactivated by heat or by Gamma Irradiation, May 1978, pp. 306–315, Journal of Virology, vol. 26, No. 2.

Guy Beauregard et al., Temperature Dependence of the Radiation Inactivation of Proteins, 1985, pp. 117–120, Analytical Biochemistry, vol. 150.

David R. Brown et al., Antioxidant Activity Related to Copper Binding of Native Prion Protein, 2001, pp. 69–76, Journal of Neurochemistry, vol. 76.

P. Brown, The Risk of Blood–Borne Creutzfeldt–Jakob Disease, 1999, pp. 53–59, Advances in Transfusion Safety Dev. Biol. vol. 102.

P. Brown et al., Further Studies of Blood Infectivity in an Experimental Model of Transmissible Spongiform Encephalopathy, With an Explanation of Why Blood Components Do Not Transmit Creutzfeldt–Jakob Disease in Humans, Nov./Dec. 1999, pp. 1169–1178, Transfusion, vol. 39.

Paul Brown et al., Effect of Chemicals, Heat, and Histopathologic Processing on High–Infectivity Hamster--Adapted Scrapie Virus, May 1982, pp. 683–687, The Journal of Infectious Diseases, vol. 145, No. 5.

P. Brown et al., The Distribution of Infectivity in Blood Components and Plasma Derivatives in Experimental Models of Transmissible Spongiform Encephalopathy, Sep. 1998, pp. 810–816, Transfusion, vol. 38.

Derwent Publication AN—111469.

Derwent Publication—AN 2159557.

Derwent Publication—AN 2526936.

P. Di Simplicio et al., The Reactivity of the SH Group of Bovine Serum Albumin With Free Radicals, 1991, pp. 253–262, Free Rad. Res. Comms., vol. 14, No. 4.

Duane C. Eichler et al., Radiation Inactivation Analysis of Enzymes, Jul. 15, 1987, pp. 9433–9436, The Journal of Biological Chemistry, vol. 262, No. 20.

Luanne H. Elliott et al., Inactivation of Lassa, Marburg, and Ebola Viruses by Gamma Irradiation, Oct. 1982, pp. 704–708, Journal of Clinical Microbiology, vol. 16, No. 4.

Fields et al., Susceptibility of Scrapie Agent to Ionizing Radiation, Apr. 5, 1969, pp. 90–91, Nature, vol. 222.

D.A. Haig, Further Studies on the Inactivation of the Scrapie Agent by Ultraviolet Light, 1969, pp. 455–457, J. gen. Virol., vol. 5.

H. Hiemstra et al., Inactivation of Human Immunodeficiency Virus by Gamma Radiation and its Effect on Plasma and Coagulation Factors, 1991, pp. 32–39, Transfusion, vol. 31, No. 1.

B. Horowitz et al., Inactivation of Viruses in Labile Blood Derivatives, II. Physical Methods, 1985, pp. 523–527, Transfusion, vol. 25, No. 6.

Carol House et al., Inactivation of Viral Agents in Bovine Serum by Gamma Irradiation, 1990, pp. 737–740, Can. J. Microbiol., vol. 36.

E.S. Kempner et al., Size Determination of Enzymes by Radiation Inactivation, 1979, pp. 2–10, Analytical Biochemistry, vol. 92.

J.D. Keathley et al., Is There Life After Irradiation? Part 2: Gamma–Irradiated FBS in Cell Culture, Jul./Aug. 1993, pp. 46–52, BioPharm.

A.D. Kitchen, Effect of Gamma Irradiation on the Human Immunodeficiency Virus and Human Coagulation Proteins, 1989, pp. 223–229, Vox Sang, vol. 56.

Raymond Latarjet, Inactivation of the Agents of Scrapie, Creutzfeldt–Jakob Disease, and Kuru by Radiations, 1979, pp. 387–407, Slow Transmissible Diseases of the Nervous System, vol. 2.

R. Latarjet et al., Inactivation of the Scrapie Agent by Near Monochromatic Ultraviolet Light, Sep. 26, 1970, pp. 1341–1343, Nature, vol. 227.

Douglas C. Lee et al., A Direct Relationship Between the Partitioning of the Pathogenic Prion Protein and Transmissible Spongiform Encephalopathy Infectivity During the Purification of Plasma Proteins, Apr. 2001, pp. 449–455, Transfusion, vol. 41.

Susan F. Leitman, Use of Blood Cell Irradiation in the Prevention of Posttransfusion Graft–vs–Host Disease, 1989, pp. 219–232, Transfus. Sci., vol. 10.

Linda Marton et al., Disinfection and Inactivation of the Human T. Lymphotrogic Virus Type III/Lymphadenopathy–Associated Virus, Aug. 1985, pp. 400–403,The Journal of Infectious Diseases, vol. 151, No. 2.

S.I. Miekka et al., New Methods for Inactivation of Lipid–enveloped and Non–enveloped Viruses, 1998, pp. 402–408, Haemophilia, vol. 4.

Z. Mark Plavsic et al., Resistance of Porcine Circovirus to Gamma Irradiation, Apr. 2001, pp. 32–36, BioPharm.

Pollard, The Effect of Ionizing Radiation on Viruses, pp. 65–71.

Elena Quaglio et al., Copper Converts the Cellular Prion Protein Into a Protease–resistant Species That Is Distinct From the Scrapie Isoform, Apr. 6, 2001, pp. 11432–11438, The Journal of Biological Chemistry, vol. 276, No. 14.

Brian D. Reid, The Sterways Process: a New Approach to Inactivating Viruses Using Gamma Radiation, 1998, pp. 125–130, Biologicals, vol. 26.

Robert G. Rohwer, Estimation of Scrapie Nucleic Acid MW From Standard Curves for Virus Sensitivity to Ionizing Radiation, Mar. 27, 1986, pp. 381, Nature, vol. 320, No. 6060.

Robert G. Rohwer, Scrapie Infectious Agent is Virus–like in Size and Susceptibility to Inactivation, Apr. 12, 1984, pp. 658–662, Nature, vol. 308.

R.G. Rohwer, The Scrapie Agent: "A Virus by Any Other Name", pp. 195–232, Current Topics In Microbiology and Immunology, vol. 172.

Robert G. Rohwer et al., Scrapie—Virus or Viroid, The Case For A Virus, pp. 333–355, Laboratory of Central Nervous System Studies, National Institutes of Neurological and Communicative Disorders and Stroke, National Institutes of Health.

Robert G. Rohwer, Virus–Like Sensitivity of the Scrapie Agent to heat Inactivation, Feb. 10, 1984, pp. 600–602, Science, vol. 223.

Robert Sullivan et al. Inactivation of Thiry Viruses by Gamma Radiation, Jul. 1971, pp. 61–65, Applied Microbiology, vol. 22, No. 1.

Boon–Seng Worg et al., Copper Refolding of Prion Protein, 2000, pp. 1217–124, Biochemical and Biophysical Research Communications, vol. 276.

Boon–Seng Wong et al., Differential Contribution of Superoxide Dismutase Activity by Prion Protein in Vivo, 2000, pp. 136–139, Biochemical and Biophysical Research Communications, vol. 273.

Boon–Seng Wong et al., Prion Disease: A Loss of Antioxidant Function? 2000, pp. 249–252, Biochemical and Biophysical Research Communications, vol. 275.

D.E. Wyatt et al., Is There Life After Irradiation? Part I: Inactivation of Biological Contaminants, Jun. 1993, pp. 34–39, BioPharm.

License Amendment and Procedures for Gamma Irradiation of blood Products, Jun. 22, 1993, pp. 1–18, Dept. of Health & Human Services, Food and Drug Administration.

M.F. Alladine et al., γ–Radiation Damage to Starr–Edwards Valves, Mar. 16, 1968, pp. 68, The Lancet Letters to the Editor.

Ch. Baquey et al., Radiosterilization of Albuminated Polyester Prostheses, May 1987, pp. 185–189, Biomaterials, vol. 8.

Edward H. Bedrossian, Jr., HIV and Banked Fascia Lata, 1991, pp. 284–288, Ophthalmic Plastic and Reconstructive Surgery, vol. 7, No. 4.

Liu Bingci, Mouse Antibody Response Following Repetitive Injections of Gamma–Irradiated human Placenta Collagen, Jun. 1994, pp. 100–103, Chinese Medical Sciences Journal, vol. 9, No. 2.

E.A. Borisov et al., Protein Degradation During Interphase Death of Thymocytes Induced by Radiation and Dexamethasone, 1990, pp. 519–521 Abstract Only.

R.G. Burwell, The Fate of Freeze–Dried Bone Allografts, Jun. 1976, pp. 95–111, Transplantation Proceedings, vol. VII, No. 2, Supplement 1.

L. Callagaro et al., Hollow Fiber Immobilized L–Asparaginase: In Vivo and In Vitro Immunological Studies, 1983, pp. 91–96, The International Journal of Artificial Organs, vol. 6, No. 2.

G. Campalani et al., Aortic Valve Replacement With Frozen Irradiated Homografts, 1989, pp. 558–561, Eur. J. Cardio–thoracic Surgery, vol. 3.

David T. Cheung et al., The Effect of γ–Irradiation on Collagen Molecules, Isolated α–chains, and Crosslinked Native Fibers, 1990, pp. 581–589, Journal of Biomedical Materials Research, vol. 24.

David J. Cohen et al., The Fate of Aortic Valve Homografts 12 to 17 Years After Implantation, Mar. 1988, pp. 482–484, Chest, vol. 93, No. 3.

A.G. Chuchalin et al., Clinical Immunosorbents Basing On Space–Network Polymers, 1998, pp. 1524–1529, All Union Research Institute of Chemical Reagents and Chemicals of Special Purity, Moscow.

P. De Deyne et al., Some Effects of Gamma Irradiation on Patellar Tendon Allografts, 1991, pp. 51–62, Connective Tissue Research, vol. 27.

E.A. Dyskin et al., Hemomicrocirculatory Bed in the Wall of Hollow Organs of the Dog Gastrointestinal Tract at Portal Hypertension, pp. 68–73 Abstract Only.

R. Guidoin et al., A Compound Arterial Prosthesis: The Importance of the Sterilization Procedure on the Healing and Stability of Albuminated Polyester Grafts, Mar. 1985, pp. 122–128, Biomaterials, vol. 6.

Ph. Hernigou et al., Radiation Sterilization of Bone and the HIV Virus, 1993, pp. 445–451, Revue de Chirurgie Orthopedique, vol. 79, Summary Only.

Hsing–Wen Sung et al. Effects of Various Chemical Sterilization Methods on the Crosslinking and Enzymatic Degradation Characteristics of an Epoxy–Fixed Biological Tissue, Dec. 1996, pp. 376–383, Sterilization of Biological Tissues.

James R. Malm et al., An Evaluation of Aortic Valve Homografts Sterilized by Electron Beam Energy, Oct. 1967, pp. 471–477, Journal of Thoracic and Cardiovascular Surgery, vol. 54, No. 4.

James R. Malm et al., Results of Aortic Valve Replacement Utilizing Irradiated Valve Homografts, pp. 740–747, Annals New York Academy of Sciences.

W. Oh et al., Mitral Valve Replacement With Preserved Cadaveric Aortic Homografts, May 1973, pp. 712–721, The Journal of Thoracic and Cardiovascular Surgery, vol. 65, No. 5.

K. Pietrucha, New Collagen Implant As Dural Substitute, Apr. 1991, pp. 320–323, Biomaterials, vol. 12.

Maria Raptopoulou–Gigi et al., Antimicrobial Proteins in Sterilised Human Milk, Jan. 1, 1977, pp. 12–14, British Medical Journal, vol. 1.

Edward A. Rittenhouuse et al., Sterilization of Aortic Valve Grafts for Transplantation, Jul . 1970, pp. 1–5, Aortic Valve Grafts for Transplantation, Archives of Surgery, vol. 101, No. 1.

H. Sato et al., Sterilization of Therapeutic Immunoadsorbents by Ionizing Radiation, 1986, pp. 131–136, The International Journal of Artificial Organs, vol. 9, No. 2.

Richard A. Smith et al., Gamma Irradiation of HIV–1, 2001, pp. 815–819, Journal of Orthopaedic Research, vol. 19.

Barbara Lüssi–Schlatter et al., Die Antimikrobielle Behandlung von Peroralen Enzympräparaten mit Gamma–Strahlen, Pharmazeutisches Institut der Eidgenössischen Technischen Hochschule Zürich Galenische Abteilung Summary Only.

Ozan Akkus et al., Fracture Resistance of Gamma Radiation Sterilized Cortical Bone Allografts, 2001, pp. 927–934, Journal of Orthopaedic Research, vol. 19.

S.R. Aparicio et al., Light and Electron Microscopy Studies on Homograft and Heterograft Heart Valves, 1975, pp. 174–162, J. Path., vol. 115.

J. Baksa et al., The Use of Pig's Skin (xenograft) for the Treatment of Burns, 1976, pp. 138–145, Magyar Traumatologin, vol. 19, Abstract Only.

Seymour S. Block, Disinfection, Sterilization, and Preservation, Fundamental Principles of Activity, Principles of Antimicrobial Activity, Fourth Edition, 1991, pp. 31–33.

A.J.J.C. Bogers et al., Long–Term Results of the Gamma–Irradiation–Preserved Homograft Monocusp for Transannular Reconstruction of the Right–Ventricular Outflow Tract in Tetralogy of Fallot, 1994, pp. 337–339, Thorac. Cardiovasc. Surgeon, vol. 42.

Blakeslee, Sandra, Jan. 20, 2002, The New York Times.

D.G. Campbell et al., Sterilization of HIV With Irradiation: Relevance to Infected Bone Allografts, 1999, pp. 517–521, Aust. N.Z.J. Surg., vol. 69.

Ernest U. Conrad et al., Transmission of the Hepatitis–C Virus by Tissue Transplantation, Feb. 1995, pp. 214–224, The Journal of Bone and Joint Surgery, vol. 77–A, No. 2.

A.S. Dagli, Correction of Saddle Nose Deformities by Coral Implantation, 1997, pp. 274–276, Eur Arch Otorhinolaryngol, vol. 254.

Defeng et al., Sterilization of Silver–Acidum Pipemedicum Skin for the Treatment of Burns by Radioactive Cobalt–60–.Gamma.–Ray, 1995, pp. 406 (Abstract).

R.J. Donnelly et al., Gamma–radiation of Heart Valves at 4° C; A Comparative Study Using Techniques of Histochemistry and Electron and Light Microscopy, 1978, pp. 95–101.

Bradley M. Fideler et al., Gamma Irradiation: Effects on Biomechanical Properties of Human Bone–Patellar Tendon–Bone Allografts, 1995, pp. 643–646, American Journal of Sports Medicine, vol. 23, No. 5.

Bradley M. Fideler et al., Effects of Gamma Irradiation on the Human Immunodeficiency Virus, Jul. 1994, The Journal of Bone and Joint Surgery, vol. 76–A, No. 7.

J.R.P. Gibbons et al., Effects of Gamma Irradiation on the Initial Mechanical and Material Properties of Goat Bone–Patellar Tendon–Bone Allografts, 1991, pp. 209–218, J. Orthop Res, vol. 9, No. 2.

J.R.P. Gibbons et al., Gamma Ray Sterilisation of Homograft Valves, 1969, pp. 353–358, Bulletin De La Societe Internationale De Chirugie, No. 3.

M.J. Goertzen et al., Anterior Cruciate Ligament Reconstruction Using Cryopreserved Irradiated Bone–ACL–Bone–Allograft Transplants, 1994, pp. 150–157, Knee Surgery Sports Traumatology Arthroscopy, vol. 2.

M.J. Goertzen et al., Sterilisation of Canine Anterior Cruciate Allografts by Gamma Irradiation in Argon, Mar. 1995, pp. 205–212, The Journal of Bone and Joint Surgery, vol. 77–B, No. 2.

Slawomir Gregorczyn et al., Strength of Lyophilized and Irradiated Cortical Bone of the Human Femur, 1995, pp. 129–133, Chir. Narz. Ruchu Ortop. Pol., Lx 2 Abstract Only.

F.W. Hehrlein et al., Biochemische Veränderungen an Heterologen Aortenklappentransplantaten nach Anwendung Verschiedener Sterilisationsverfahren, pp. 1183–1185, Langenbecks Arch. Chir., Bd. 325 (Kongrebericht) (English Summary found at p. 1183) Abstract Only.

F.W. Hehrlein et al., Morphologische Utersuchungen an Heterologen Herzklappentransplantaten Unter Verschiedenen Sterilisationsbedingungen, pp. 244–251 (English Summary found at p. 250).

Richard Hinton et al., A Biomechanical Analysis of Solvent–de hydrated and Freeze–Dried Human Fascia Lata Allografts, 1992, pp. 607–612, The American Journal of Sports Medicine, vol. 20, No. 5.

M. Horowitz, Sterilization of Homograft Ossicles by Gamma Radiation, Nov. 1979, pp. 1087–1089, The Journal of Laryngology and Otology, vol. 93.

Shinichiro Ijiri et al., Effect of Sterilization on Bone Morphogenetic Protein, 1994, pp. 628–636, Journal of Orthopaedic Research, vol. 12.

A.S. Imamaliev et al., Biological Properties of Bone Tissue Conserved in Plastic Material and Sterilized With Gama Rays, 1974, pp. 129–135, ACTA, Chirurgiae Plasticae, vol. 16, No. 3.

A. Ingegneri et al., An 11–Year Assessment of 93 Flash–frozen Homograft Valves in the Aortic Position, 1979, pp. 304–307, Thorac. Cardiovasc. Surgeon, vol. 27.

J. Jerosch et al., A New Technique for Bone Sterilization, 1989, pp. 117–120, Biomedizinische Technik, Band 34, Heft 5.

J. Jerosch et al., Influence of Different Rehydration Periods on the Stability and the Water Content of Bone Allografts After Lyophilization, Gamma–Irradiation, and Lipid Extraction, 1994, pp. 335–341, Z. Orthop., vol. 132.

L. Kerboull et al., In Vitro Study of the Influence of Various Conservation Methods on the Mechanical Properties of Patellar Tendon Allografts, 1991, pp. 751–762, Chirurgie, vol. 117.

Andrezej Komender et al., Some Biological Properties of Bovine Trypsinized Fascia Xenografts, 1981, pp. 485–489, Archivum Immunologiae et Therapiae Experimentalis, vol. 29.

Andrezej Komender et al., Some Biological Properties of Preserved Bovine Fascia Enriched With Pulverized Calf Cartilage, 1984, pp. 211–219, Archivum Immunologiae et Therapiae Experimentalis, vol. 32.

J.F. Kouvalchouk et al., The Use of Sterilized Bone Allografts in Reconstruction After Tumour Resection, 1986, pp. 393–401, Revue de Chirurgie Orthopedique, vol. 72.

Linberg et al., Irradiated Homologous Cartilage For Orbital Reconstruction, Jul. 1980, pp. 457–462, Ophthalmic Surgery, vol. 11.

McDowell, Sandra, Irradiated Cartilage, Spring 1988, pp. 14–15, Plastic Surgical Nursing.

A. Maeda et al., Effects of Solvent Preservation With or Without Gamma Irradiation on the Material Properties of Canine Tendon Allografts, 1993, pp., 181–189, Journal of Orthopaedic Research, vol. 11.

Akira Maeda et al., Solvent–dried and Gamma–irradiated Tendon Allografts in Rats, Jul. 1998, pp. 731–736, The Journal of Bone and Joint Surgery, vol. 80–B, No. 4.

S. Malawaski et al., The Use of Dry–Freezed Bone Grafts Sterilized by Gamma Rays in Orthopaedic Surgery, 1969, pp. 61–68, Chir. Narz. Ruchu Ortop. Summary Only.

Ken Nakata et al., Reconstruction of the Laterial Ligaments of the Ankle Using Solvent–dried and Gamma–Irradiated Allogeneic Fascia Lata, May 2000, pp. 579–582.

Maria Esther Martinez Pardo et al., Clinical Application of Amniotic Membranes on a Patient With Epidermolysis Bullosa, 1999, pp. 68–73, Annals of Transplantation, vol. 4, No. 3–4.

Jan Parizek et al., Duraplasty With Pretreated Freeze–Dried Sterilized Human Dura Mater, 1990, pp. 135–143, Sbor. ved. Praci LF UK Hradee Kralove, vol. 33.

Jan Parizek et al., Ovine Pericardium: A New Material For Duraplasty, 1996, pp. 508–513, J. Neurosurg., vol. 84.

Patel et al., Effect of Gamma Radiation and Ethylene Oxide on Papain, 1979, pp. 81–83, Indian. J. Pharm. Sci., vol. 41, No. 2.

L.V. Polezhaeu et al., Repair of Cranial Defects With Regenerating Bone in Grafting Gamma–Irradiated Bone Filings, pp. 57–60 Summary Only.

Donald J. Prolo et al., Composite Autogeneic Human Cranioplasty: Frozen Skull Supplemental With Fresh Iliac Corticocancellous Bone, Dec. 1984, pp. 846–851, Neurosurgery, vol. 15, No. 6.

Donald J. Prolo et al., Superior Osteogenesis in Transplanted Allogeneic Canine Skull Following Chemical Sterilization, Aug. 1982, pp. 230–242, Clinical Orthopaedics and Related Research, No. 168.

T.J. Rasmussen et al., The Effects of 4 Mrad of Gamma–Irradiation on the Initial Mechanical Properties of Bone–Patellar Tendon–Bone Grafts, 1994, pp. 188–197, The Journal of Arthroscoic and Related Surgery, vol. 10, No. 2.

S.C. Roe et al., The Effect of Gamma Irradiation on a Xenograft Tendon Bioprothesis, 1992, pp. 149–154, Clinical Materials, vol. 9.

D. Tylman, Mechanical Character of Liofilized and Sterilized by Gamma–Rays Bone Tissue, 1996, pp. 229–234, Chirurgia Narzadow Ruchu I, Ortopedia Polska Summary Only.

W. Welch, A Comparative Study of Different Methods of Processing Aortic Homografts, 1969, pp. 746–749, Thorax, vol. 24.

J.M. White et al., Sterilization of Teeth by Gamma Radiation, Sep. 1994, pp. 1560–1567, J. Dent. Res., vol. 73, No. 9.

Qi Zhang et al., Ethylene Oxide Does Not Extinguish the Osteoinductive Capacity of Demineralized Bone, 1997, pp. 104–108, Acta Orthop Scand, vol. 68, No. 2.

Yongxing Zhang et al., A Comprehensive Study of Physical Parameters, Biomechanical Properties and Statistical Correlations of Iliac Crest Bone Wedges Used in Spinal Fusion Surgery, 1994, pp. 304–308, Spine, vol. 19, No. 3.

A.A. Belov et al., The Influence of γ–radiation on Enzyme Activity of Collalitin in the Process of Storage Dec. 7, 1989, pp. 519–521, All–Union Research Institute of Textile and Haberdashery Industry, Moscow.

R.I. Vaida et al., Structural–Functional Peculiarities of Myocardial Capillaries After Resection of the Lungs, Oct. 21, 1986, pp. 68–73 Summary Only.

Martindale's Extra Pharmacopoecia, Glucose, pp. 1265.

The Merck Index, Eleventh Edition Glucose, pp. 4353–4354.

G.L. Moore et al., Effects of 4000 Rad. Irradiation on the In Vitro Storage Properties of Packed Red Cells, Nov.–Dec. 1985, pp. 583–585, Final Rept., Pub. In Transfusion, vol. 25, No. 6 (Abstract).

Shcheglova et al. The Effect of the Power of Gamma–Radiation on the Radiation Dose in the Sterilization of Drugs, 1984, pp. 730–732, Khim–Farm Zh, vol. 18, No. 6 (Abstract).

G.A. Yarygina, Dose Rate Effect on Survival of Microorganisms Used as Test–Cultures in Radiation Sterilization of Medical Products, 1973, pp. 32–39, Radiats. Tekh., No. 9 (Abstract.

Blanchy, B.B. et al., Immobilization of Factor VIII on Collagen Membranes, J. Biomedical Materials Research, 20:469–479 (1986) (John Wiley & Sons, Inc.).

Boyer, T.D. et al., Radiation Inactivation of Microsomal Glutathione S–Transferase, The Journal of Biological Chemistry, 261:16963–16968 (1986).

Chanderkar, L.P. et al., The Involvement of Aromatic Amino Acids in Biological Activity of Bovine Fibrinogen as Assessed by Gamma–Irradiation, Radiation Research, 65:283–291 (1976) (Academic Press. Inc.).

Chanderkar, L.P. et al., Radiation–Induced Changes In Purified Prothrombin and Thrombin, Biochimica et Biophysica Acta, 706:1–8 (1982) (Elsevier Biomedical Press).

Chin, S. et al., Virucidal Treatment of Blood Protein Products With UVC Radiation, Photochemistry and Photobiology, 65:432–435 (1997) (American Society for Photobiology).

Ghosh, M.M. et al., A Comparison of Methodologies for the Preparation of Human Epidermal–Dermal Composites, Annals of Plastic Surgery; 39:390–404 (1997) (Lippincott–Raven Publishers).

Hsiue, G. et al., Absorbable Sandwich–Like Membrane for Retinal–Sheet Transplantation, pp. 20–25 (2002) (Wiley Periodicals, Inc).

Jensen, J. et al., Membrane–bound Na, K–ATPase: Target Size and Radiation Inactivation Size of Some of Its Enzymatic Reactions, J. Biological Chemistry, 263:18063–18070 (1988) (Am. Soc. for Biochem. And Mol. Biol.).

Kamat, H.N. et al., Correlation of Structural Alterations in Bovine Fibrinogen with Loss of Clotting Properties After Gamma Irradiation, Radiation Research, 49:381–389 (1972) (Academic Press, Inc.).

Kempner, E.S. et al., Effect of Invironmental Conditions on Radiation Target Size Analyses, Analytical Biochemistry, 216:451–455 (1994).

Kempner, E.S. et al., Radiation–Damaged Tyrosinase Molecules are Inactive, Biophysical Journal, 55:159–162 (1989) (Biophysical Society).

Kuijpers, A.J. et al., In vivo Compatibility and Degradation of Crosslinked Gelatin Gels Incorporated in Knitted Dacron, pp. 137–144 (2000) (John Wiley & Sons, Inc.).

Le Maire, M. et al., Effects of Ionizing Radiations on Proteins, Journal of Biochem., 267:431–439 (1990).

Ma, J.T. et al., Functional Size Analysis of F–ATPase from *Escherichia coli* by Radiation Inactivation, The Journal of Biological Chemistry, 268:10802–10807 (1993) (The Am. Soc. for Biochem. and Mol. Bio., Inc.).

Marx, G. Protecting Fibrinogen with Rutin During UVC Irradiation for Viral Inactivation, Photochemistry and Photobiology, 63:541–546 (1996) (American Society for Photobiology).

Nagrani, S. et al., The Radiation–Induced Inactivation of External Yeast Invertase in Dilute Aqueous Solution, Int. J. Radiat. Biol., 55:191–200 (1989) (Taylor & Francis Ltd.).

Nielsen, M. et al., The Apparent Target Size of Rat Brain Benzodiazepine Receptor, Acetylcholinesterase, and Pyruvate Kinase Is Highly Influenced by Experimental Conditions, The Journal of Biological Chemistry, 263:11900–11906 (1988) (The American Society for Biochemistry and Molecular Biology, Inc.).

Potier, M. et al., Radiation Inactivation of Proteins: Temperature–Dependent Inter–Protomeric Energy Transfer in Ox Liver Catalase, Biochem. J., 298:571–574 (1994).

Sakai, T. et al., Microbiological Studies on Drugs and Their Raw Materials. IV. Sterilization of Microbial Contaminants in Enzyme Powder by Gamma Irradiation, Chem. Pharm. Bull., 26:1130–1134 (1978).

Salim–Hanna, M. et al., Free Radical Scavenging Activity Of Carnosine, Free Rad. Res. Comms., 14:263–270 (1991) (Harwood Academic Publishers GmbH).

Suomela, H., Inactivation of Viruses in Blood and Plasma Products, Transfusion Medicine Reviews, 7:42–57 (1993) (W.B. Saunders Company).

Song, K.B. et al., Effect of Gamma–irradiation on the Physicochemical Properties of Blood Plasma Proteins, 2002 Annual Meeting and Food Expo–Anaheim, California, Session 30C–1, Food and Chemistry: Proteins, (Jun. 2002) (Abstract).

(Abstract of EP091918A2 and EP0919198A3 (Delphion–DERABS Abstract #G1999–304614)).

Website: www.wslfweb.org/docs/dstp2000.dtopdf/19–MD-.pdf (Defense Science and Technology Plans, (Feb. 2000) p. 176, Section II, MD.03, U.S. Department of Defense Deputy Under Secretary of Defense (Science and Technology)).

Website: www.usacc.org/ataccc/ppt.html, (Advanced Technology Applications for Combat Casualty Care, 2001 Presentations, US Army Medical Research and Material Command Combat Casualty CareResearch Program (2001)).

Website: www.usacc.org/RevisedStepB.html, Bakaltcheva, I. et al., (FY01 Request for Proposals–Intramural–Revised 2, Combat Casualty Care Research Program, (2002)).

Website: www.benvue,com/history/history_content.html, (2002).

Website: www.phase–technologies.com/html/vol.2no1.html , Jennings, T.A., (Glossary of Terms for Lyophilization) (1999).

Website: www.phase–technologies.com/html/vol.1no9.html , Jennings, T.A., (Overview of the Lyophilization Process) (1998).

Website: www.phase–technologies.com/html/vol.1no2.html , Jennings, T.A., (Role of Product Temperature in the Lyophilization Process) (1998).

Website: www.phase–technologies.com/html/vol.2no2.html , Jennings, T.A., (What I Wish I Knew About Lyophilization) (1999).

Website: www.phase–technologies.com/html/vol.1no7.html , Jennings, T.A., (Which Shelf Temperature During Lyophilization?) (1998).

Website: www.phase–technologies.com/html/vol.1no10.html , Jennings, T.A., (Yes, You have no Eutectic) (1998).

O. Cornu et al., Effect of Freeze–Drying and Gamma Irradiation on the Mechanical Properties of Human Cancellous Bone, 2000, pp. 426–431, Journal of Orthopaedic Research, vol. 18.

Anna Dziedzic–Goclawska et al., Effect of Radiation Sterilization on the Osteoinductive Properties and the Rate of Remodeling of Bone Implants Preserved by Lyophilization and Deep–Freezing, Nov. 1991, pp. 30–37, Clinical Orthopaedics and Related Research, No. 272.

Ole T. Jensen et al., Vertical Guided Bone–Graft Augmentation in a New Canine Mandibular Model, 1995, pp. 335–343, The International Journal of Oral and Maxillofacial Implants, vol. 10, No. 3.

Ronald W. Katz et al., Radiation–Sterilized Insoluble Collagenous Bone Matrix is a Functional Carrier of Osteogenin for Bone Induction, 1990, pp. 183–185, Calcified Tissue International, vol. 47.

Everard Munting et al., Effect of Sterilization on Osteoinduction; 1988, pp. 34–38, Acta Orthop Scand, vol. 59, No. 1.

P.A. Puolakkainen et al., The Effect of Sterilization on Transforming Growth Factor β Isolated From Demineralized Human Bone, 1993, pp. 679–685, Transfusion, vol. 33, No. 8.

U. Ripamonti et al., Long–Term Evaluation of Bone Formation by Osteogenic Protein 1 in the Baboon and Relative Efficacy of Bone–Derived Bone Morphogenetic Proteins Delivered by Irradiated Xenogeneic Collagenous Matrices, 2000, pp. 1798–1809, Journal of Bone and Mineral Research, vol. 15, No. 9.

A. Salehpour et al., Dose–Dependent Response of Gamma Irradiation on Mechanical Properties and Related Biochemical Composition of Goat Bone–Patellar Tendon–Bone Allografts, 1995, pp. 898–906, Journal of Orthopaedic Research, vol. 13.

Nikolaus Schwarz et al., Irradiation–sterilization of Rat Bone Matrix Gelatin, 1988, pp. 165–167, Acta Orthop Scand, vol. 59, No. 2.

C.W. Smith et al., Mechanical Properties of Tendons: Changes With Sterilization and Preservation, Feb. 1996, pp. 56–61, Journal of Biomechanical Engineering, vol. 118.

Yukiyoshi Toritsuka et al., Effect of Freeze–Drying or γ–Irradiation on Remodeling of Tendon Allograft in a Rat Model, 1997, pp. 294–300, Journal of Orthopaedic Research, vol. 15.

Konrad Wangerin et al., Behavior of Differently Sterilized Allogenic Lyophilized Cartilage Implants in Dogs, 1987, pp. 236–242, J. Oral Maxillofac Surg. vol. 45.

S. Wientroub et al., Influence of Irradiation on the Osteoinductive Potential of Demineralized Bone Matrix, 1988, pp. 255–260, Calicified Tissue International, vol. 42.

Robert J. Woods, "Food Irradiation," Endeavor, New Series, vol. 18, No. 3, 1994, pp. 104–108.

A. Dziedzic–Goclawska et al., "Sterilisation of Tissue Allografts," Advances in Tissue Banking, vol. 1, pp. 261–321.

M.J. Goertzen et al., "Sterilisation of Canine Anterior Cruciate Allografts by Gamma Irradiation in Argon," Journal of Bone and Joint Surgery (Corrections), vo. 77–B, No. 2, Mar. 1995, pp. 205–212.

* cited by examiner

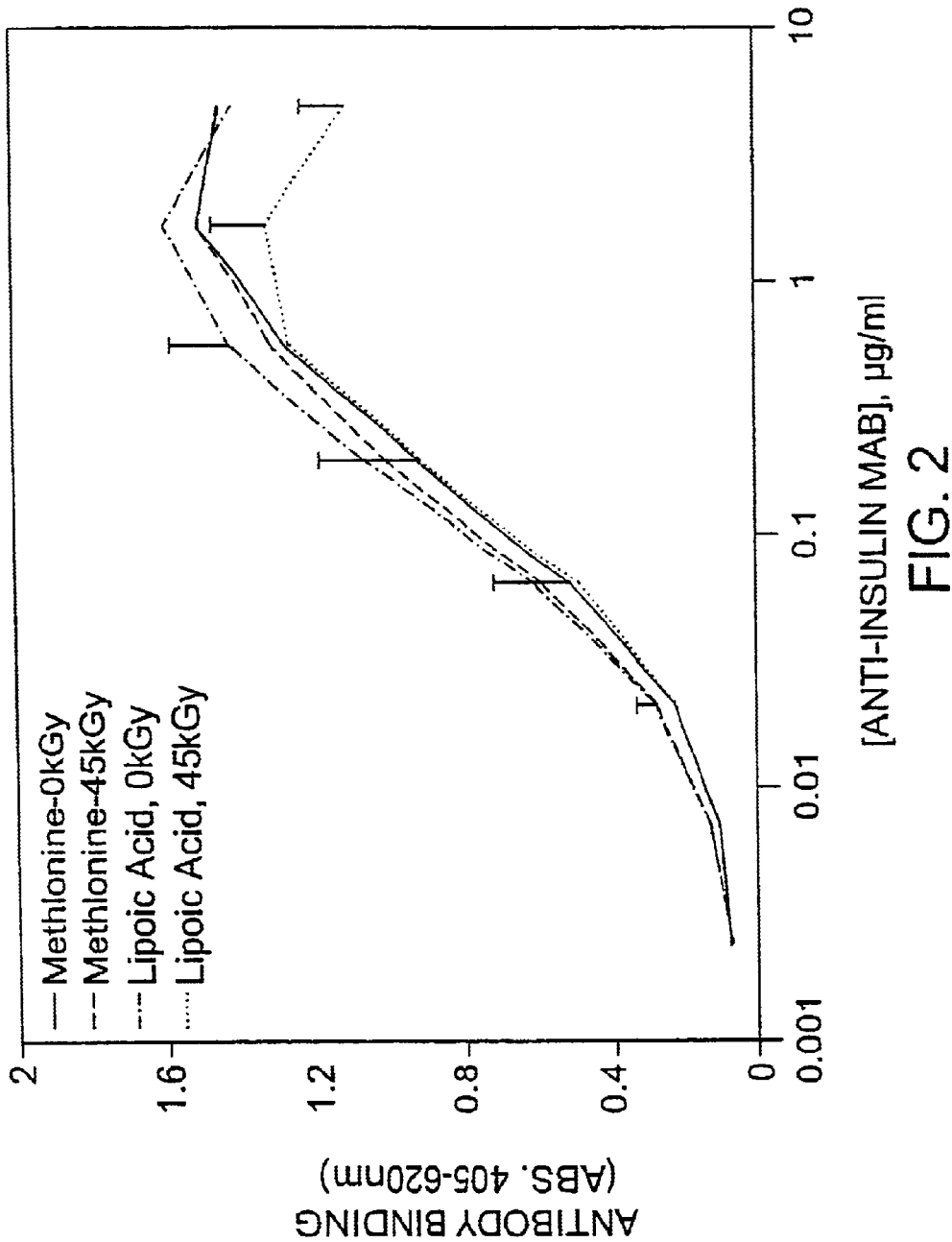

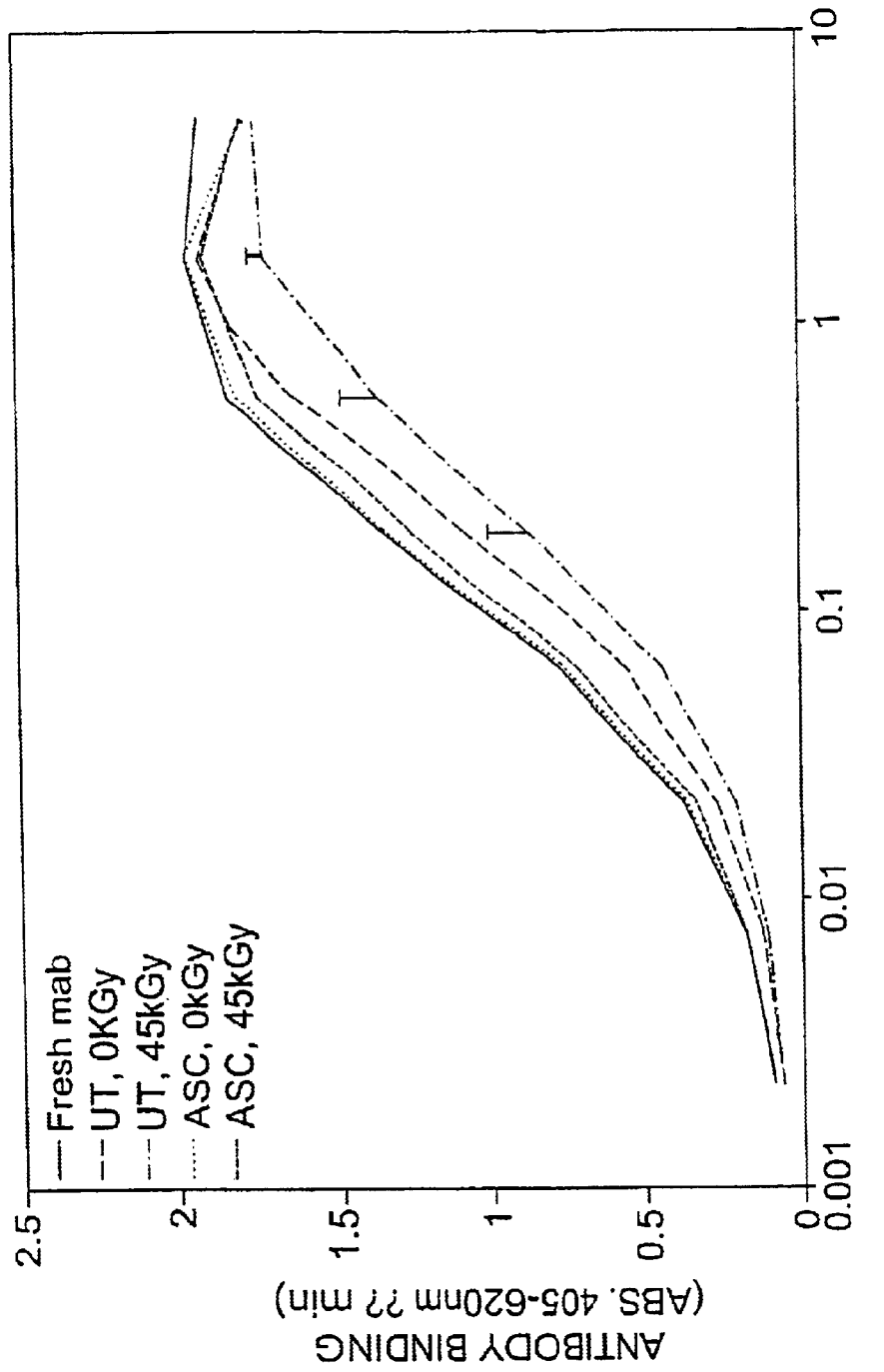

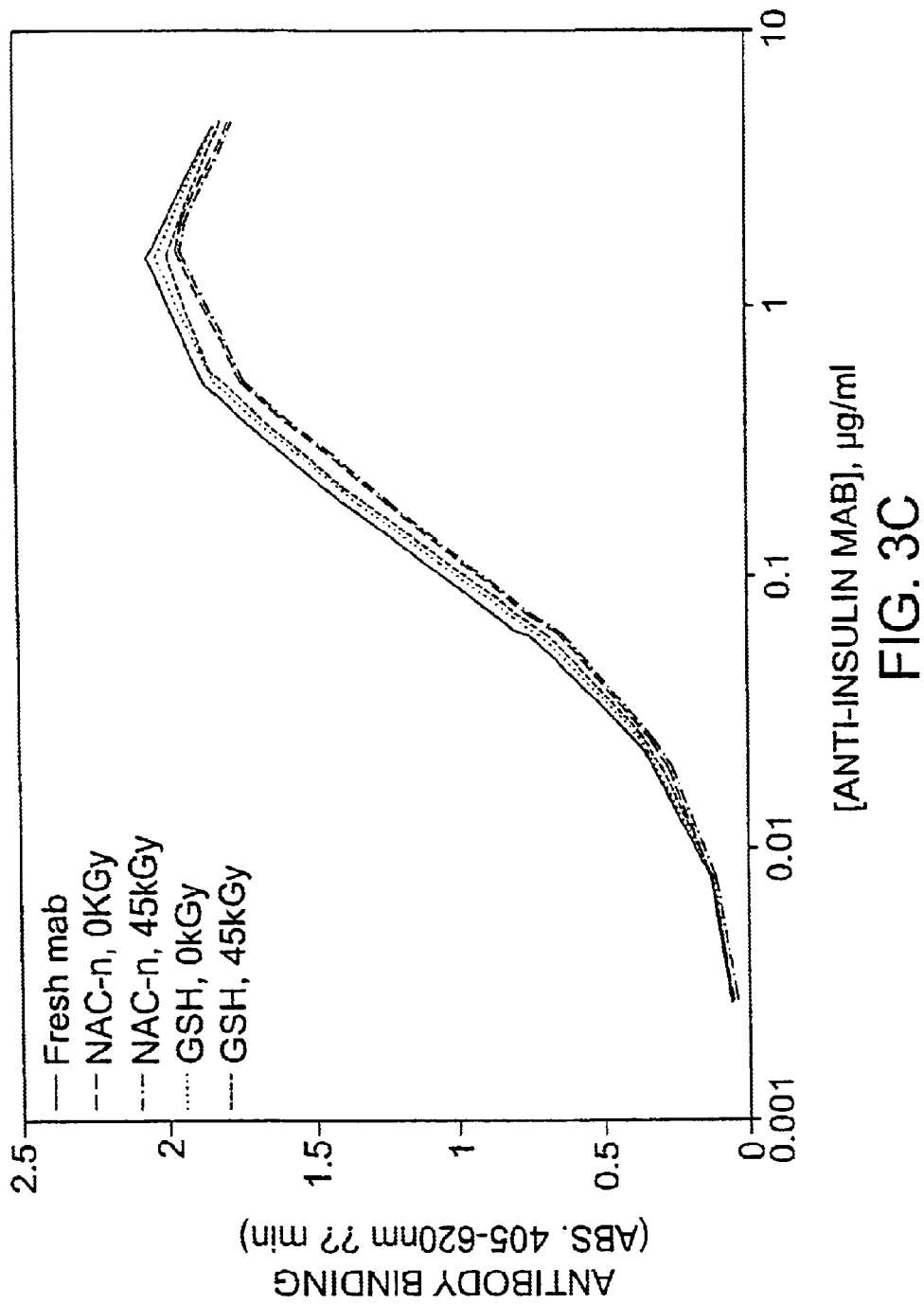

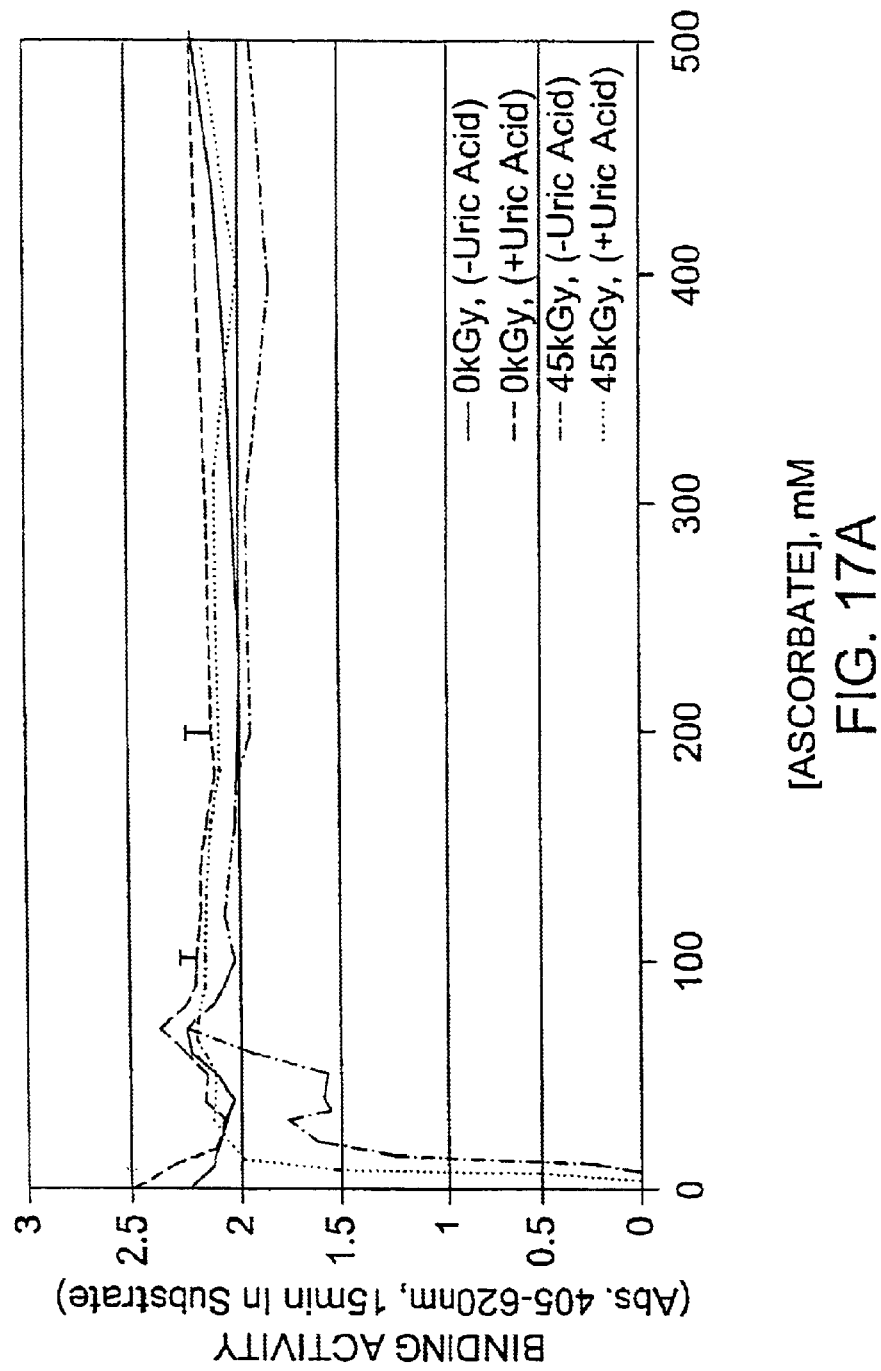

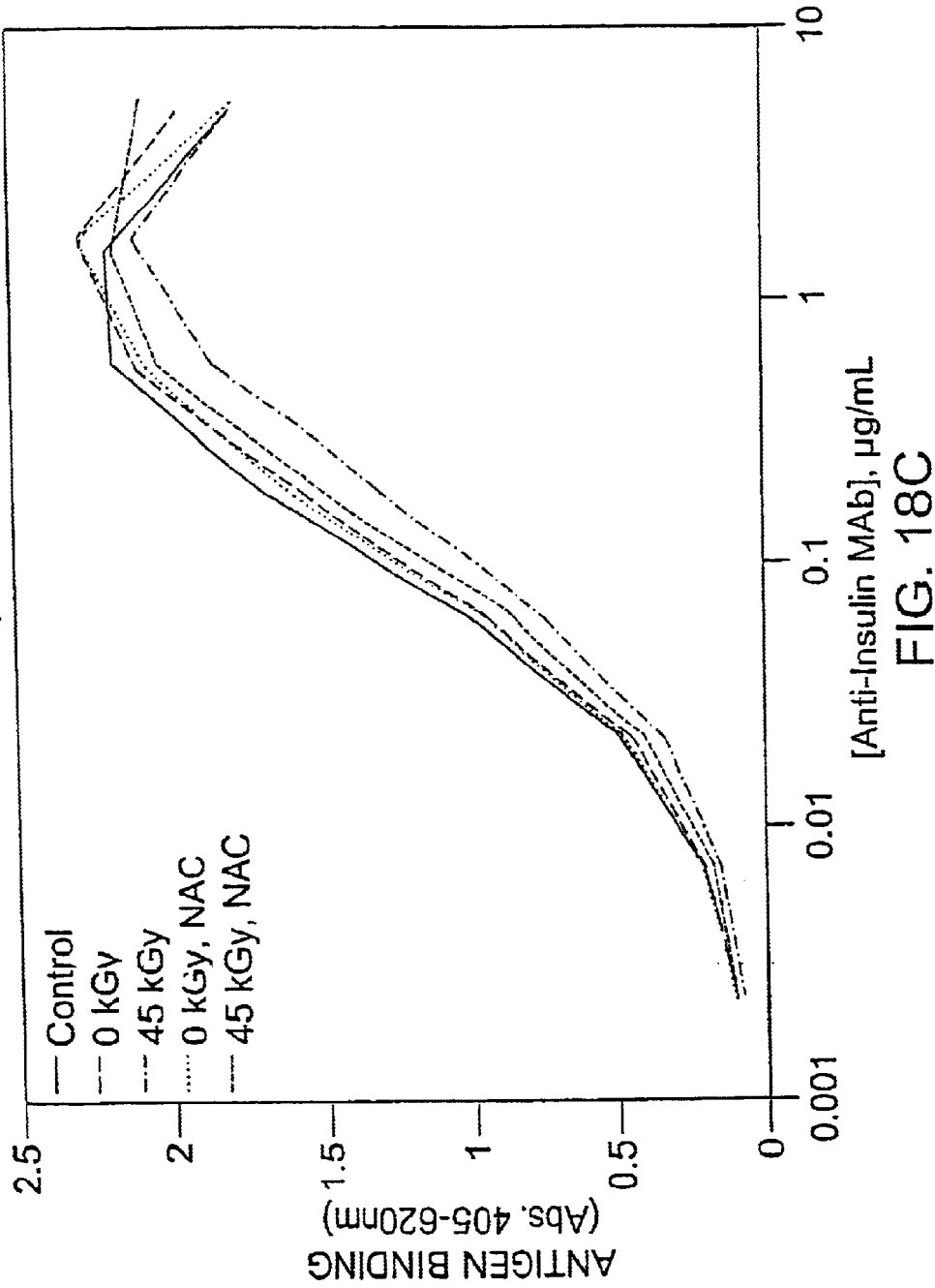

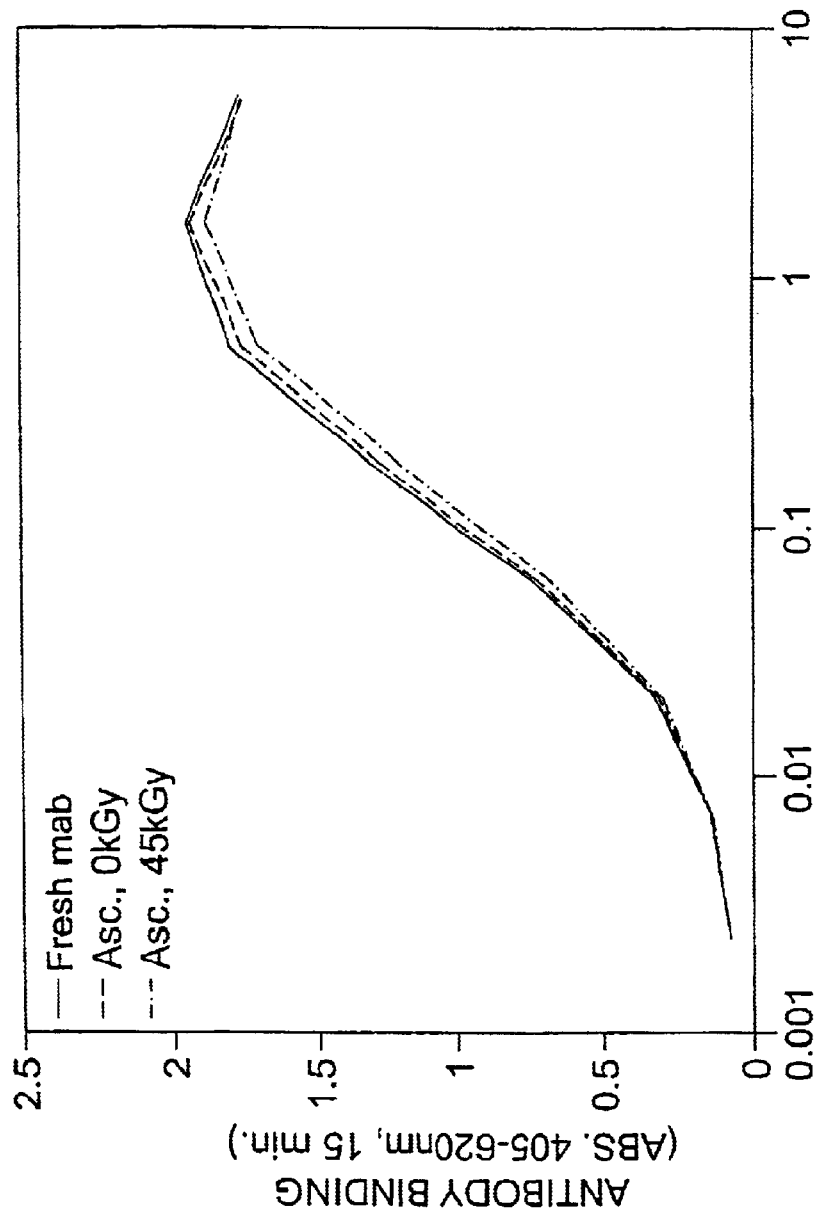

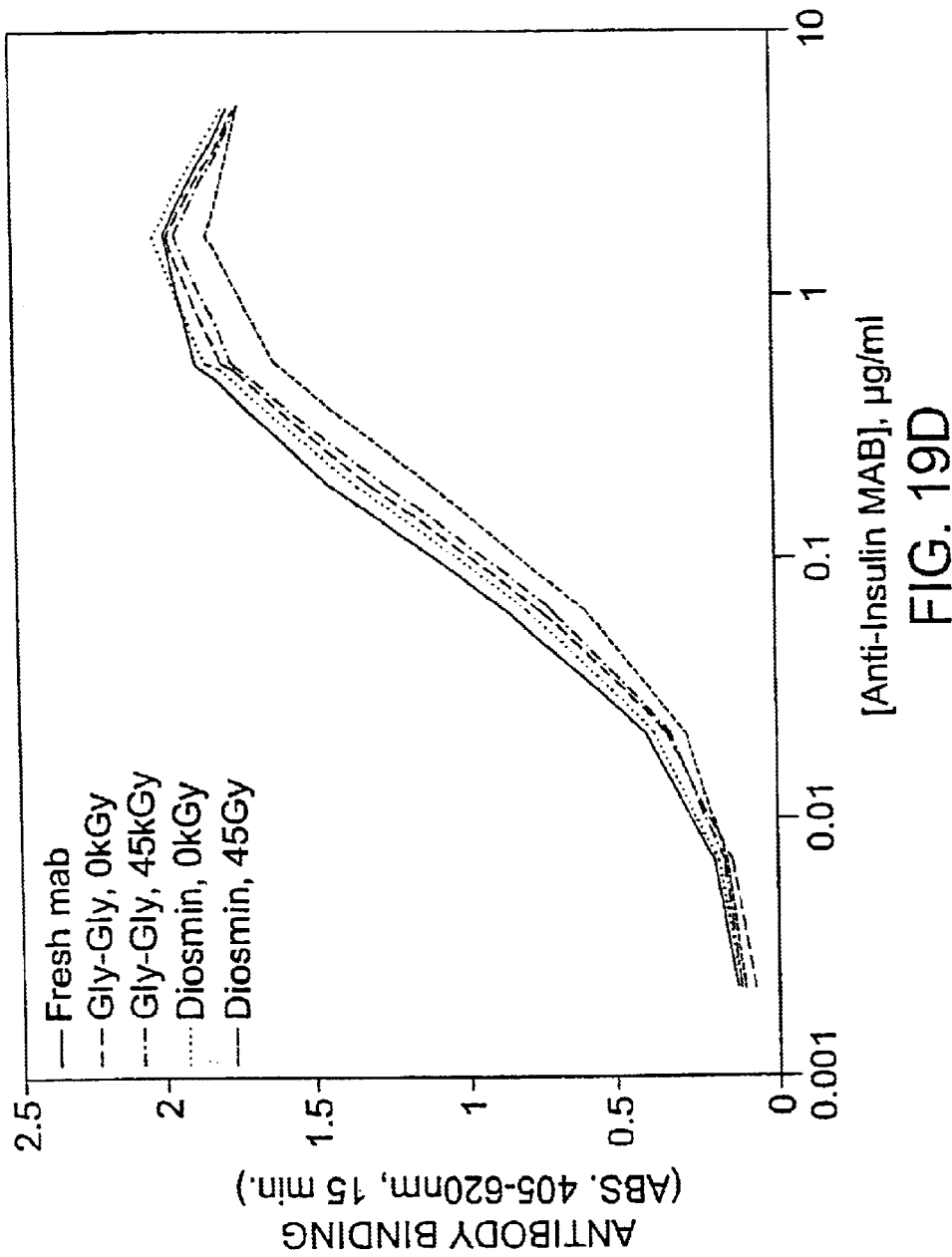

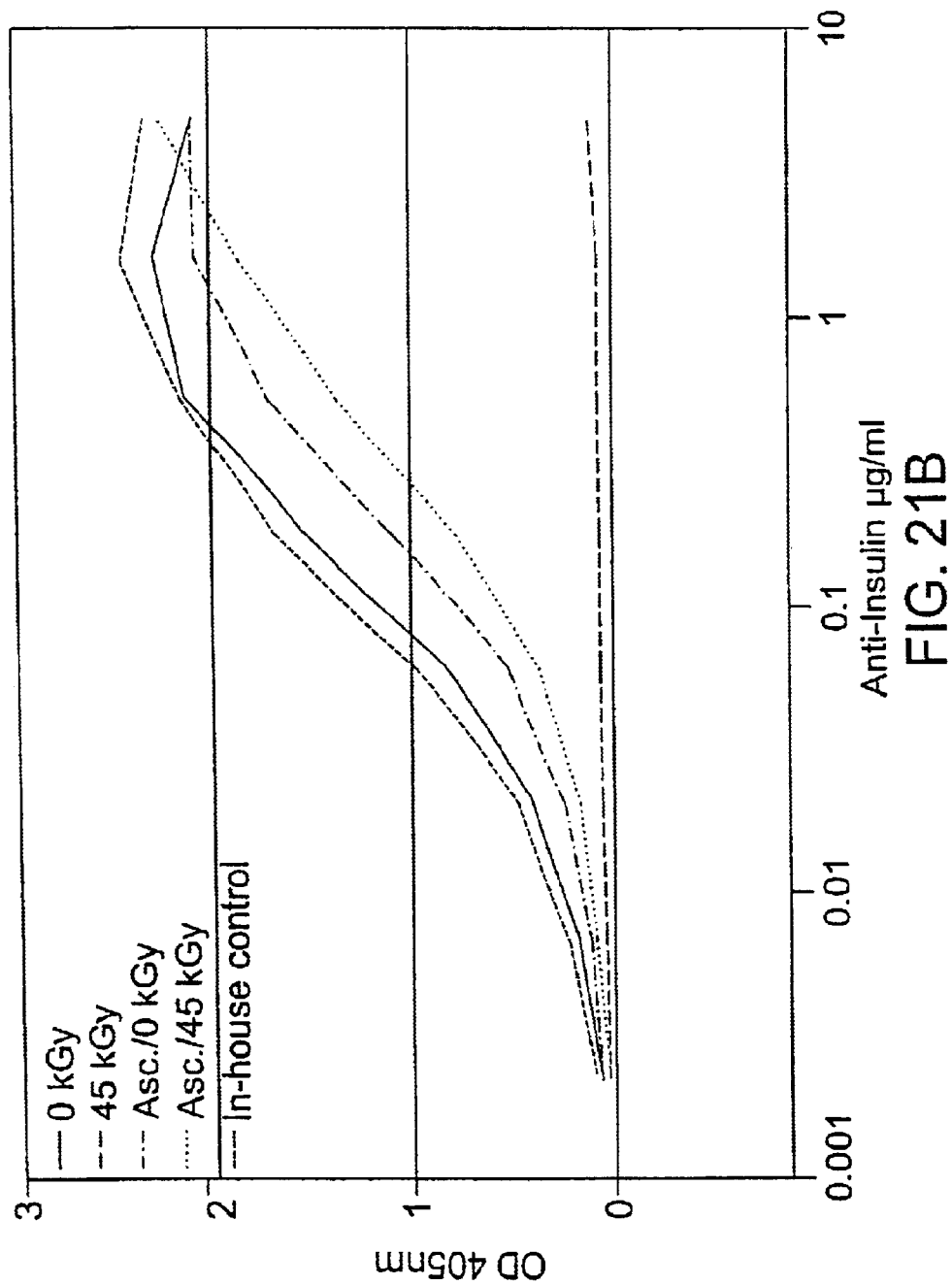

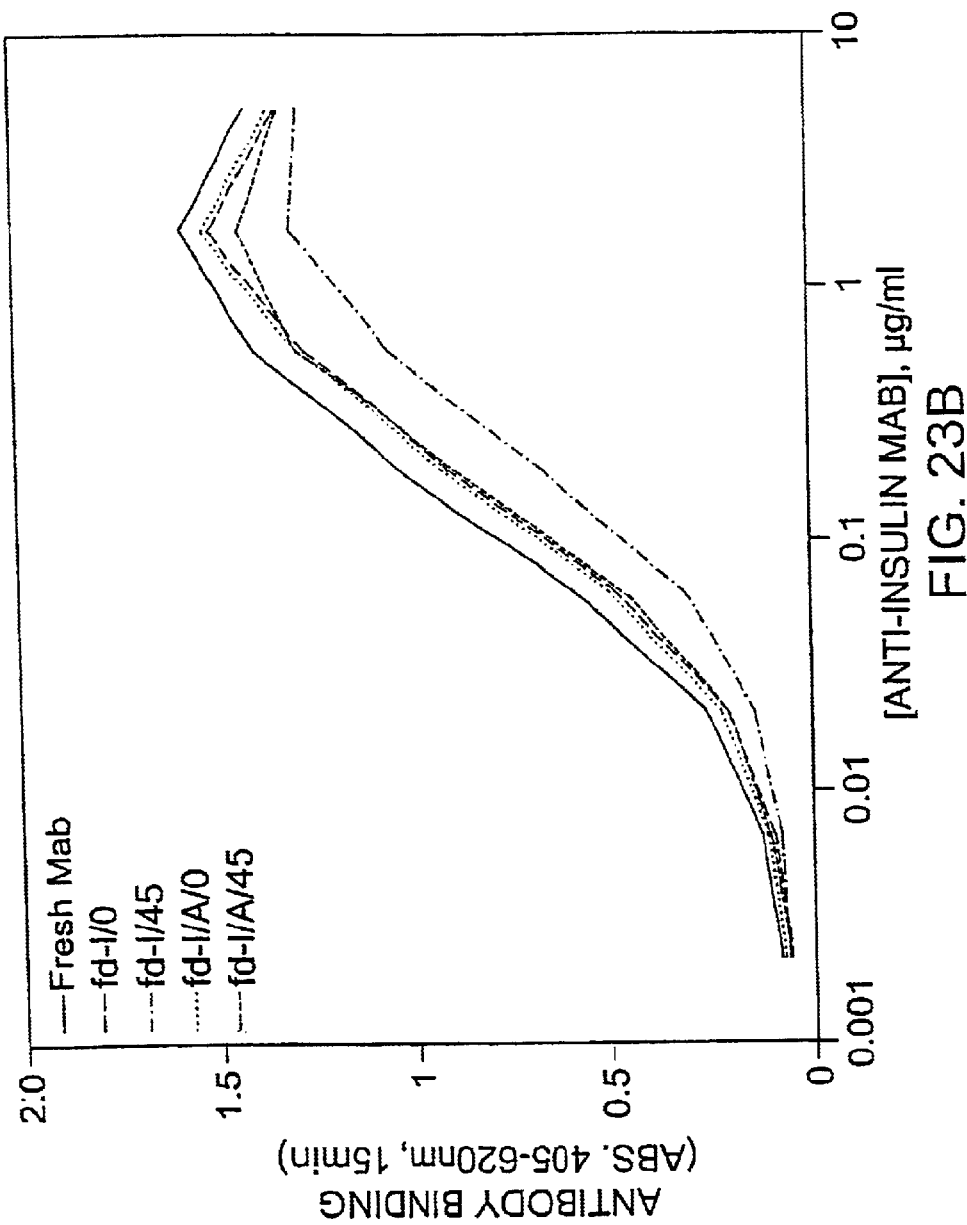

METHODS FOR STERILIZING PREPARATIONS OF MONOCLONAL IMMUNOGLOBULINS

FIELD OF THE INVENTION

The present invention relates to methods for sterilizing preparations of monoclonal immunoglobulins to reduce the level of active biological contaminants therein, such as viruses, bacteria, yeasts, molds, mycoplasmas, prions and/or parasites.

BACKGROUND OF THE INVENTION

Antibodies are produced by organisms in response to exposure to foreign substances that the body perceives as a threat. Antibodies, or as they are collectively known, immunoglobulins (Ig), are proteins secreted by cells of the immune system known as B-cells or plasma cells. The structure of immunoglobulins is complex, but is well characterized. In brief, each immunoglobulin consists of a complex of protein chains known as the heavy and light chains. Each heavy chain is linked to a single light chain via disulfide bonds. The resulting complex is in turn linked by additional disulfide bonds to an identical heavy-light chain complex. This basic unit can be assembled by the cell into several specialized forms by varying the structure and number of heavy chains. Different heavy chain structures produce differing molecules, known as "classes" of immunoglobulins. These classes may also have different numbers of the basic units described above.

The production of these various physical forms of the immunoglobulin molecule occurs in a sequential manner. During this process, the specificity of the molecule for a single molecule or antigen remains unchanged. This is because the changes described above all occur to the portion of the immunoglobulin molecule that is not involved in determining the specificity of the particular immunoglobulin molecule. This "hypervariable region" is subject to an unusually high degree of recombination events during B-cell maturation. These recombination events cease prior to the production of the first immunoglobulin molecule by the cell. The result is that from a relatively small number of variable region genes, the body generates a large number of potential immunoglobulin molecules of differing specificities.

Once a B-cell encounters a molecule to which its own immunoglobulin molecule binds (an "antigen"), and upon receiving signals from other cells in the immune system, the B-cell first multiplies into a large number of identical cells, (collectively referred to as a clone) and then differentiates into an immunoglobulin-secreting plasma cell. In this way, the extremely large number of potential immunoglobulin molecules that might be manufactured is limited to only those molecules that recognize antigens to which the body must respond.

The vast array of immunoglobulin specificities that are produced results in an ongoing protection for the body against infection from those organisms that the body has made immunoglobulins against in the past. Taken in sum, the result is that the immunoglobulins contained in the plasma from a single donor may have millions of useful immunoglobulin specificities. A preparation of immunoglobulins from plasma is thus referred to as a polyclonal immunoglobulin preparation, since it contains the immunoglobulin molecules produced by all of the plasma cell clones in the body.

Polyclonal immunoglobulins are particularly useful for treating human disease in which the ability to produce Ig is absent or impaired. Since all plasma cell clones are affected, a mixture of all the immunoglobulin specificities found in the plasma is needed to correct the deficiency. In contrast, when an extreme degree of specificity is required, or when a single defined therapeutic goal is sought, polyclonal immunoglobulins are not the best solution. Instead, an immunoglobulin preparation consisting of the immunoglobulin molecules produced by a single clone with the desired specificity is the most precise and predictable solution. Such a preparation is known as a monoclonal immunoglobulin.

Monoclonal immunoglobulin have many differences as compared to polyclonal immunoglobulins. Their monospecificity makes them very precise when used as detection reagents. As therapeutics, they are free of confounding or dangerous side effects that arise from polyclonal immunoglobulin preparations, such as the introduction of immunoglobulins of unwanted specificities being introduced into the patient. Their physical characteristics may also be different. Since each monoclonal immunoglobulin has a unique and unvarying structure, its potential for stability, degradation, aggregation, temperature sensitivity and other characteristics are unique and unchanging. Once a suitable monoclonal immunoglobulin has been chosen for production, its characteristics will not change, and it thus can be manufactured with great consistency and assurance of its performance and storage characteristics. The ability to tailor production volumes to product requirements also makes monoclonal immunoglobulin a highly desirable alternative to polyclonal immunoglobulins.

Monoclonal immunoglobulin preparations are made in one of three general fashions. The first involves production in a cell culture system, the second uses an animal as a temporary bioreactor for monoclonal immunoglobulin production, and the third involves inserting the gene for a desired monoclonal immunoglobulin into an animal in such a manner as to induce continuous production of the monoclonal immunoglobulin into a fluid or tissue of the animal so that it can be continuously harvested (transgenic production).

Each of these methods may result in contamination of the product by pathogens. In the first method, the cells producing the monoclonal immunoglobulin may harbour undetected viruses that can be produced in the culture system. Contamination of the culture system by bacteria, yeast or mold may also occur.

Both of the remaining methods involve the use of an animal to either serve as a host for the monoclonal immunoglobulin-producing cells or as a bioreactor to manufacture the monoclonal immunoglobulin product itself. Obviously, these products face the risk of contamination by pathogens infecting or harboured by the host animal. Such pathogens include, viruses, bacteria, yeasts, molds, mycoplasmas, and parasites, among others.

Consequently, it is of utmost importance that any biologically active contaminant in the monoclonal immunoglobulin product be inactivated before the product is used. This is especially critical when the product is to be administered directly to a patient. This is also critical for various monoclonal immunoglobulin products which are prepared in media which contain various types of plasma and which may be subject to mycoplasma or other viral contaminants.

Previously, most procedures have involved methods that screen or test products for a particular contaminant rather than removal or inactivation of the contaminant from the product. Products that test positive for a contaminant are merely not used. Examples of screening procedures include the testing for a particular virus in human blood from blood donors. Such procedures, however, are not always reliable and are not able to detect the presence of viruses in very low numbers. This reduces the value or certainty of the test in view of the consequences associated with a false negative result. False negative results can be life threatening in certain cases, for example in the case of Acquired Immune Deficiency Syndrome (AIDS). Furthermore, in some instances it can take weeks, if not months, to determine whether or not the product is contaminated.

In conducting experiments to determine the ability of technologies to inactivate viruses, the actual viruses of concern are seldom utilized. This is a result of safety concerns for the workers conducting the tests, and the difficulty and expense associated with the containment facilities and waste disposal. In their place, model viruses of the same family and class are used.

In general, it is acknowledged that the most difficult viruses to inactivate are those with an outer shell made up of proteins, and that among these, the most difficult to inactivate are those of the smallest size. This has been shown to be true for gamma irradiation and most other forms of radiation as these viruses diminutive size is a consequence of their small genome. The magnitude of direct effects of radiation upon a molecule are directly proportional to the size of the molecule, that is the larger the target molecule, the greater the effect. As a corollary, it has been shown for gamma-irradiation that the smaller the viral genome, the higher the radiation dose required to inactive it.

Among the viruses of concern for both human and animal-derived biologics, the smallest viruses of concern belong to the family of Parvoviruses and the slightly larger protein-coated Hepatitis virus. In humans, the Parvovirus B19, and Hepatitis A are the agents of concern. In porcine-derived products and tissues, the smallest corresponding virus is Porcine Parvovirus. Since this virus is harmless to humans, it is frequently chosen as a model virus for the human B19 Parvovirus and Hepatitis A. The demonstration of inactivation of this model parvovirus is considered adequate proof that the method employed will kill human B19 virus and Hepatitis A, and by extension, that it will also kill the larger and less hardy viruses such as HIV, CMV, Hepatitis B and C and others.

More recent efforts have focused on methods to remove or inactivate contaminants in the products. Such methods include heat treating, filtration and the addition of chemical inactivants or sensitizers to the product. Heat treatment requires that the product be heated to approximately 60° C. for about 70 hours which can be damaging to sensitive products. Heat inactivation can destroy 50% or more of the biological activity of the product. Filtration involves filtering the product in order to physically remove contaminants. Unfortunately this method may also remove products that have a high molecular weight. Further, in certain cases small viruses may not be removed by the filter because of the larger molecular structure of the product. The procedure of chemical sensitization involves the addition of noxious agents which bind to the DNA/RNA of the virus and which are activated either by UV or radiation to produce reactive intermediates and/or free radicals which bind to the DNA/RNA or break the chemical bonds in the backbone of the DNA/RNA of the virus or crosslink or complex it in such a way that the virus can no longer replicate. This procedure requires that unbound sensitizer is washed from products since the sensitizers are toxic, if not mutagenic or carcinogenic, and can not be administered to a patient.

Irradiating a product with gamma radiation is another method of sterilizing a product. Gamma radiation is effective in destroying viruses and bacteria when given in high total doses (Keathly et al., "Is There Life After Irradiation? Part 2," BioPharm July-August, 1993, and Leitman, Use of Blood Cell Irradiation in the Prevention of Post Transfusion Graft-vs-Host Disease," Transfusion Science 10:219–239 (1989)). The published literature in this area, however, teaches that gamma radiation can be damaging to radiation sensitive products, such as blood, blood products, protein and protein-containing products. In particular, it has been shown that high radiation doses are injurious to red cells, platelets and granulocytes (Leitman). U.S. Pat. No. 4,620,908 discloses that protein products must be frozen prior to irradiation in order to maintain the viability of the protein product. This patent concludes that "[i]f the gamma irradiation were applied while the protein material was at, for example, ambient temperature, the material would be also completely destroyed, that is the activity of the material would be rendered so low as to be virtually ineffective". This would apply as well to monoclonal immunoglobulins which are, of course, proteins. Unfortunately, many sensitive biologicals, such as monoclonal antibodies (Mab), would lose viability and activity if subjected to freezing for irradiation purposes and then thawing prior to administration to a patient.

In view of the difficulties discussed above, there remains a need for methods of sterilizing monoclonal immunoglobulins that are effective for reducing the level of active biological contaminants without an adverse effect on the monoclonal immunoglobulins.

SUMMARY OF THE INVENTION

Accordingly, it is an object of the present invention to provide methods of sterilizing preparations of monoclonal immunoglobulins by reducing the level of active biological contaminants without adversely affecting the monoclonal immunoglobulins. Other objects, features and advantages of the present invention will be set forth in the detailed description of preferred embodiments that follows, and in part will be apparent from the description or may be learned by practice of the invention. These objects and advantages of the invention will be realized and attained by the compositions and methods particularly pointed out in the written description and claims hereof.

In accordance with these and other objects, a first embodiment of the present invention is directed to a method for sterilizing a preparation of monoclonal immunoglobulins that is sensitive to radiation comprising: (i) reducing the residual solvent content of a preparation of monoclonal immunoglobulins to a level effective to protect the preparation of monoclonal immunoglobulins from radiation; and (ii) irradiating the preparation of monoclonal immunoglobulins with radiation at an effective rate for a time effective to sterilize the preparation of monoclonal immunoglobulins.

A second embodiment of the present invention is directed to a method for sterilizing a preparation of monoclonal immunoglobulins that is sensitive to radiation comprising: (i) adding to a preparation of monoclonal immunoglobulins at least one stabilizer in an amount effective to protect the preparation of monoclonal immunoglobulins from radiation; and (ii) irradiating the preparation of monoclonal immunoglobulins with radiation at an effective rate for a time effective to sterilize the preparation of monoclonal immunoglobulins.

A third embodiment of the present invention is directed to a method for sterilizing a preparation of monoclonal immunoglobulins that is sensitive to radiation comprising: (i)

reducing the residual solvent content of a preparation of monoclonal immunoglobulins to a level effective to protect the preparation of monoclonal immunoglobulins from radiation; (ii) adding to the preparation of monoclonal immunoglobulins at least one stabilizer in an amount effective to protect the preparation of monoclonal immunoglobulins from radiation; and (iii) irradiating the preparation of monoclonal immunoglobulins with radiation at an effective rate for a time effective to sterilize the preparation of monoclonal immunoglobulins. According to this embodiment, steps (i) and (ii) may be reversed.

The invention also provides a composition comprising at least one monoclonal immunoglobulin and a least one stabilizer selected from the group consisting of: ascorbic acid or a salt or ester thereof; glutathione; 6-hydroxy-2,5,7,8-tetramethylchroman-2-carboxylic acid; uric acid or a salt or ester thereof; methionine; histidine; N-acetyl cysteine; the dipeptide glycine-glycine; diosmin; silymarin; a mixture of ascorbic acid, or a salt or ester thereof, and uric acid, or a salt or ester thereof; a mixture of ascorbic acid, or a salt or ester thereof, and 6-hydroxy-2,5,7,8-tetramethylchroman-2-carboxylic acid; a mixture of ascorbic acid, or a salt or ester thereof, uric acid, or a salt or ester thereof, and 6-hydroxy-2,5,7,8-tetramethylchroman-2-carboxylic acid; and a mixture of uric acid, or a salt or ester thereof and 6-hydroxy-2,5,7,8-tetramethylchroman-2-carboxylic acid, said at least one stabilizer being present in an amount effective to preserve said monoclonal immunoglobulin for its intended use following sterilization of the composition with radiation.

BRIEF DESCRIPTION OF THE DRAWINGS

FIGS. 1 and 2 are graphs showing the protective effects of certain stabilizers on lyophilized anti-insulin monoclonal immunoglobulin exposed to 45 kGy of low dose gamma irradiation.

FIGS. 3A–3C are graphs showing the protective effects of certain stabilizers on lyophilized anti-insulin monoclonal immunoglobulin exposed to 45 kGy of low dose gamma irradiation.

FIGS. 16A, 16B, 17A, and 17B are graphs showing the effect of ascorbate at varying concentrations on immobilized anti-insulin monoclonal immunoglobulin after irradiation with gamma radiation.

FIGS. 18A–18H are graphs showing the effect of stabilizers on lyophilized anti-insulin monoclonal immunoglobulin supplemented with human serum albumin or sucrose, after irradiation with gamma radiation.

FIGS. 19A–19F are graphs showing the effect of stabilizers on lyophilized anti-insulin monoclonal immunoglobulin supplemented with bovine serum albumin, after irradiation with gamma radiation.

FIGS. 21A and 21B are graphs showing the effect of low pH (4.5) on the stabilizing effect of L-ascorbic acid on monoclonal immunoglobulin irradiated to 45 kGy with gamma radiation.

FIGS. 23A and 23B are graphs showing the effect of the presence or absence of sodium ascorbate on the level of activity retention achieved when irradiating monoclonal immunoglobulins in both liquid and lyophilized forms with e-beam radiation.

DETAILED DESCRIPTION OF THE PREFERRED EMBODIMENTS

A. Definitions

Figure 1:
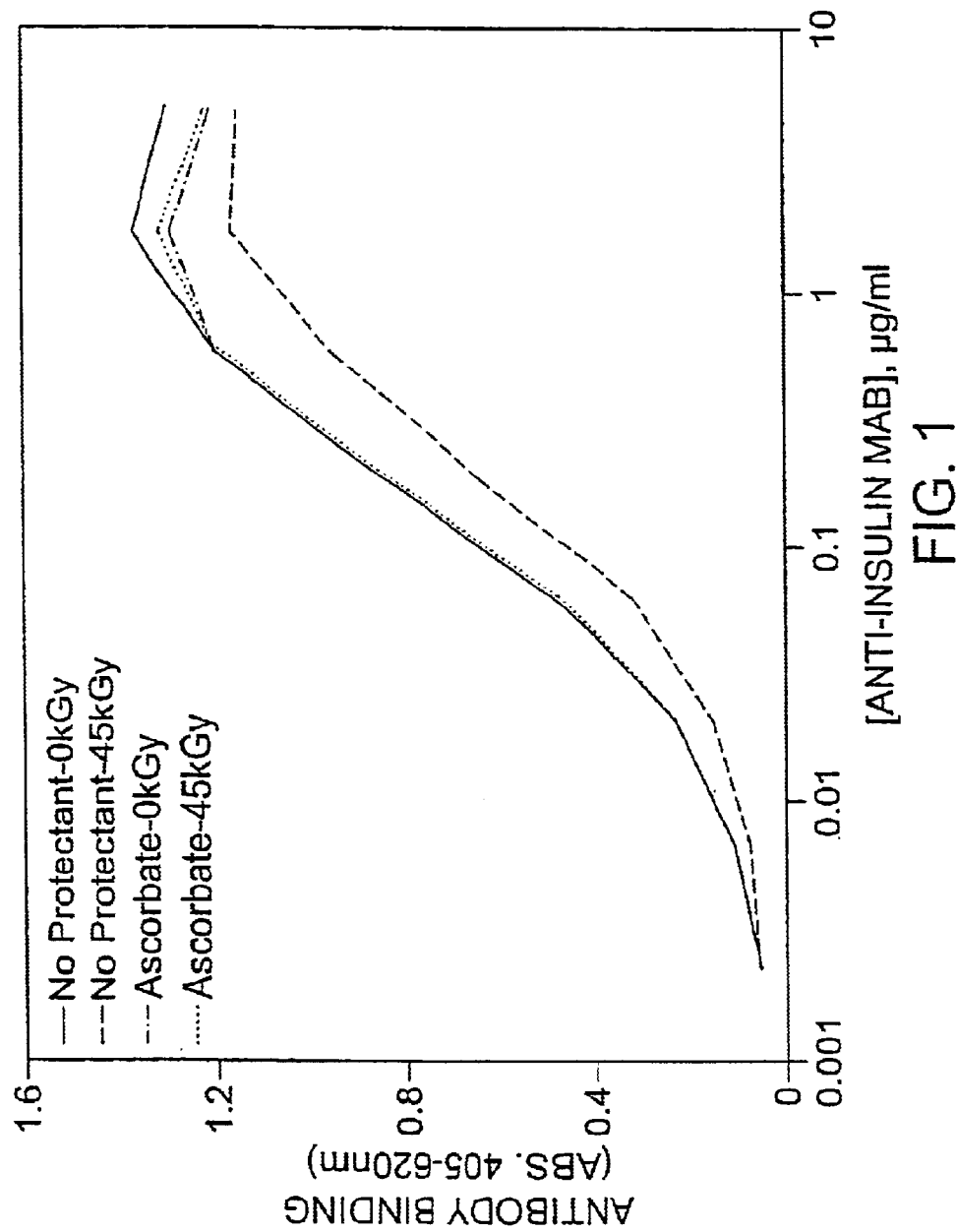

Unless defined otherwise, all technical and scientific terms used herein are intended to have the same meaning as is commonly understood by one of ordinary skill in the relevant art. All patents and publications mentioned herein are expressly incorporated by reference.

As used herein, the singular forms "a," "an," and "the" include the plural reference unless the context clearly dictates otherwise.

As used herein, the term "immunoglobulin" is used synonymously with the term "antibody", and encompasses all classes of immunoglobulins including, without limitation, IgG, IgM, IgA, IgD and IgE and all subclasses of immunoglobulins such as the IgG subclasses IgG1, IgG2, IgG3, and IgG4 found in or produced by cells or animals including humans. The term "immunoglobulin" encompasses both membrane immunoglobulins and secreted immunoglobulins. Membrane immunoglobulins are transmembrane proteins of B cells, and act as the B cells' antigen receptor. Secreted immunoglobulins are structurally identical to their membrane counterparts except that they lack the transmembrane region of amino acids at the C-terminus of membrane immunoglobulins. Secreted immunoglobulins are present in extracellular fluids and secretions.

The term "immunoglobulin" also encompasses fragments of immunoglobulins including, without limitation, fragments F(ab')$_2$, Fab', Fab, Fc, Facb, pFc', and Fd, as well as immunoglobulin derivatives and metabolites as are known in the art. Metabolites of immunoglobulin are products resulting from the metabolism of immunoglobulins by a living organism. A wide variety of derivatives of immunoglobulins as are known in the art may be prepared by known methods, which typically involve breaking peptide or disulfide bonds in the immunoglobulin. Immunoglobulins may also be derivatized to include modified or synthetic or unnatural amino acids. Derivatives of immunoglobulins also include immunoglobulins conjugated to a moiety such as a toxin (e.g. diphtheria toxin, ricin), a labelling molecule (e.g. fluorescin, Texas Red), a radioactive atom or molecule (e.g. $^{125}$I) for therapeutic or diagnostic use, an enzyme (e.g. avidin, horseradish peroxidase, alkaline phosphatase), et cetera. Immunoglobulins may include post-translational modifications such as phosphorylation, glyocsylation, myristilation, prenylation, ADP-ribosylation, methylation, acetylation, hydroxylation, carboxylation, and oxidation-reduction, or may be cationized or anionized to alter the overall charge of the immunoglobulin.

The term "monoclonal immunoglobulins" refers to homogeneous immunoglobulins produced by a single clone, and are to be contrasted with polyclonal immunoglobulins. Monoclonal immunoglobulins are usually made from hybridomas, which are prepared by fusing immunized mouse or rat spleen cells with a non-secretor myeloma using polyethylene glycol (PEG). The fusion mixture is plated out in HAT medium, containing hypoxanthine, aminopterin and thymidine. Aminopterin blocks a metabolic pathway which can be bypassed if hypoxanthine and thymidine are present. The myeloma cells lack this bypass and consequently die in the HAT medium. Spleen cells die naturally in culture after one or two weeks, but fused cells survive because they have the immortality of the myeloma and the metabolic bypass of the spleen cells. Some of the fused cells secrete antibody, and the supernatants are tested in a specific assay. Wells which produce the desired antibody are then cloned. Monoclonal immunoglobulins may also be produced by various techniques familiar to one skilled in the art of genetic engineering that cause the inducible or constitutive expression of a single set of endogenous genes that code for a single immunoglobulin, or that involve the addition of such a set or portion of a set, of genes into a cell or organism in such a manner as to result in either the inducible or constitutive expression of the resulting single set of genes that code for a single immunoglobulin.

Monoclonal immunoglobulins may be produced using the above-described techniques in combination with in vitro cell culture, in vivo cell culture (for example as an ascites culture) or by the techniques of transgenesis. Transgenesis involves the insertion of one or more genes into a recipient organism. The recipient organism then produces the protein product of these genes, either constitutively or following induction, and either incorporates them or secretes the into a tissue (including eggs) or fluid (including blood, sweat, milk or urine). The resulting tissue or fluid is then harvested and the desired monoclonal immunoglobulin is purified from it.

As used herein, the term "preparation of monoclonal immunoglobulins" encompasses, without limitation: (1) compositions consisting solely of monoclonal immunoglobulins (such as monoclonal immunoglobulins of a single specificity or combinations of monoclonal immunoglobulins of different specificities and/or different classes) and which may contain impurities (including the naturally-occuring components of a tissue or fluid into which the monoclonal antibody was produced by transgenic means); (2) compositions comprising monoclonal immunoglobulins, pharmaceutically acceptable diluents, carriers, adjuvants, liposomes and other therapeutic agents, et cetera, as are known in the art; (3) partially-purified in-process intermediate preparations of monoclonal immunoglobulins; and (4) articles containing monoclonal immunoglobulins or having monoclonal immunoglobulins immobilized upon them or otherwise disposed thereon. Preferred "preparations of monoclonal immunoglobulins" are discussed below.

In therapeutic applications, monoclonal immunoglobulins are typically combined with buffer or salt solutions as are known in the art. The monoclonal immunoglobulin may also be combined with another therapeutic agent. For instance, anti-platelet monoclonal immunoglobulins which prevent platelets from aggregating are being evaluated for long-term therapy for the prevention of formation of thrombi. In this application, the anti-platelet monoclonal immunoglobulin is administered together with aspirin. The monoclonal immunoglobulin and the other therapeutic agent may be co-packaged for administration by, for example, intravenous injection. This may take the form of simple inclusion into a single external package, or they may be provided in a single container. An example of a more advanced form of packaging would be the use of monoclonal immunoglobulins in liposome preparations. Typically, the immunoglobulin is embedded in at least the outer layer of the liposome where it can act as a targeting agent by binding to structures on or in the desired cells or tissues. The drug, which is contained within the liposome, is then released at this specific site, providing a more concentrated drug therapy with a larger therapeutic index than achievable by ordinary systemic therapy.

For therapeutic use, the monoclonal immunoglobulins are typically provided in liquid, frozen, or freeze-dried (lyophilized) form packaged under nitrogen or vacuum. The monoclonal immunoglobulins are usually then reconstituted with sterile water (if required, or thawed as needed) and administered by an appropriate route, such as an intramuscular injection or intravenous injection either directly or following placement in an IV bag. In accordance with the invention, the preparation of monoclonal immunoglobulins may be irradiated at any stage, including but not limited to as a raw material, a purified or partially-purified in-process intermediate, in bulk or in individual or multi-dose packaging, before or after packaging, after dilution for administration, or in the IV bag or other delivery vehicle itself. The irradiation may be carried out at any convenient temperature that does not have a deleterious effect upon the preparation, and which may be above or below the freezing or eutectic point of the preparation. Various preparations of monoclonal immunoglobulins are available for therapeutic use, as set forth in Table 1.

TABLE 1

Therapeutic Monoclonal Immunoglobulin Products

| Name | mAb Name | Target | Indication | Company | Status | Physical State* |
|---|---|---|---|---|---|---|
| Herceptin | Trastuzumab | Anti-HER2 | Metastatic Breast Cancer | Genentech, | Licensed | FD |
| Rituxan | Rituximab | Anti-CD20 | B Cell non-Hodgkin's | Genentech, | | L |
| Xolair | Omalizumab | Anti-IgE | asthma | Genetech, | Clinical Trials | FD |
| | Anti-VEGF | Anti-VEGF | Relapsed Metastatic Breast Cancer | Genetech, | Clinical Trials | |
| Xanelim | Anti-CD11a | Anti- | Severe | Genetech, | Clinical | FD |

TABLE 1-continued

Therapeutic Monoclonal Immunoglobulin Products

| Name | mAb Name | Target | Indication | Company | Status | Physical State* |
|---|---|---|---|---|---|---|
| LDP-02 | Anti-a4b7 | CD11a Anti-a4b7 | Psoriasis IBD | Genetech, | Trials Clinical Trials | FD |
| Anti-HER2 2C4 | | | Solid Tumors | Genetech, | Clinical Trials | |
| Remicade | Infliximab | cA2 | Crohn's Disease | Centacor | Clinical Trials | FD |
| Gleevec | | | CML | Novartis | | C |
| Campath | Alemtuzu | | CLL | Berlex/ Millennium | | |

Source for above Table: A practical guide to ELISA, D. M. Kemeny, Pergamon Press
*FD - Freeze-Dried (Lyophylized), L - Liquid, I - Immobilized on a surface, C - Capsule (Oral Dosing) containing dried material Preparations of monoclonal immunoglobulins also find application as research tools and a vast number are used for diagnostic purposes, particularly in blood work. Typical research tools and diagnostic tests involving monoclonal immunoglobulins include enzyme-linked immunosorbent assays (ELISA), radioimmunoassays (RIA), magnetic-bead-based assays and separation kits, and fluorescent activated cell analysis and/or sorting, among others. It is desirable to sterilize such diagnostic tools, both to preserve them, as well as for safety, as they are handled by lab technicians. Preparations of monoclonal immunoglobulins used for diagnostic purposes often comprise a solid support, such as a dipstick or plastic plate, having the monoclonal immunoglobulins immobilized on or in it by covalent chemistry, drying, or other known means. In accordance with the invention, an entire commercial package or kit, containing the solid support with monoclonal immunoglobulins affixed thereto, instructions, containers of reagents (for instance a reference sample for generating a standard curve), et cetera, may be sterilized in accordance with the invention. Table 2 sets forth a number of commercial diagnostic monoclonal immunoglobulin products.

TABLE 2

Diagnostic Monoclonal Immunoglobulin Products

| Name | mAb Name | Target | Indication | Company | Status | Physical State* |
|---|---|---|---|---|---|---|
| CMV IgG | | | ELISA | | Sigma | FD |
| CMV IgM | | | ELISA | | Sigma | FD |
| HSV Type 1 and 2 (IgG) | | | ELISA | | Sigma | FD/L |
| Rubella IgG (Indirect | | | ELISA | | Sigma | FD/L |
| Rubella IgG (Capture) | | | ELISA | | Sigma | FD |
| Lyme Disease (Indirect | | | ELISA | | Sigma | FD |
| Mumps (Indirect) | | | ELISA | | Sigma | FD |
| Pregnancy Test Kits | | | | | J & J | I |
| FACS analysis (diagnostic imaging) | | | | | BD, Coulter | FD/L |

Sources for above Table: A practical guide to ELISA, D. M. Kemeny, Pergamon Press
*FD - Freeze-Dried (Lyophylized), L - Liquid, I - Immobilized on a surface, C - Capsule (Oral Dosing) containing dried material As used herein, the term "sterilize" is intended to mean a reduction in the level of at least one active biological contaminant found in the preparation of monoclonal immunoglobulins being treated according to the present invention.

As used herein, the term "biological contaminant" is intended to mean a contaminant that, upon direct or indirect contact with a preparation of monoclonal immunoglobulins, may have a deleterious effect on a preparation of monoclonal immunoglobulins or upon a recipient thereof. Such biological contaminants include the various viruses, bacteria and parasites known to those of skill in the art to generally be found in or infect preparation of monoclonal immunoglobulins. Examples of biological contaminants include, but are not limited to, the following: viruses, such as human immuno-deficiency viruses and other retroviruses, herpes viruses, parvoviruses, filoviruses, circoviruses, paramyxoviruses, cytomegaloviruses, hepatitis viruses (including hepatitis B and hepatitis C), pox viruses, toga viruses, Epstein-Barr virus and parvoviruses; bacteria, such as Escherichia, Bacillus, Campylobacter, Streptococcus and Staphylococcus; parasites, such as Trypanosoma and malarial parasites, including Plasmodium species; yeasts; molds; mycoplasmas; and prions. As used herein, the term "active biological contaminant" is intended to mean a biological contaminant that is capable of causing the deleterious effect.

As used herein, the term "a biologically compatible solution" is intended to mean a solution to which monoclonal immunoglobulins may be exposed, such as by being suspended or dissolved therein, and remain viable, i.e., retain their essential biological and physiological characteristics.

As used herein, the term "a biologically compatible buffered solution" is intended to mean a biologically compatible solution having a pH and osmotic properties (e.g., tonicity, osmolality and/or oncotic pressure) suitable for maintaining the integrity of monoclonal immunoglobulins. Suitable biologically compatible buffered solutions typically have a pH between 4 and 8.5 and are isotonic or only moderately hypotonic or hypertonic. Biologically compatible buffered solutions are known and readily available to those of skill in the art.

As used herein, the term "stabilizer" is intended to mean a compound or material that reduces any damage to the preparation of monoclonal immunoglobulins being irradiated to a level that is insufficient to preclude the safe and effective use of the preparation of monoclonal immunoglobulins. Illustrative examples of stabilizers include, but are not limited to, the following: antioxidants, such as ascorbic acid and tocopherol; and free radical scavengers, such as ethanol. Preferred examples of stabilizers include, but are not limited to, the following: fatty acids, including 6,8-dimercapto-octanoic acid (lipoic acid) and its derivatives and analogues (alpha, beta, dihydro, bisno and tetranor lipoic acid), thioctic acid, 6,8-dimercapto-octanoic acid, dihydrolopoate (DL-6,8-dithioloctanoic acid methyl ester), lipoamide, bisonor methyl ester and tatranor-dihydrolipoic acid, furan fatty acids, oleic and linoleic and palmitic acids and their salts and derivatives; flavonoids, phenylpropaniods, and flavenols, such as quercetin, rutin and its derivatives, apigenin, aminoflavone, catechin, hesperidin and, naringin; carotenes, including beta-carotene; Co-Q10; xanthophylls; polyhydric alcohols, such as glycerol, mannitol; sugars, such as xylose, glucose, ribose, mannose, fructose and trehalose; amino acids, such as histidine, N-acetylcysteine (NAC), glutamic acid, tryptophan, sodium carpryl N-acetyl tryptophan and methionine; azides, such as sodium azide; enzymes, such as Superoxide Dismutase (SOD) and Catalase; uric acid and its derivatives, such as 1,3-dimethyluric acid and dimethylthiourea; allopurinol; thiols, such as glutathione and reduced glutathione and cysteine; trace elements, such as selenium; vitamins, such as vitamin A, vitamin C (including its derivatives and salts such as sodium ascorbate and palmitoyl ascorbic acid) and vitamin E (and its derivatives and salts such as tocopherol acetate and alpha-tocotrienol); chromanol-alpha-C6; 6-hydroxy-2,5,7,8-tetramethylchroma-2 carboxylic acid (Trolox) and derivatives; extraneous proteins, such as gelatin and albumin; tris-3-methyl-1-phenyl-2-pyrazolin-5-one (MCI-186); citiolone; puercetin; chrysin; dimethyl sulfoxide (DMSO); piperazine diethanesulfonic acid (PIPES); imidazole; methoxypsoralen (MOPS); 1,2-dithiane-4,5-diol; reducing substances, such as butylated hydroxyanisole (BHA) and butylated hydroxytoluene (BHT); cholesterol; probucol; indole derivatives; thimerosal; lazaroid and tirilazad mesylate; proanthenols; proanthocyanidins; ammonium sulfate; Pegorgotein (PEG-SOD); N-tert-butyl-alpha-phenylnitrone (PBN); 4-nydroxy-2,2,6,6-Tetramethylpiperidin-1-oxyl (Tempol); mixtures of ascorbate, urate and Trolox C (Asc/urate/Trolox C); proteins, peptides and dipeptides; the Glycine homodipeptide glycine-glycine (Gly-Gly); reduced glutathione; diosmin; pupurogalin; gallic acid and its derivatives including but not limited to propyl gallat;, sodium formaldehyde sulfoxylate and silymarin.

As used herein, the term "residual solvent content" is intended to mean the amount or proportion of freely-available liquid in the preparation of monoclonal immunoglobulins. Freely-available liquid means that liquid, such as water or an organic solvent (e.g. ethanol, isopropanol, polyethylene glycol, etc.), present in the preparation of monoclonal immunoglobulins that is not bound to or complexed with one or more of the non-liquid components of the preparation of monoclonal immunoglobulins. Freely-available liquid includes intracellular water. The residual solvent contents related as water referenced herein refer to levels determined by the FDA approved, modified Karl Fischer method (Meyer and Boyd, Analytical Chem., 31, 215–219, 1959; May, et al., J. Biol. Standardization, 10, 249–259, 1982; Centers for Biologics Evaluation and Research, FDA, Docket No. 89D-0140, 83–93; 1990). Quantitation of the residual levels of other solvents may be determined by means well known in the art, depending upon which solvent is employed. The proportion of residual solvent to solute may also be considered to be a reflection of the concentration of the solute within the solvent. When so expressed, the greater the concentration of the solute, the lower the amount of residual solvent.

As used herein, the term "sensitizer" is intended to mean a substance that selectively targets viral, bacterial, prion and/or parasitic contaminants, rendering them more sensitive to inactivation by radiation, therefore permitting the use of a lower rate or dose of radiation and/or a shorter time of irradiation than in the absence of the sensitizer. Illustrative examples of suitable sensitizers include, but are not limited to, the following: psoralen and its derivatives and analogs (including 3-carboethoxy psoralens); angelicins, khellins and coumarins which contain a halogen substituent and a water solubilization moiety, such as quaternary ammonium ion or phosphonium ion; nucleic acid binding compounds; brominated hematoporphyrin; phthalocyanines; purpurins; porphorins; halogenated or metal atom-substituted derivatives of dihematoporphyrin esters, hematoporphyrin derivatives, benzoporphyrin derivatives, hydrodibenzoporphyrin dimaleimade, hydrodibenzoporphyrin, dicyano disulfone, tetracarbethoxy hydrodibenzoporphyrin, and tetracarbethoxy hydrodibenzoporphyrin dipropionamide; doxorubicin and daunomycin, which may be modified with halogens or metal atoms; netropsin; BD peptide, S2 peptide; S-303 (ALE compound); dyes, such as hypericin, methylene blue, eosin, fluoresceins (and their derivatives), flavins, merocyanine 540; photoactive compounds, such as bergapten; and SE peptide.

As used herein, the term "radiation" is intended to mean radiation of sufficient energy to sterilize at least some component of the irradiated monoclonal immunoglobulins. Types of radiation include, but are not limited to, the following: (i) corpuscular (streams of subatomic particles such as neutrons, electrons, and/or protons); and (ii) electromagnetic (originating in a varying electromagnetic field, such as radio waves, visible (both mono and polychromatic) and invisible light, ultraviolet radiation, x-radiation, and gamma rays and mixtures thereof). Such radiation is often described as either ionizing (capable of producing ions in irradiated materials) radiation such as gamma rays and non-ionizing radiation such as visible light. The sources of such radiation may vary, however in general the specific source is of little material difference as long as sufficient radiation is given in an appropriate time and at an appropriate rate to effect sterilization. In practice, gamma radiation is usually produced by isotopes of Cobalt or Cesium, while X-rays are produced by machines that emit X-radiation, and electrons are often used to sterilize materials in a method known as "e-beam" irradiation that involves their production via a machine.

B. Particularly Preferred Embodiments

A first preferred embodiment of the present invention is directed to a method for sterilizing a preparation of monoclonal immunoglobulins that is sensitive to radiation comprising: (i) reducing the residual solvent content of the preparation of monoclonal immunoglobulins to a level effective to protect the preparation of monoclonal immunoglobulins from radiation; and (ii) irradiating the preparation of monoclonal immunoglobulins with radiation at an effective rate for a time effective to sterilize the preparation of monoclonal immunoglobulins.

A second embodiment of the present invention is directed to a method for sterilizing a preparation of monoclonal immunoglobulins that is sensitive to radiation comprising: (i) adding to a preparation of monoclonal immunoglobulins at least one stabilizer in an amount effective to protect the preparation of monoclonal immunoglobulins from radiation; and (ii) irradiating the preparation of monoclonal immunoglobulins with radiation at an effective rate for a time effective to sterilize the preparation of monoclonal immunoglobulins.

A third embodiment of the present invention is directed to a method for sterilizing a preparation of monoclonal immunoglobulins that is sensitive to radiation comprising: (i) reducing the residual solvent content of a preparation of monoclonal immunoglobulins to a level effective to protect the preparation of monoclonal immunoglobulins from radiation; (ii) adding to the preparation of monoclonal immunoglobulins at least one stabilizer in an amount effective to protect the preparation of monoclonal immunoglobulins from radiation; and (iii) irradiating the preparation of monoclonal immunoglobulins with radiation at an effective rate for a time effective to sterilize the preparation of monoclonal immunoglobulins. The order of steps (i) and (ii) may, of course, be reversed as desired.

According to the methods of the present invention, the residual solvent content of the preparation of monoclonal immunoglobulins may be reduced prior to irradiation of the preparation of monoclonal immunoglobulins with radiation. The residual solvent content is reduced to a level that is effective to protect the preparation of monoclonal immunoglobulins from the radiation. Suitable levels of residual solvent content may vary depending upon the nature and characteristics of the particular preparation of monoclonal immunoglobulins being irradiated and can be determined empirically by one skilled in the art. Preferably, when the solvent is water, the residual solvent content is less than about 10%, more preferably less than about 2.0%, more preferably less than about 1.0%, even more preferably less than about 0.5% and most preferably less than about 0.2%.

According to the methods of the present invention, the monoclonal antibody to be sterilized may be immobilized upon a solid surface by a means familiar to one skilled in the art.

According to the methods of the present invention, the rate of irradiation may be optimized to produce the most advantageous combination of product recovery and time required to complete the operation. Both low ($\leq 3$ kGy/hour) and high (>3 kGy/hour) rates may be achieved by the appropriate application of the methods described herein.

While not wishing to be bound by any theory of operability, it is believed that the reduction in residual solvent content reduces the degrees of freedom of the preparation of monoclonal immunoglobulins and thereby protects it from the effects of the radiation. Similar results might therefore be achieved by lowering the temperature of the preparation of monoclonal immunoglobulins below its eutectic point or below its freezing point, or by vitrification to likewise reduce the degrees of freedom of the preparation of monoclonal immunoglobulins. These results may permit the use of a higher rate of irradation than might otherwise be acceptable. Thus the inventions described herein may be carried out at any temperature that does not result in damage to the monoclonal immunoglobulin.

The residual solvent content of the preparation of monoclonal immunoglobulins may be reduced by any of the methods and techniques known to those skilled in the art for reducing solvent from a preparation of monoclonal immunoglobulins. Such methods may include, but are not limited to, evaporation, concentration, centrifugal concentration, vitrification and spray-drying. A particularly preferred method for reducing the residual solvent content of a preparation of monoclonal immunoglobulins is lyophilization. According to a particularly preferred embodiment of the present invention, a preparation of monoclonal immunoglobulins which has been lyophilized is stored under vacuum or an inert atmosphere (preferably a noble gas, such as helium or argon, more preferably a higher molecular weight noble gas, and most preferably argon) prior to irradation.

The radiation employed in the present invention may be any radiation effective for the inactivation of one or more biological contaminants of the preparation of monoclonal immunoglobulins being treated. The radiation may be corpuscular, including e-beam radiation. Preferably the radiation is electromagnetic radiation, including visible light, UV light and mixtures of various wavelengths of electromagnetic radiation and a particularly preferred form of radiation is gamma radiation.

According to the methods of the present invention, the preparation of monoclonal immunoglobulins is irradiated with the radiation at a rate effective for the inactivation of one or more biological contaminants of the preparation of monoclonal immunoglobulins. Suitable rates of irradiation may vary depending upon the particular form of radiation and the nature and characteristics of the particular preparation of monoclonal immunoglobulins being irradiated and the particular biological contaminants being inactivated. Suitable rates of irradiation can be determined empirically by one skilled in the art. Preferably, the rate of irradiation is constant for the duration of the sterilization procedure. When this is impractical, a variable or discontinuous irradiation may be utilized.

According to a particularly preferred embodiment of the present invention, the rate of irradiation is not more than about 3.0 kGy/hour, more preferably between about 0.1 kGy/hr. and 3.0 kGy/hr, even more preferably between about 0.25 kGy/hr and 2.0 kGy/hour, still even more preferably between about 0.5 kGy/hr and 1.5 kGy/hr and most preferably between about 0.5 kGy/hr and 1.0 kGy/hr.

According to another particularly preferred embodiment of the present invention, the rate of irradiation is at least about 3.0 kGy/hr., more preferably at least about 6 kGy/hr., even more preferably at least about 16 kGy/hr., and even more preferably at least about 30 kGy/hr and most preferably at least about 45 kGy/hr or greater.

The preparation of monoclonal immunoglobulins is irradiated with the radiation for a time effective for the inactivation of one or more biological contaminants of the preparation of monoclonal immunoglobulins. Combined with irradiation rate, the appropriate irradiation time results in the appropriate dose of irradiation being applied to the monoclonal immunoglobilin. Suitable ionization times may vary depending upon the particular form and rate of radiation and the nature and characteristics of the particular preparation of monoclonal immunoglobulins being irradiated and the particular biological contaminants being inactivated. Suitable irradiation times can be determined empirically by one skilled in the art.

Optionally, an effective amount of at least one sensitizing compound may be added to the monoclonal immunoglobulin prior to irradiation to enhance the anti-microbial effect of the irradiation, while employing the methods described herein to minimize the deleterious effects of irradiation upon the monoclonal immunoglobulin. Suitable sensitizers are known to those skilled in the art.

According to methods of the present invention, the irradiation of the preparation of monoclonal immunoglobulins may occur at any temperature which is not deleterious to the preparation of monoclonal immunoglobulins being treated. According to a preferred embodiment, the preparation of monoclonal immunoglobulins is irradiated at ambient temperature. According to an alternate preferred embodiment, the preparation of monoclonal immunoglobulins is irradiated at reduced temperature, preferably at or below the freezing or eutectic point of the preparation of monoclonal immunoglobulins.

In order to avoid aggregation of the monoclonal immunoglobulins, the preparation of monoclonal immunoglobulins may have a pH of less than 7, preferably less than 6, more preferably less than 5, even more preferably less than 4, and most preferably less than 3.

It will be appreciated that combination of the several methods described herein may be employed to further minimize undesirable effects upon the monoclonal immunoglobulin caused by irradiation, while maintaining adequate effectiveness of the anti-microbial properties of the irradiation process.

EXAMPLES

The following examples are illustrative, but not limiting, of the present invention. Other suitable modifications and adaptations are of the variety normally encountered by those skilled in the art and are fully within the spirit and scope of the present invention. Unless otherwise noted, all irradiation was accomplished using a $^{60}$Co source.

Example 1

In this experiment the protective effects of certain stabilizers were evaluated using lyophilized anti-insulin monoclonal immunoglobulin exposed to 45 kGy of low dose gamma irradiation. The stabilizers tested were: sodium ascorbate, methionine, and lipoic acid.
Method In 2 ml glass vials, a 0.5 ml total volume was lyophilized containing 50 μg anti-insulin monoclonal immunoglobulin, 5 mg bovine serum albumin (1%) and either no stabilizer or 50 mM of the stabilizer of interest. The samples were stoppered under vacuum. Samples were irradiated with gamma radiation (45 kGy total dose, dose rate 1.83 kGy/hr, temperature 4° C.) and then reconstituted with water.

Immunoglobulin binding activity of independent duplicate samples was determined by a standard ELISA protocol: 96-well microtitre plates were coated overnight with 2.5 μg/ml insulin antigen. Three-fold serial dilutions of anti-insulin monoclonal antibody samples starting at 5 μg/ml were used. Goat anti-mouse Ig conjugated to phosphatase used at 50 ng/ml. Sigma 104 alkaline phosphatase substrate was used at 1 mg/ml in DEA buffer. Binding activity was determined by absorbance at 405–620 nm.

Relative protection was determined by estimating the shift in the titration curve (i.e. concentration of immunoglobulin needed to observe the same amount of binding) of the irradiated sample compared to an unirradiated sample at approximately 50% of the maximum absorbance signal for the unirradiated sample.
Results Lyophilized samples containing no stabilizer retained 50% of immunoglobulin avidity following irradiation with 45 kGy gamma irradiation. This is in contrast to previous results in which 45 kGy of gamma radiation destroyed essentially all the activity of immunoglubulin when it was irradiated in solution. Thus, it is apparent that the reduction in residual water content by lyophilizing afforded significant protection on its own to the monoclonal immunoglobulin.

The addition of sodium ascorbate provided full recovery of activity after irradiation of the sample. Both methionine and lipoic acid provided significant recovery of activity (76–83%) of activity after irradiation as compared to the unirradiated sample. The results are shown in FIGS. 1 and 2. Similar results (65% recovery of activity) were also seen for pupurogalin (data not shown).

Example 2

In this experiment, the protective effects of certain stabilizers were evaluated using lyophilized anti-insulin monoclonal immunoglobulin exposed to 45 kGy of low dose gamma irradiation. The stabilizers tested were: sodium ascorbate, N-acetyl cysteine, glutathione and mixtures of urate/trolox and ascorbate/urate/trolox.
Method In 3 ml glass vials, a 1.0 ml total volume was lyophilized containing 100 μg anti-insulin monoclonal immunoglobulin, 10 mg bovine serum albumin (1%) and either no stabilizer or the stabilizer of interest. The samples were stoppered under vacuum. Samples were irradiated with gamma radiation (45 kGy total dose, dose rate 1.83 kGy/hr, temperature 4° C.) and then reconstituted with 1.0 ml water.

Immunoglobulin binding activity of independent duplicate samples was determined by a standard ELISA protocol: Maxisorb plates were coated overnight with 2.5 μg/ml insulin antigen. Three-fold serial dilutions of anti-insulin monoclonal immunoglobulin samples starting at 5 μg/ml were used. Goat anti-mouse Ig conjugated to phosphatase was used at 50 ng/ml. Binding activity was determined by absorbance at 405–620 nm.

Relative protection was determined using a parallel line analysis software package (PLA 1.2 from Stegmann Systemberatung).
Results Lyophilized samples containing no stabilizer retained 70% of immunoglobulin avidity following irradiation with 45 kGy gamma irradiation. This is in contrast to previous results in which 45 kGy of gamma radiation destroyed essentially all the activity of immunoglubulin when it was irrradiated in solution. Thus, it is apparent that the reduction in residual water content by lyophilizing afforded significant protection on its own protein.

Figure 3B:
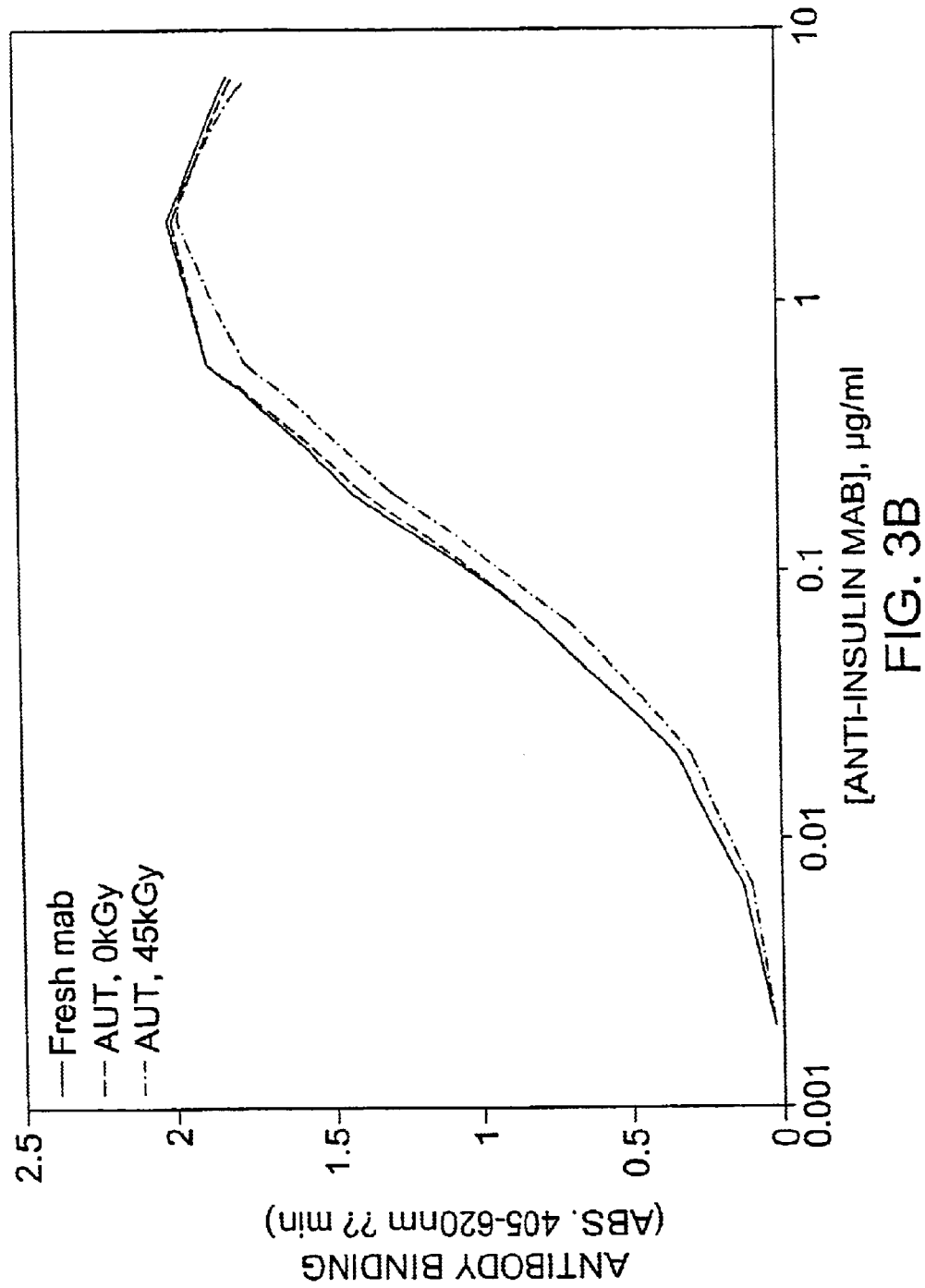

The presence of sodium ascorbate increased recovery by 20%, i.e. such that there is 90% avidity recovered after irradiation. The remaining stabilizers resulted in recovery of 77–84% of avidity. The results are shown in FIGS. 3A–3C.

Example 3

In this experiment, the protective effects of primary lyophilizing (which leaves a relatively "high moisture" content in the product) and the combination of both primary and secondary lyophilizing (which results in a product with relatively "low moisture") on the radiation sensitivity of a monoclonal immunoglobulin were determined.
Methods In 3 ml glass vials, 1.0 ml total volume was lyophilized (using either only primary or a combination of both primary and secondary drying) containing 100 µg anti-insulin monoclonal immunoglobulin, 10 mg bovine serum albumin (1%) and either no stabilizer or 100 mM of sodium ascorbate. The samples were stoppered under vacuum. Samples were irradiated with gamma radiation (45 kGy total dose, dose rate between 2.03 and 2.13 kGy/hr, temperature 4° C.) and then reconstituted with 1.0 ml water.

Immunoglobulin binding activity of independent duplicate samples was determined by a standard ELISA protocol: Maxisorb plates were coated overnight with 2.5 µg/ml insulin antigen. Three-fold serial dilutions of anti-insulin mAb samples starting at 5 µg/ml were used. Goat anti-mouse Ig conjugated to phosphatase was used at 50 ng/ml. Binding activity was determined by absorbance at 405–620 nm.
Results In the absence of a stabilizer, there was better recovery of the anti-insulin immunoglobulin after irradiation from the samples that had undergone the secondary "low moisture" drying cycle, i.e. a lower total moisture content in the absence of a stabilizer improved recovery.

In the presence of the stabilizer, however, there was very good recovery of antibody activity after 45 kGy irradiation, irrespective of whether the sample had undergone only the primary "high moisture" drying cycle or had also undergone the secondary "low moisture" drying cycle.

Figure 4:
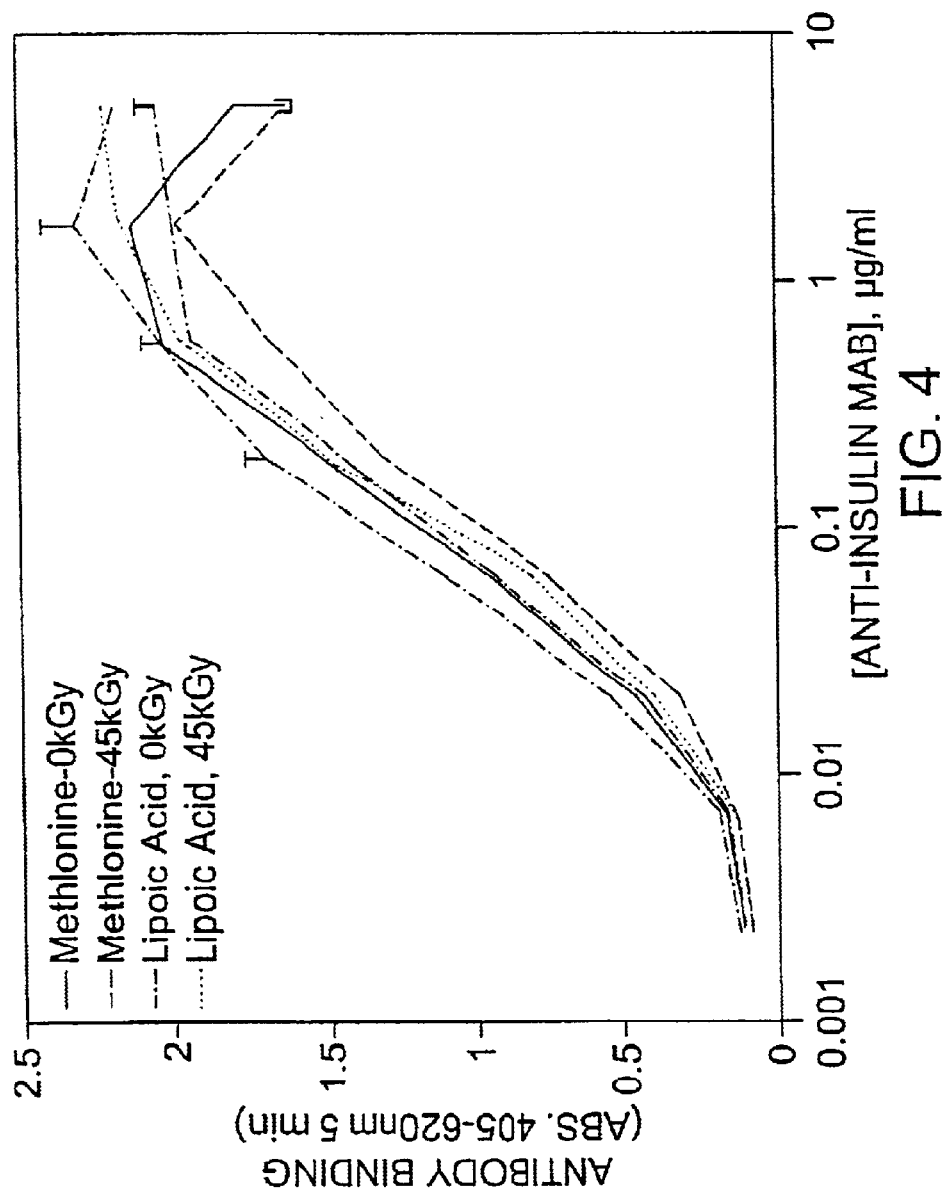
FIGS. 4 & 5 are graphs showing the protective effects of primary lyophilizing and secondary lyophilizing on the sensitivity of a monoclonal immunoglobulin.
Figure 5:
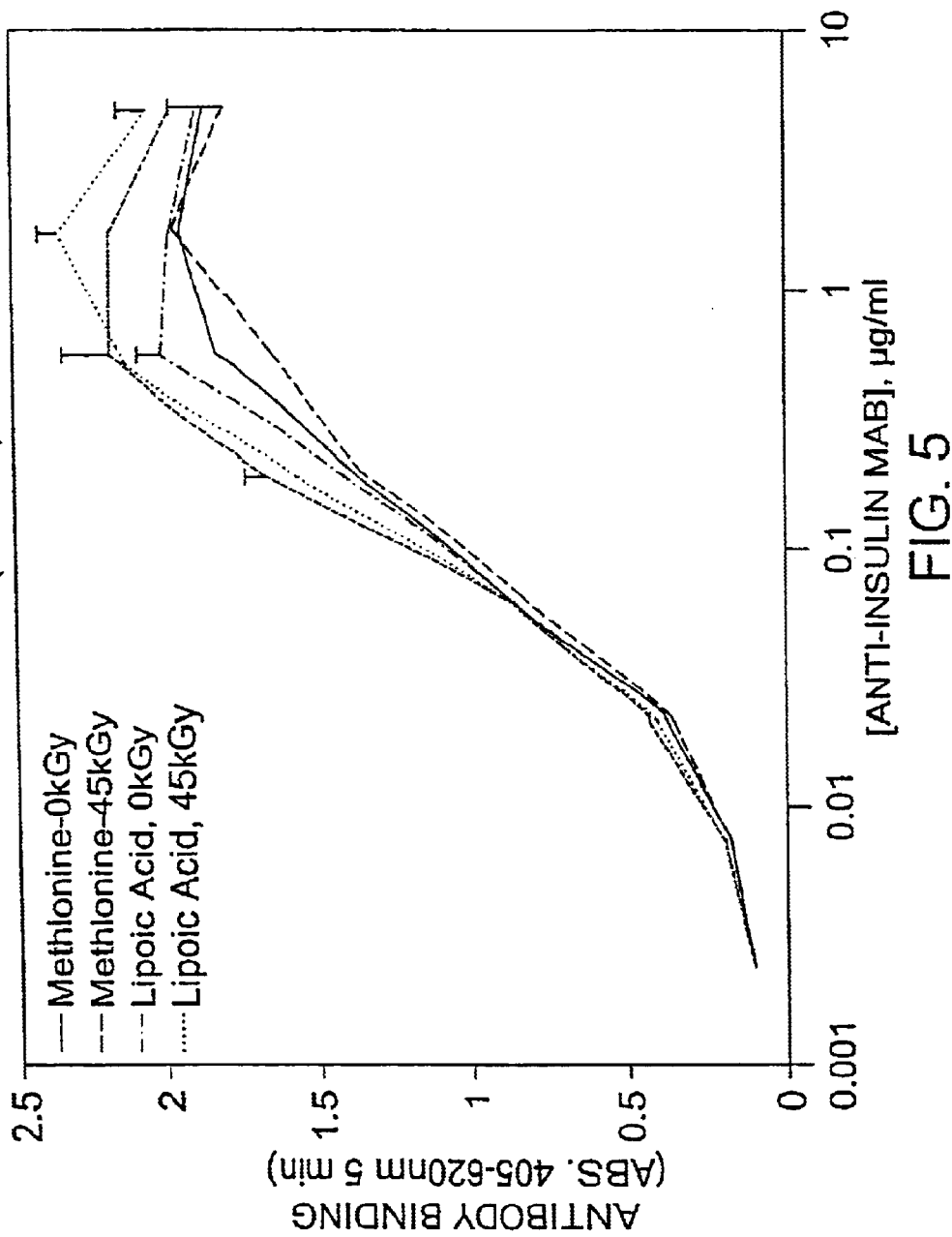
Figure 6:
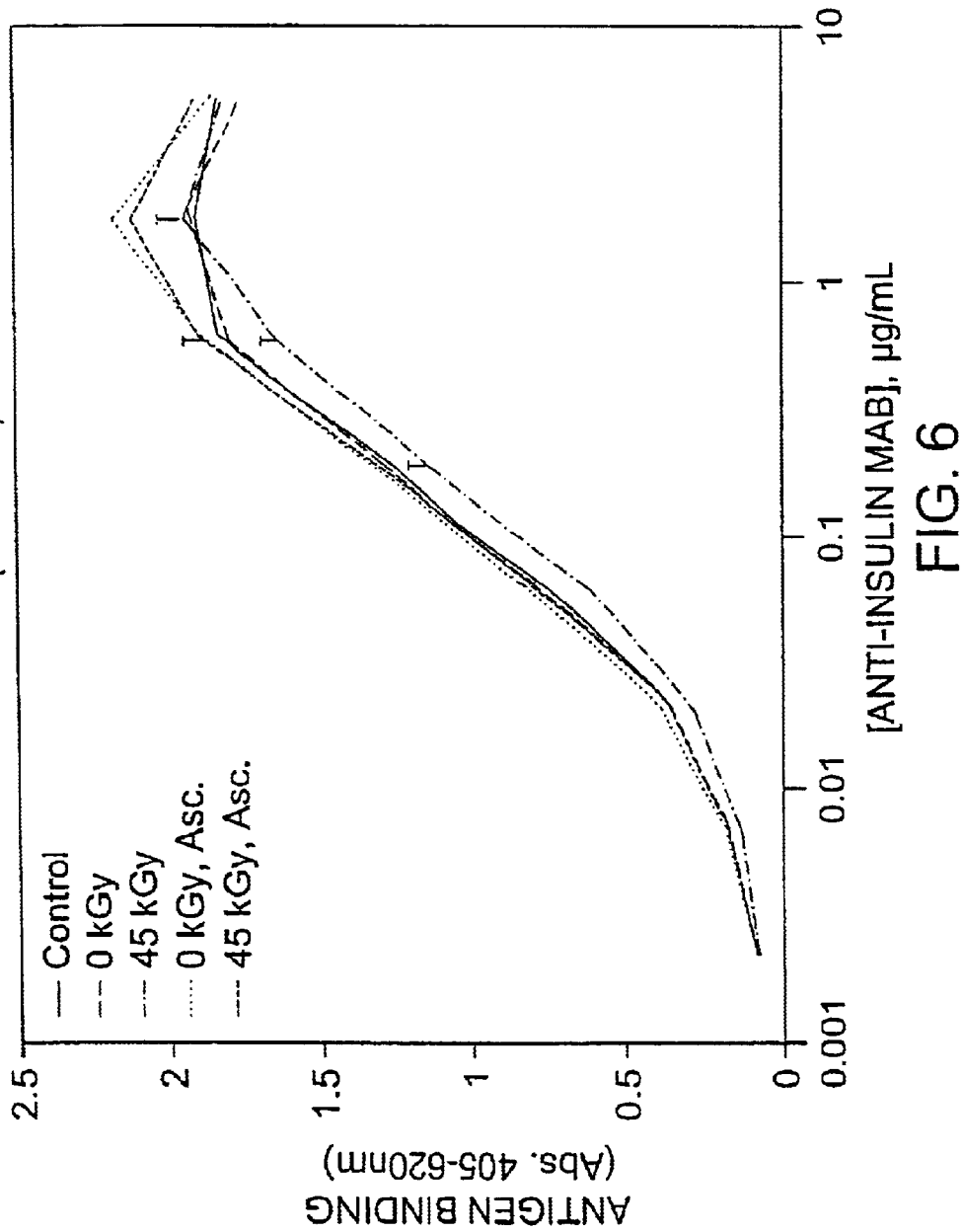
FIGS. 6–11 are graphs showing the protective effect of certain stabilizers on the activity of lyophilized anti-insulin monoclonal immunoglobulin.
Figure 7:
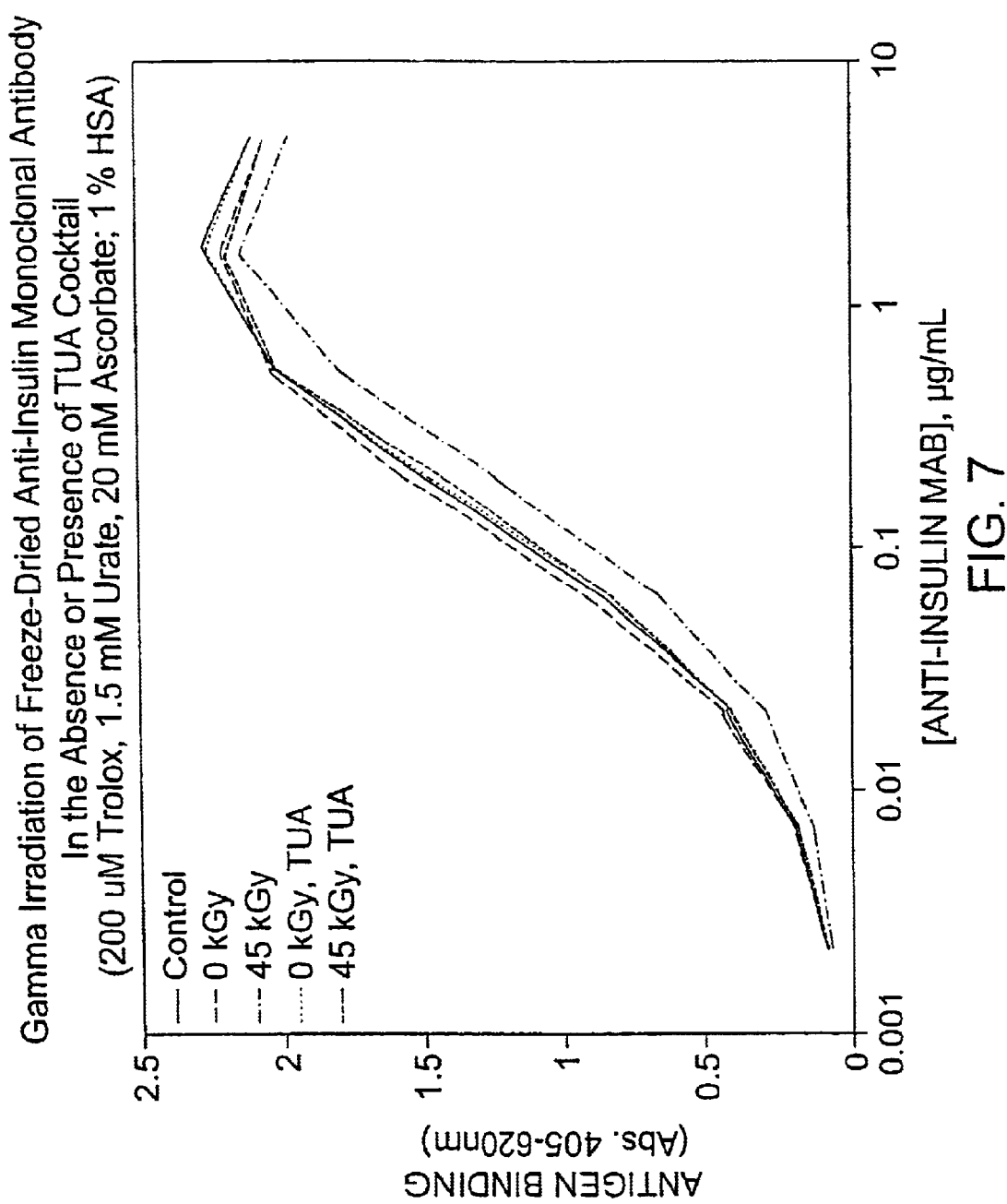
Figure 8:
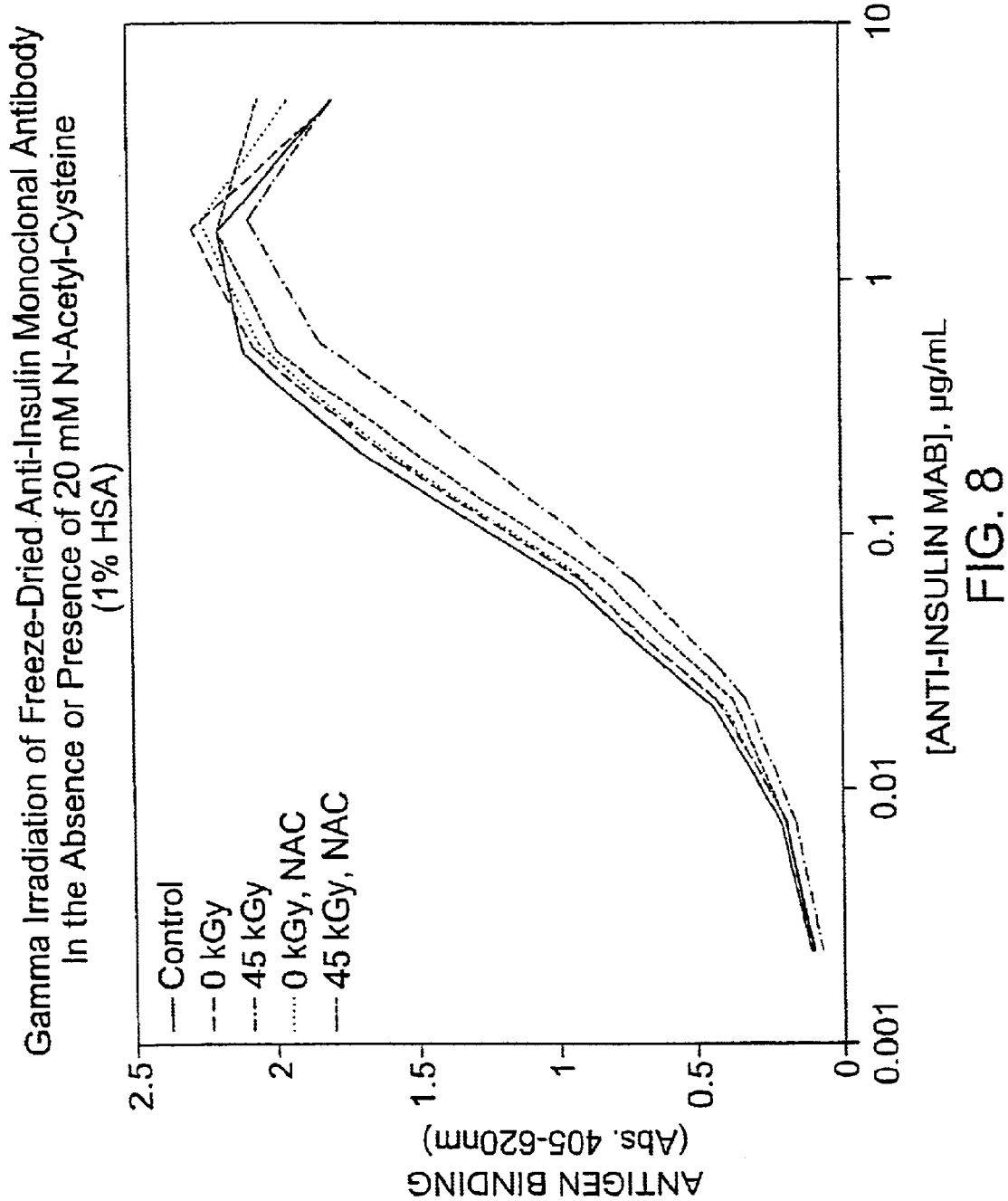
Figure 9:
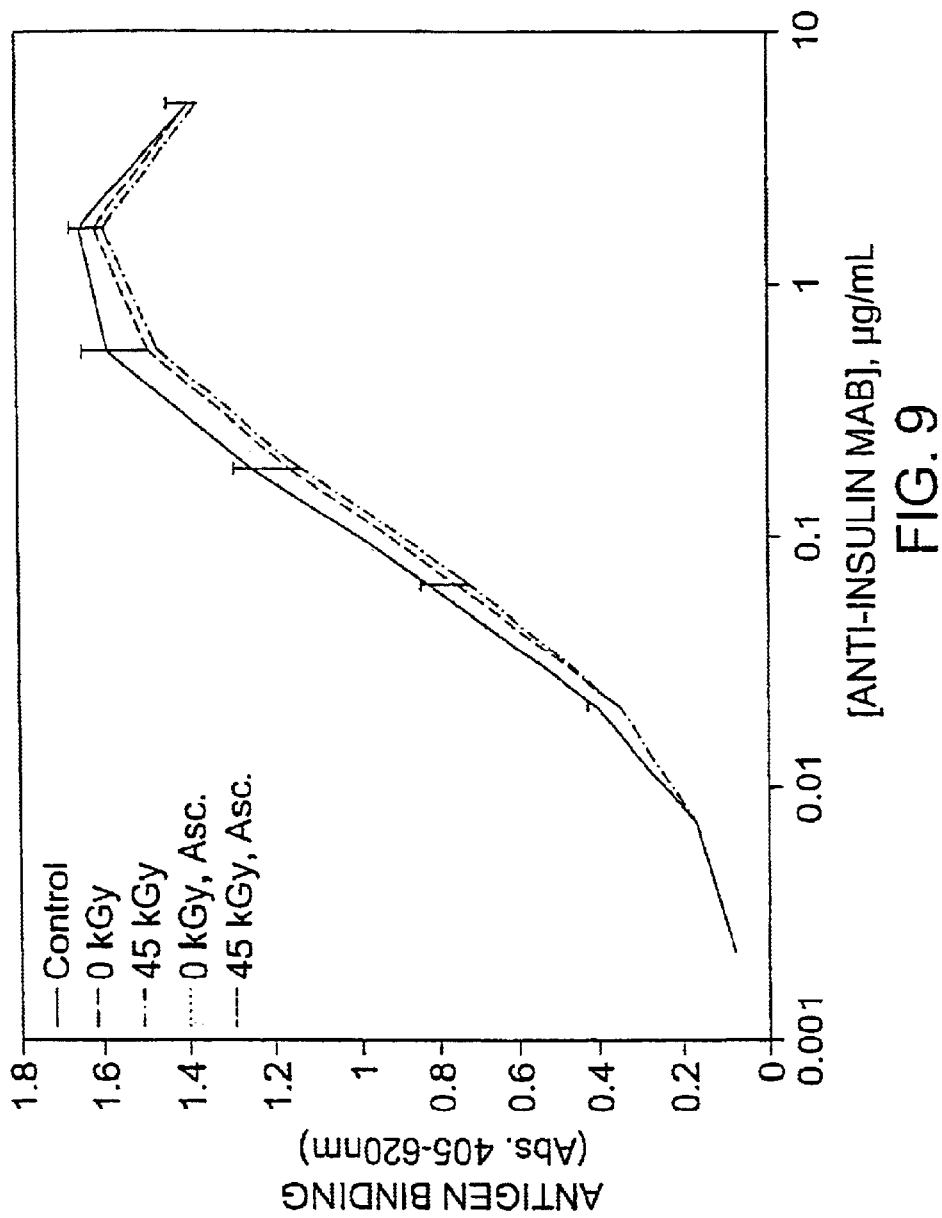
Figure 10:
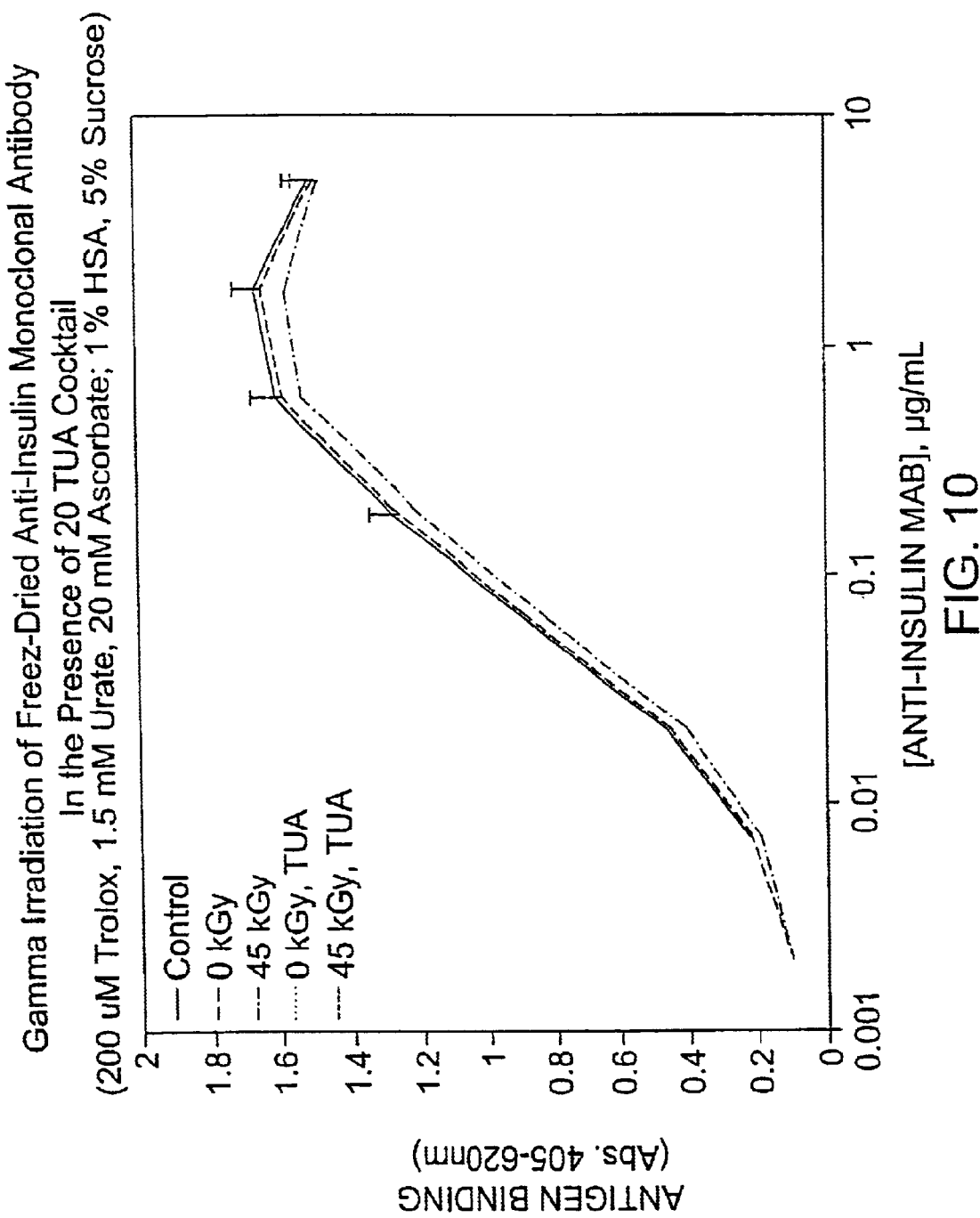
Figure 11:
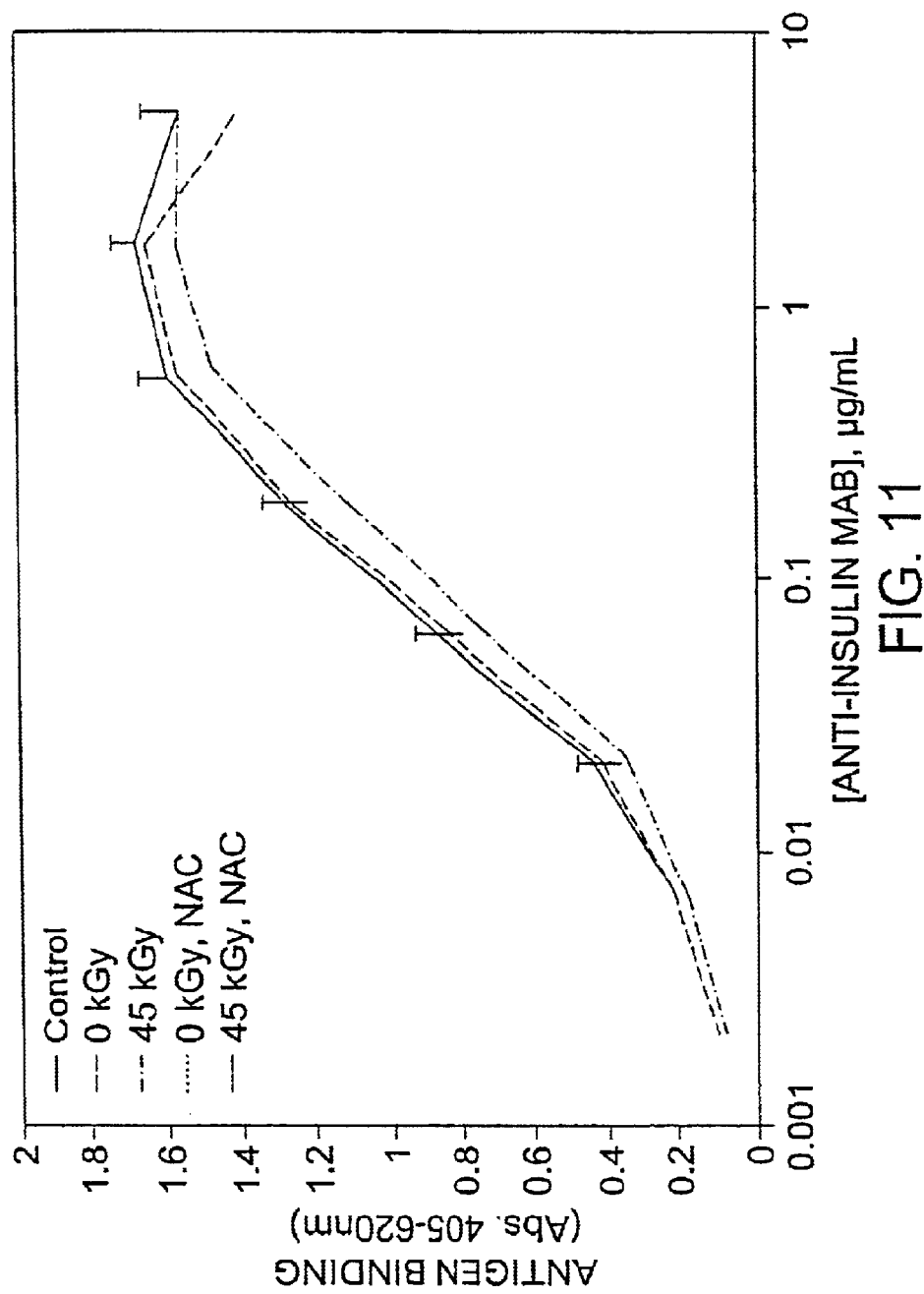

The results of this experiment are shown in FIGS. 4 and 5.

Example 4

In this experiment, the protective effect of certain stabilizers on the activity of lyophilized anti-insulin monoclonal immunoglobulin was determined. The stabilizers tested were; sodium ascorbate; trolox/urate/ascorbate mixtures; and N-acetyl cysteine.
Methods Anti-insulin monoclonal immunoglobulin supplemented with 1% of human serum albumin (and, optionally, 5% sucrose) was lyophilized, stoppered under vacuum, and irradiated (total dose 45 kGy; dose rate between 1.83 and 1.88 kGy/hr). Immunoglobulin binding activity was determined using the standard ELISA protocol described above.
Results Irradiation of lyophilized anti-insulin immunoglobulin supplemented with 1% HSA to a dose of 45 kGy resulted in an average loss of avidity of about 33%. The addition of the following stabilizers significantly improved recovery: 20 mM sodium ascorbate (100% recovery); 200 µM trolox/1.5 mM urate/20 mM ascorbate (87%) recovery); 20 mM N-acetyl cysteine (82% recovery The addition of 5% sucrose to the lyophilized immunoglobulin containing 1% HSA resulted in an average loss of avidity of about 30% when irradiated to a dose of 45 kGy. The addition of the following stabilizers significantly improved recovery: 20 mM sodium ascorbate (88% recovery); 200 µM trolox/1.5 mM urate/20 mM ascorbate (84%) recovery); 20 mM N-acetyl cysteine (72% recovery).

The results of these experiments are shown in FIGS. 6–11.

Example 5

Figure 12:
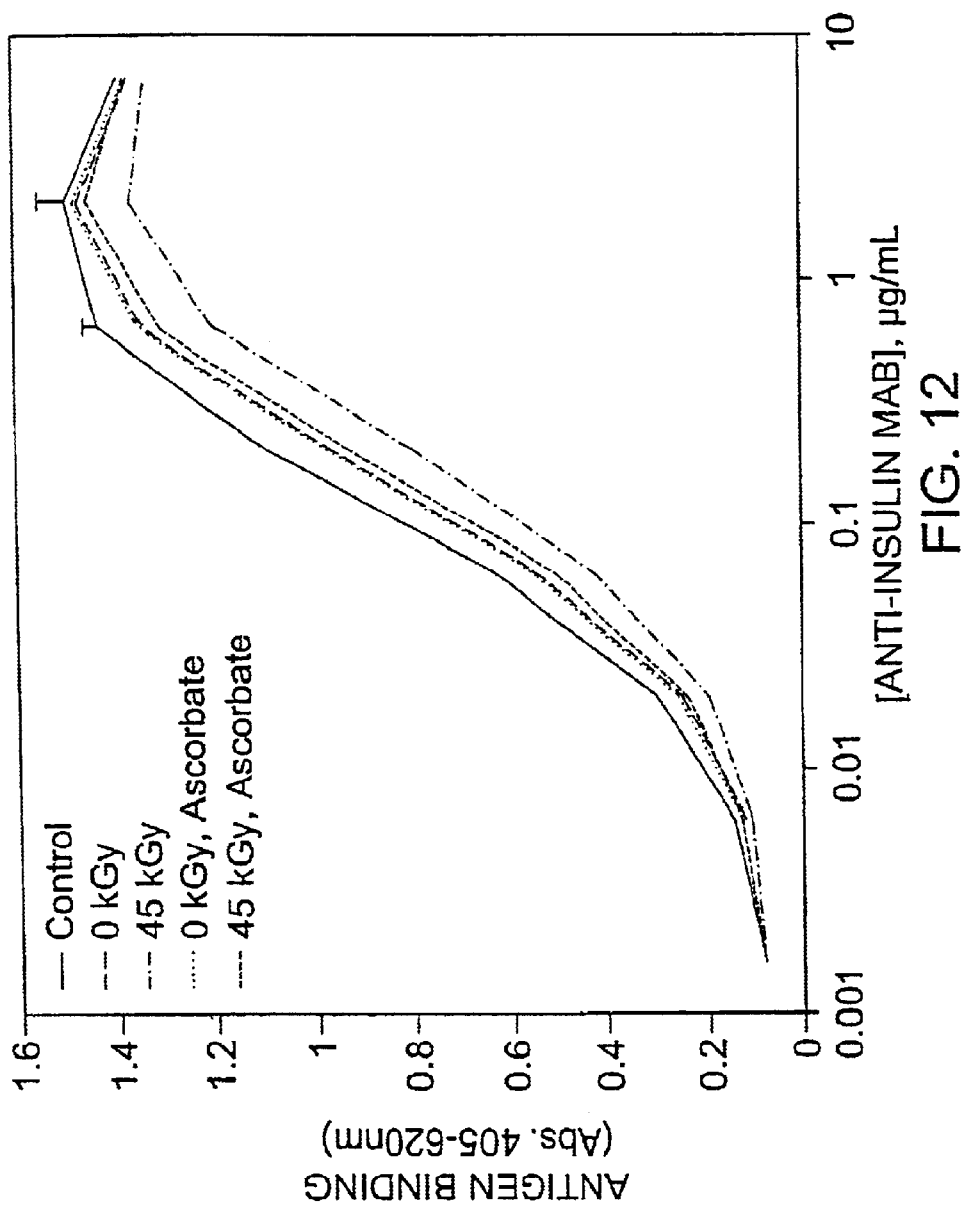
FIG. 12 is a graph showing the protective effect of stabilizers on the activity of lyophilized anti-insulin monoclonal immunoglobulin when the sample was irradiated at a high dose rate (30 kGy/hr).

In this experiment, the protective effect of stabilizers (ascorbate) on the activity of lyophilized anti-insulin monoclonal immunoglobulin was determined when the sample was irradiated at a high dose rate (30 kGy/hr).
Methods Anti-insulin monoclonal immunoglobulin was lyophilized and irradiated at a rate of 30 kGy/hr (total dose 45 kGy). Immunoglobulin binding activity was determined using the standard ELISA protocol described above.
Results Irradiation of lyophilized anti-insulin immunoglobulin to a dose of 45 kGy resulted in an average loss of activity of about 32%. The addition of 20 mM sodium ascorbate provided 85% recovery of avidity compared to an unirradiated sample. The results are shown in FIG. 12.

Example 6

In this experiment, an IgM monoclonal immunoglobulin specific for murine $IgG_3$ was irradiated at a low dose rate in the presence or absence of a stabilizer.
Method Liquid rat anti-murine $IgG_3$ monoclonal IgM (in a PBS buffer with 10 mM sodium azide; concentration of antibody was 666 ng/µl) was irradiated at a rate of 1.8 kGy/hr to a total dose of either 10 kGy or 45 kGy. Samples either contained no stabilizer or a stabilizer mixture containing 20 mM citrate, 300 µM urate and 200 mM ascorbate.

Figure 13:
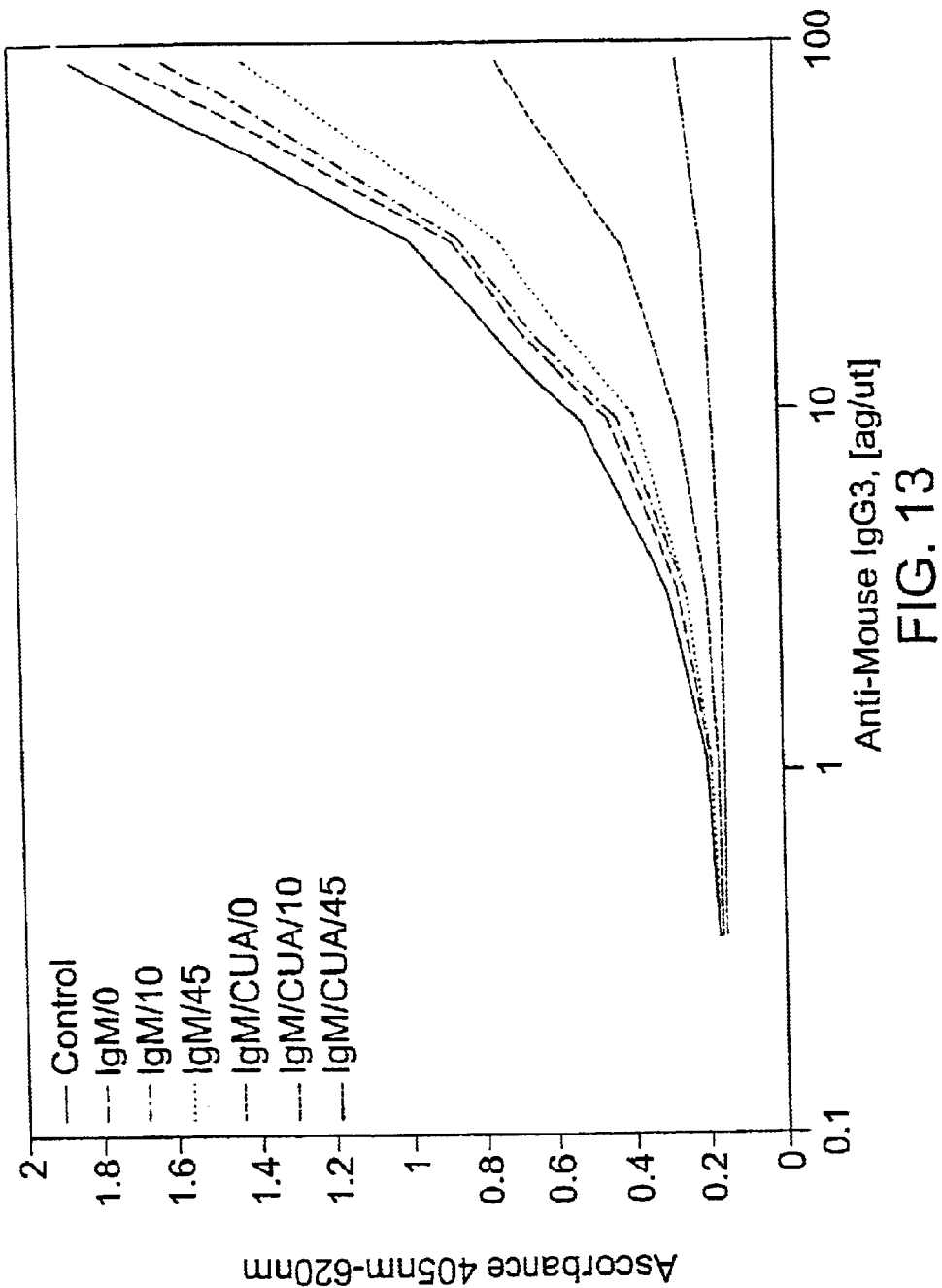
FIG. 13 is a graph showing the effect of a stabilizer on IgM activity after irradiation with gamma radiation.

Immunoglobulin activity was analyzed by standard ELISA protocol using murine IgG3 as the coating antigen and a phosphatase-conjugated anti-rat IgM detection antibody.
Results Liquid samples containing no stabilizer lost all functional immunoglobulin activity following irradiation with either 10 kGy or 45 kGy gamma irradiation. The presence of a stabilizer mixture, however, provided full recovery of activity following irradiation with 10 kGy gamma radiation and 88% recovery of activity following irradiation with 45 kGy gamma radiation. The results of this experiment are shown graphically in FIG. 13.

Example 7

In this experiment, the protective effects of certain stabilizers were evaluated using immobilized anti-human insulin monoclonal immunoglobulin exposed to 45 kGy of low dose-rate gamma irradiation. The stabilizers tested were: sodium ascorbate, reduced glutathione, sodium formaldehyde sulfoxylate, and polypropylene glycol.
Method Two plates were coated with 100 µl/well of freshly prepared 2 µg/ml anti-insulin immunoglobulin in coating buffer overnight at 4° C. The plates were washed briefly three times with PBS. A two-fold dilution series of each stabilizer in PBS was prepared. 100 μl of a selected stabilizer solution was added to each well. The plates were covered tightly with a cap mat. One plate was irradiated at 1.92 kGy/hr for a total of 45 kGy at 4° C. The control plate received 0 kGy and was stored at 4° C.

Immunoglobulin binding activity was determined by a standard ELISA protocol. The plate wells were emptied and were washed four times with a full volume of PBS. A full volume of blocking buffer (approximately 380 μl) was added to all wells and incubated for two hours at 37° C. All wells were washed four times with TBST (TBS pH 7.4 with 0.05% TWEEN 20). One hundred μl of 50 ng/ml biotin-labelled insulin in binding buffer was added to each well. The plates were covered with a plate sealer and incubated at 37° C. while shaking (LabLine titer plate shaker set at 3) for 1.5 hours. The plates were then washed four times with TBST. One hundred μl of 0.5 μg/ml phosphatase-labelled Streptavidin (stock diluted 1:1000 in binding buffer) was added to each well. The plates were covered with a plate sealer and incubated at 37° C. for one hour with shaking. The plates were then washed four times with TBST. One hundred μl of 1 mg/ml Sigma 104 phosphatase substrate in DEA buffer was added to each well. The plates were then incubated at 37° C. with shaking. Absorbance was determined at 405 nm–628 nm at 5 minute intervals.

Results

Figure 14A:
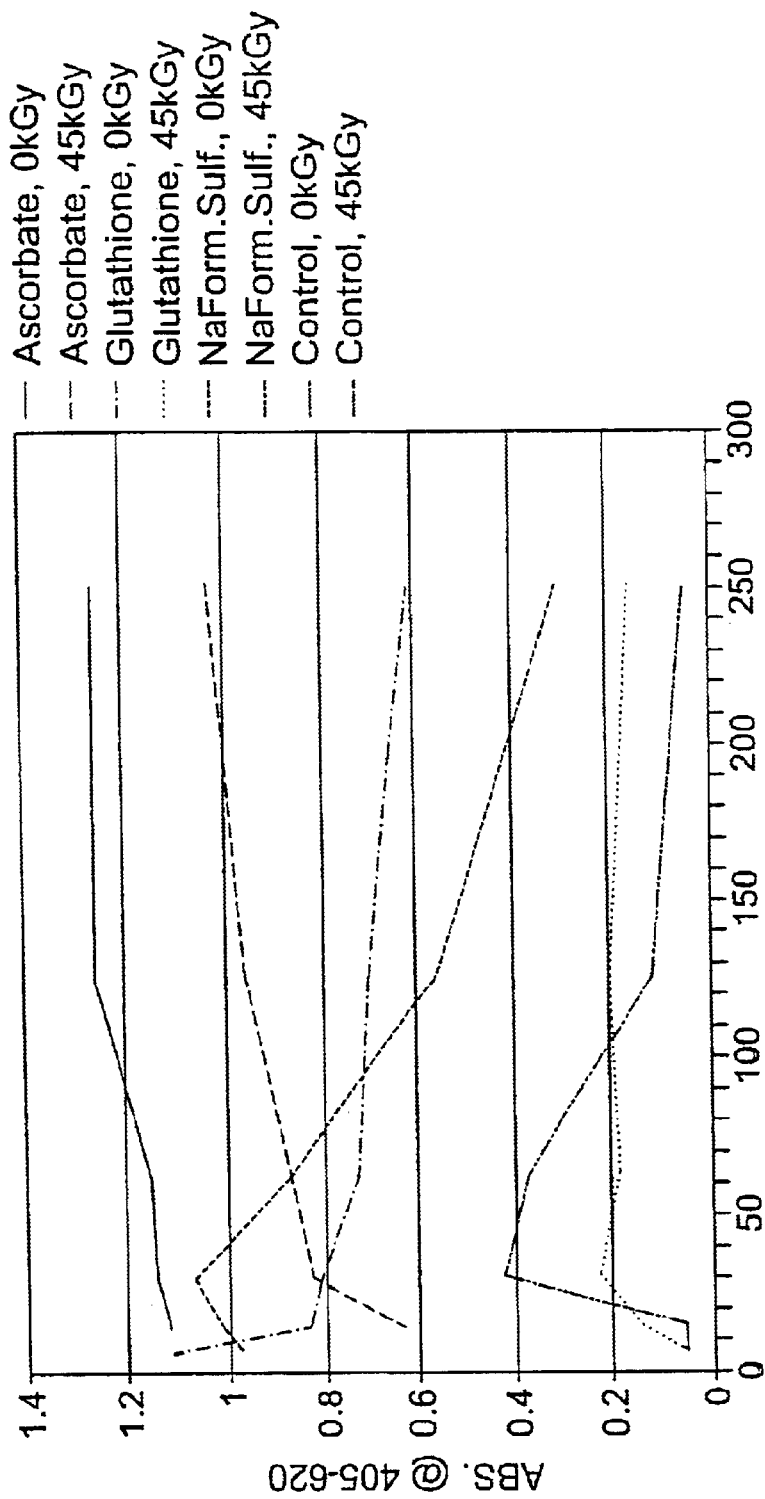
FIGS. 14 and 15 are graphs showing the effect of stabilizers on immobilized anti-insulin monoclonal immunoglobulin after irradiation with gamma radiation.
Figure 15:
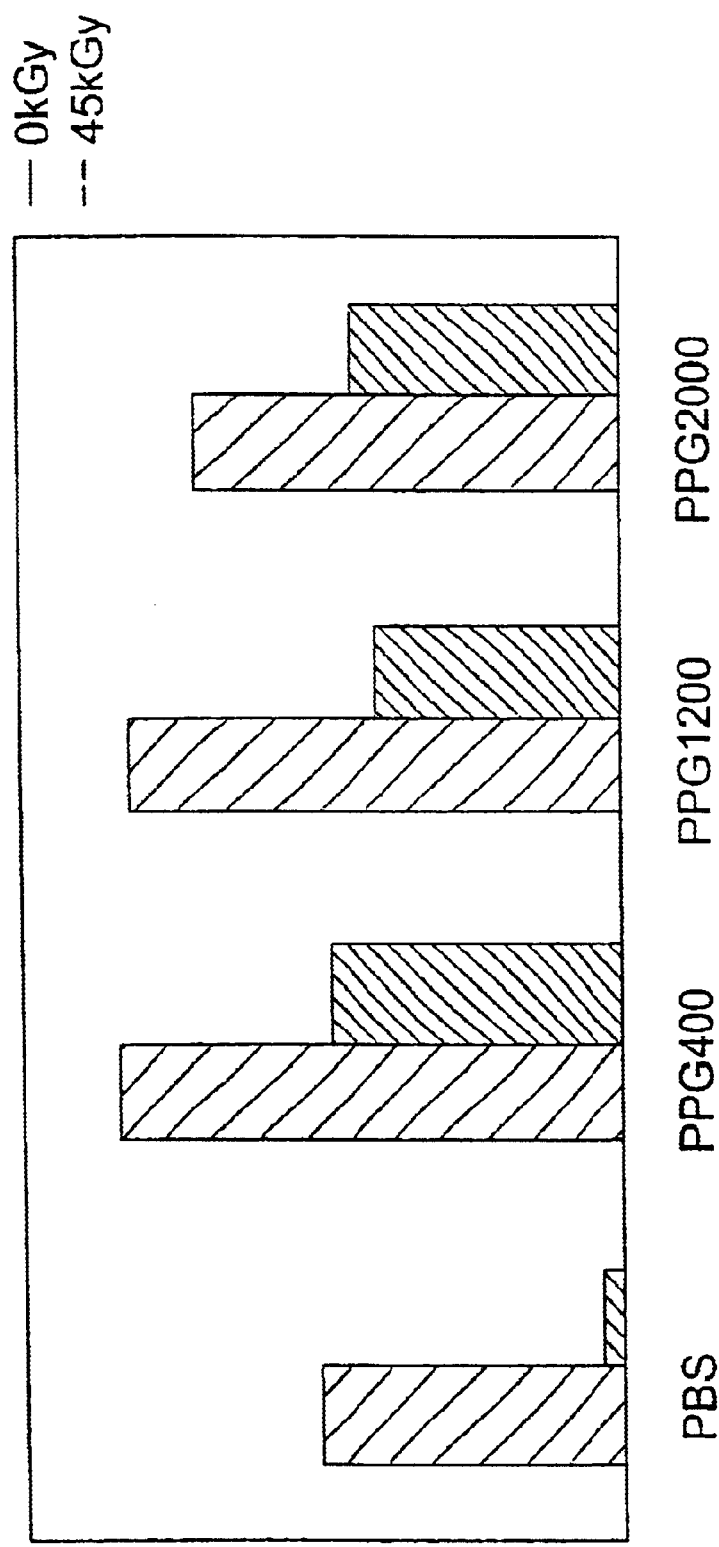

As shown in FIGS. 14 and 15, sodium ascorbate exhibited a dose-dependent protective effect. Samples containing between 31–250 mM of sodium ascorbate exhibited 73–81% greater retained activity.

Samples containing glutathione exhibited approximately 25% greater retention of monoclonal immunoglobulin activity, that was dose dependent up to a glutathione concentration of about 31 mM.

Samples treated with sodium formaldehyde sulfoxylate exhibited approximately 50% greater retained activity than control samples at a stabilizer concentration of 31 mM.

All three forms of polypropylene glycol (i.e. polypropylene P400 (Fluka 81350); polypropylene P1200 (Fluka 81370); and polypropylene P2000 (Fluka 81380)) exhibited a protective effect. Samples treated with polypropylene glycol exhibited approximately 50–60% increased retention of activity relative to control samples.

Example 8

In this experiment, the optimal concentration of sodium ascorbate to protect immobilized anti-insulin monoclonal immunoglobulins from 45 kGy of gamma irradiation was determined. It was also determined whether the presence of 1.5 mM uric acid has any effect on the stabilizing nature of ascorbate of immobilized monoclonal immunoglobulin exposed to 45 kGy gamma irradiation.

Method

Two plates were coated overnight at 4° C. with 100 μl of 2.5 μg/ml anti-insulin monoclonal immunoglobulin in coating buffer. The coating solution was discarded and the wells washed two times with PBS. Twenty-five μl of 4×ascorbate solution was added to appropriate wells. Seventy-five μl of water was added to the urate-free wells (rows a–d). Twenty five μl of water was added to the urate containing wells (rows e–h). Fifteen μl of 3 mM urate was added to the urate containing wells (rows e–h). The plates were covered with a 96-well cap mat. One plate was irradiated with gamma radiation at 1.9 kGy/hr for a total of 45 kGy at 4° C. The other plate was stored at 4° C. as a travel control.

Immunoglobulin binding activity was determined by a standard ELISA protocol as follows. The well contents were removed, and the wells washed twice with a full volume of PBS. Non-specific binding sites were blocked by adding a full volume of blocking buffer (approximately 380 μl) to all wells and incubated for two hours at 37° C. All wells were washed three times with TBST. One hundred μl of 10 ng/ml insulin-biotin in binding buffer was added to each well (stock diluted 1:100,000 in binding buffer). The plates were covered with a plate sealer and incubated at 37° C. with shaking (LabLine titer plate shaker set at three) for one hour. The plates were washed with TBST for four sets of two washes each set, usually leaving five minutes between each set. One hundred μl of 25 ng/ml phosphatase-labelled Streptavidin (stock diluted 1:20,000 in binding buffer) was added to each well. Plates were covered with a plate sealer and incubated at 37° C. for one hour with shaking. Each plate was washed with TBST for four sets of two washes each set, usually leaving approximately five minutes between each set. One hundred μl of 1 ng/ml Sigma 104 phosphatase substrate in DEA buffer was added to each well. The plates were incubated at ambient temperature with nutation. Absorbance was determined at 405 nM-620 nM.

Results

Figure 16A:
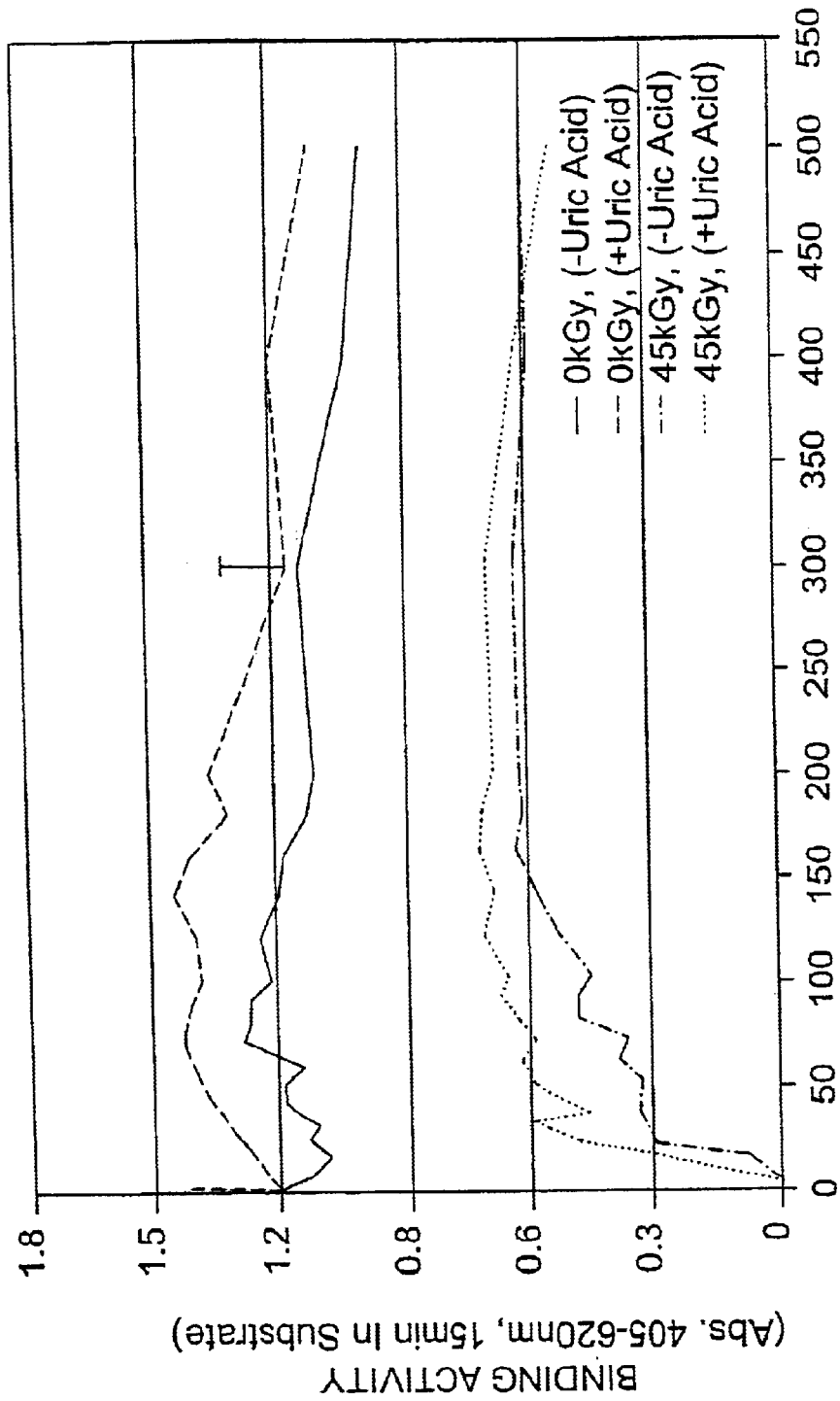
Figure 16B:
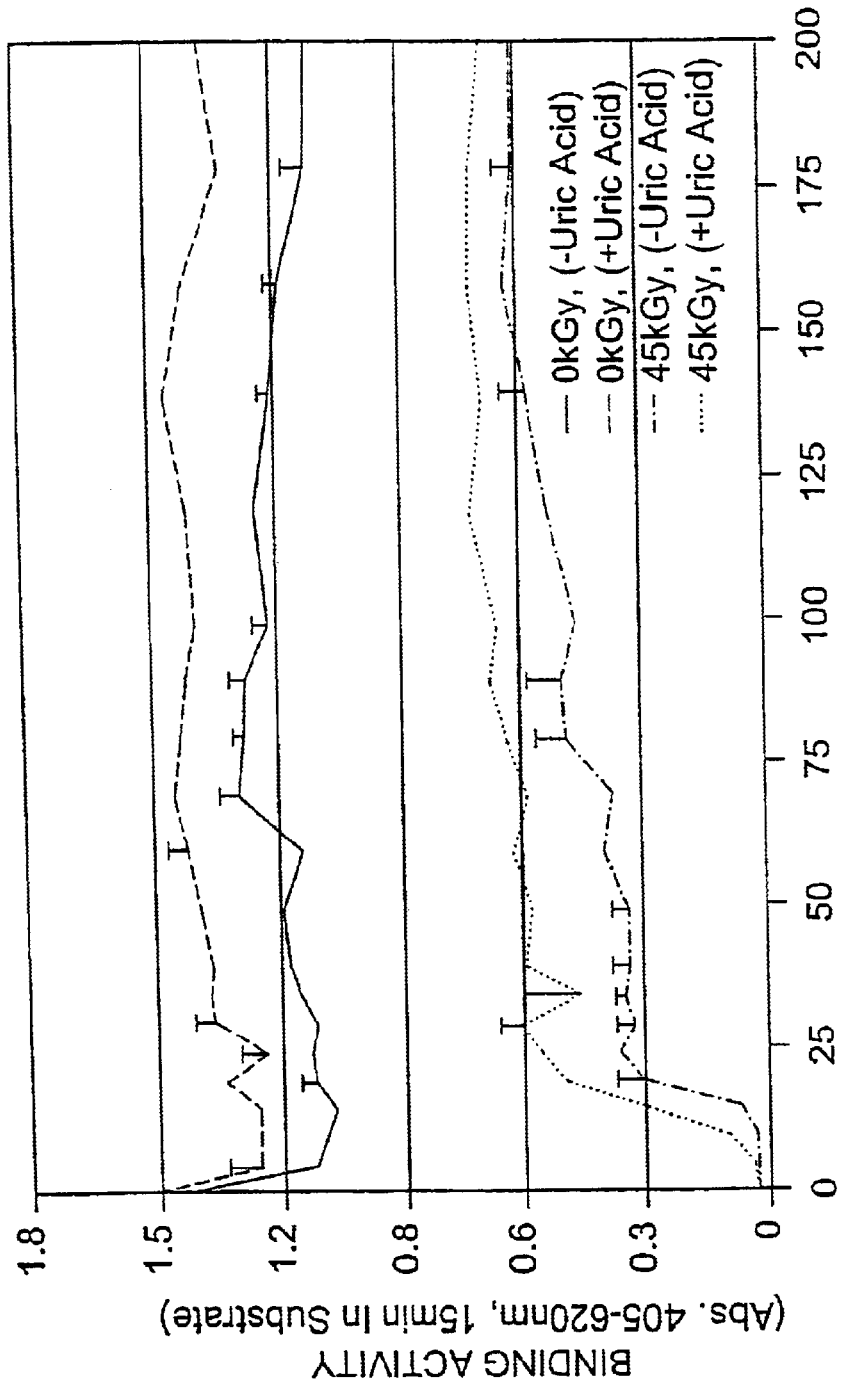

It was determined that the optimal concentration of sodium ascorbate necessary to provide maximal protection of immobilized anti-insulin monoclonal immunoglobulins in an aqueous environment (in the absence of uric acid) is approximately 150 mM. Approximately 50% recovery of the anti-insulin binding activity was achieved at a concentration of approximately 150 mM ascorbate. The addition of 1.5 mM uric acid resulted in a slight left shift in the ascorbate dose curve (~5 mM) and appeared to cause maximal recovery of activity to be achieved at a lower concentration of ascorbate (~30 mM). FIG. 16A shows the complete data set, and FIG. 16B is an expansion of the critical region of the data used to determine these values.

Example 9

In this experiment, the optimal concentration of sodium ascorbate to protect immobilized monoclonal immunoglobulin from 45 kGy gamma irradiation was determined. The experiment also determined whether the presence of 2.25 mm of uric acid effects the stabilizing effect of ascorbate.

Method

Two plates were coated overnight at 4° C. with 100 μl of 2.5 μg/ml anti-insulin monoclonal immunoglobulin in coating buffer. The coating solution was discarded and the wells washed twice with PBS. Twenty-five μl of 4×ascorbate solution was added to appropriate wells. Seventy-five μl of water was added to the urate-free wells (rows a–d). Seventy-five μl of 3 mM urate stock was added to the urate-containing wells (rows e–h) (f.c.=2.25 mM). The plates were covered with a 96-well cap mat. One plate was irradiated with gamma radiation at 1.9 kGy/hr for a total of 45 kGy at 4° C. The other plate was stored at 4° C. as a travel control.

Monoclonal immunoglobulin binding activity was determined as in Example 8.

Results

Figure 17B:
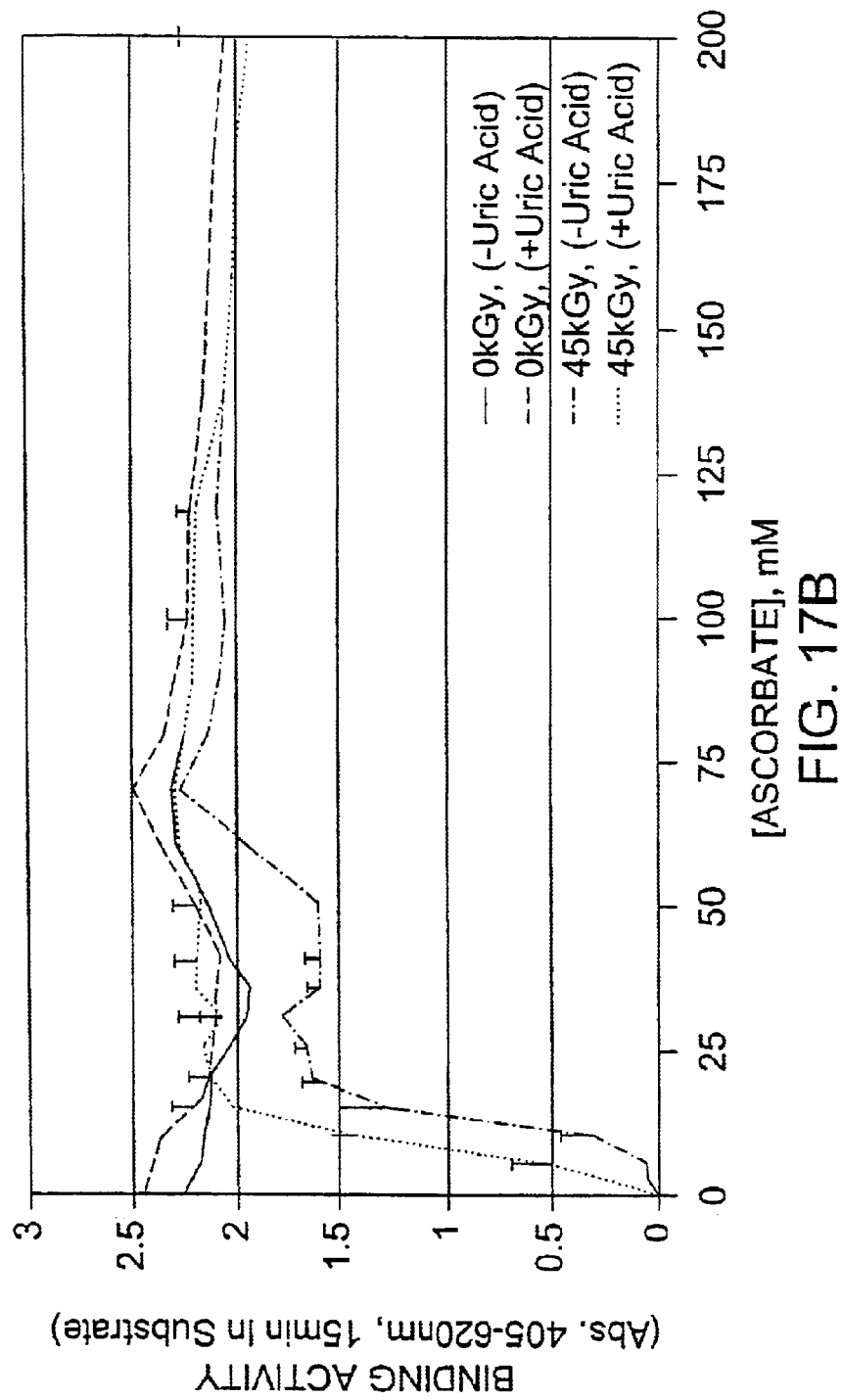
Figure 18A:
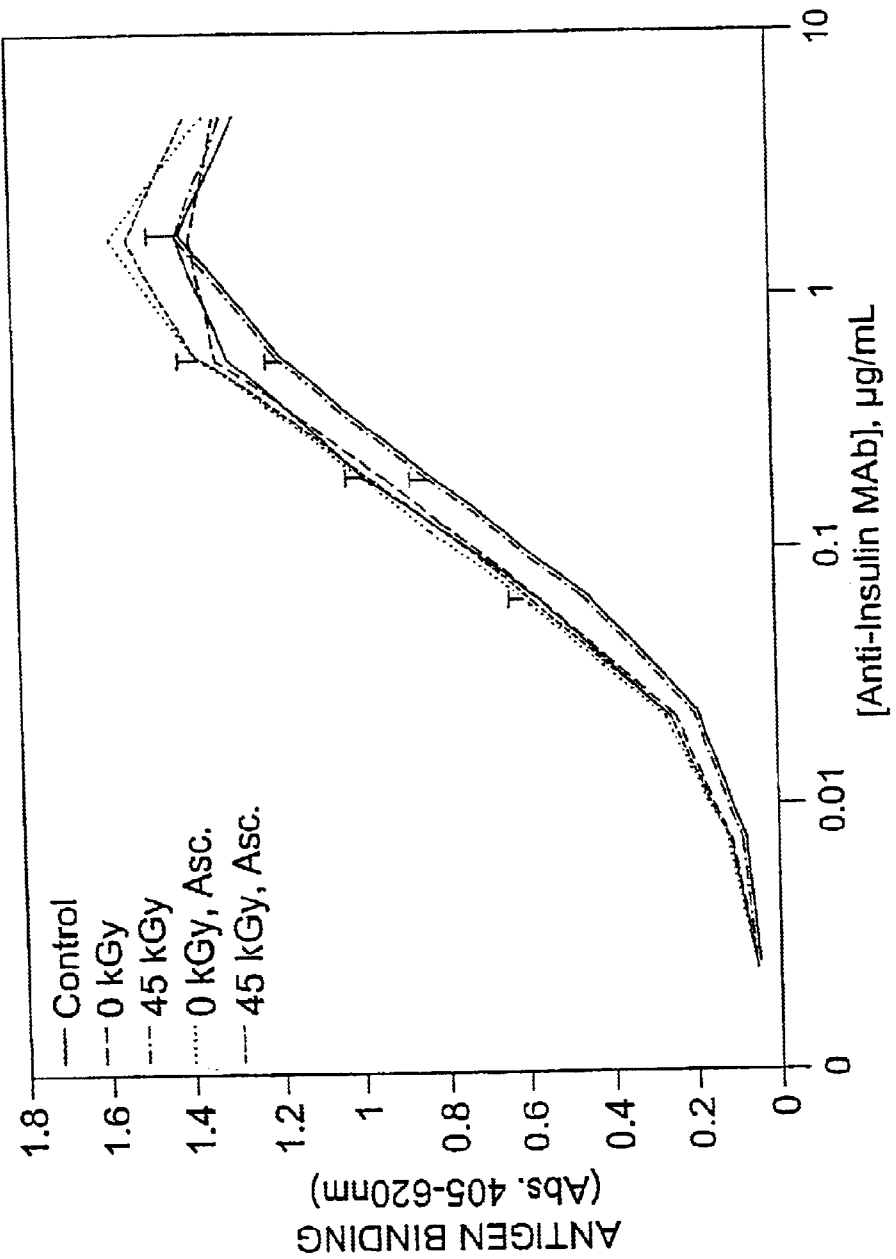
Figure 18B:
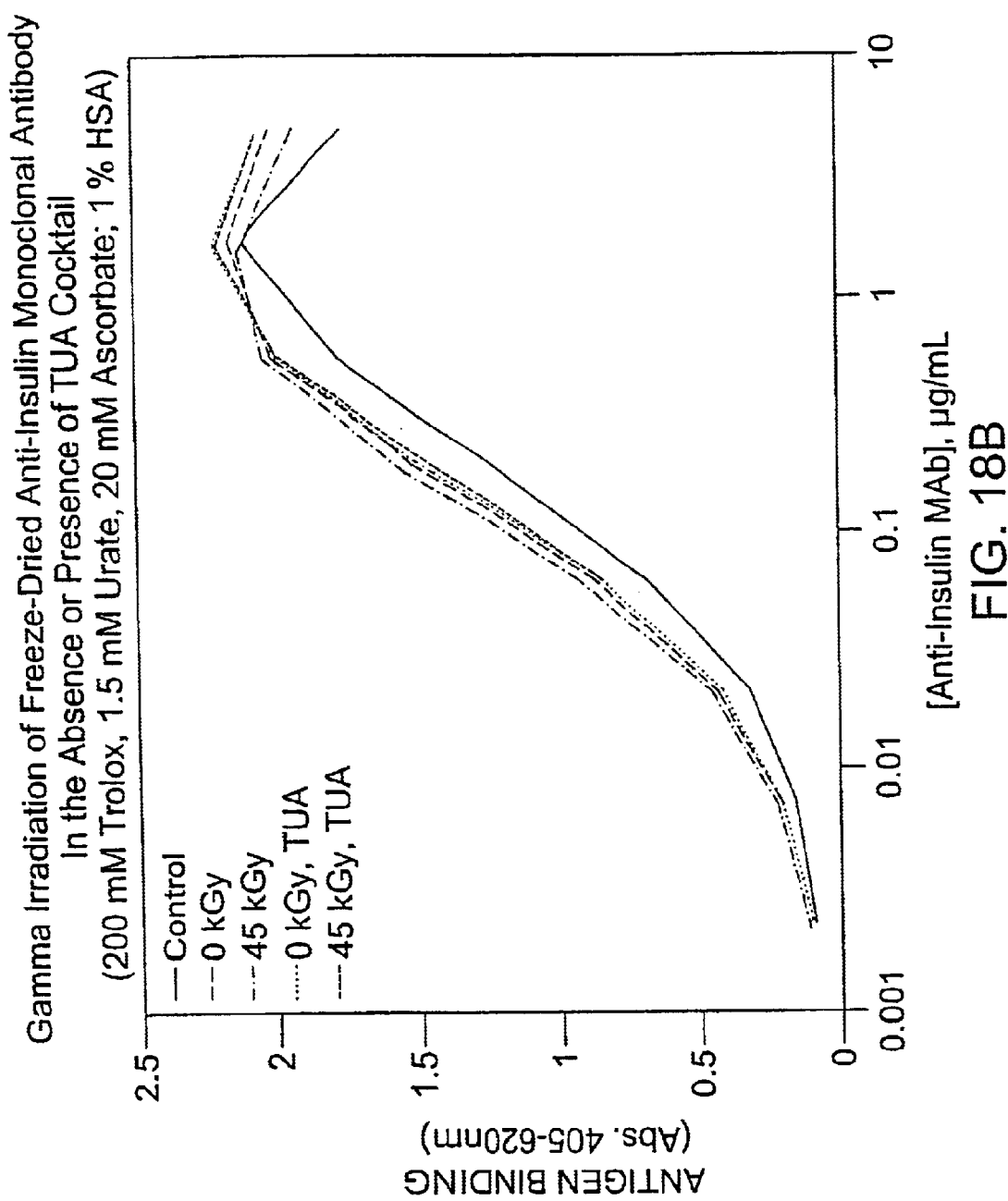
Figure 18D:
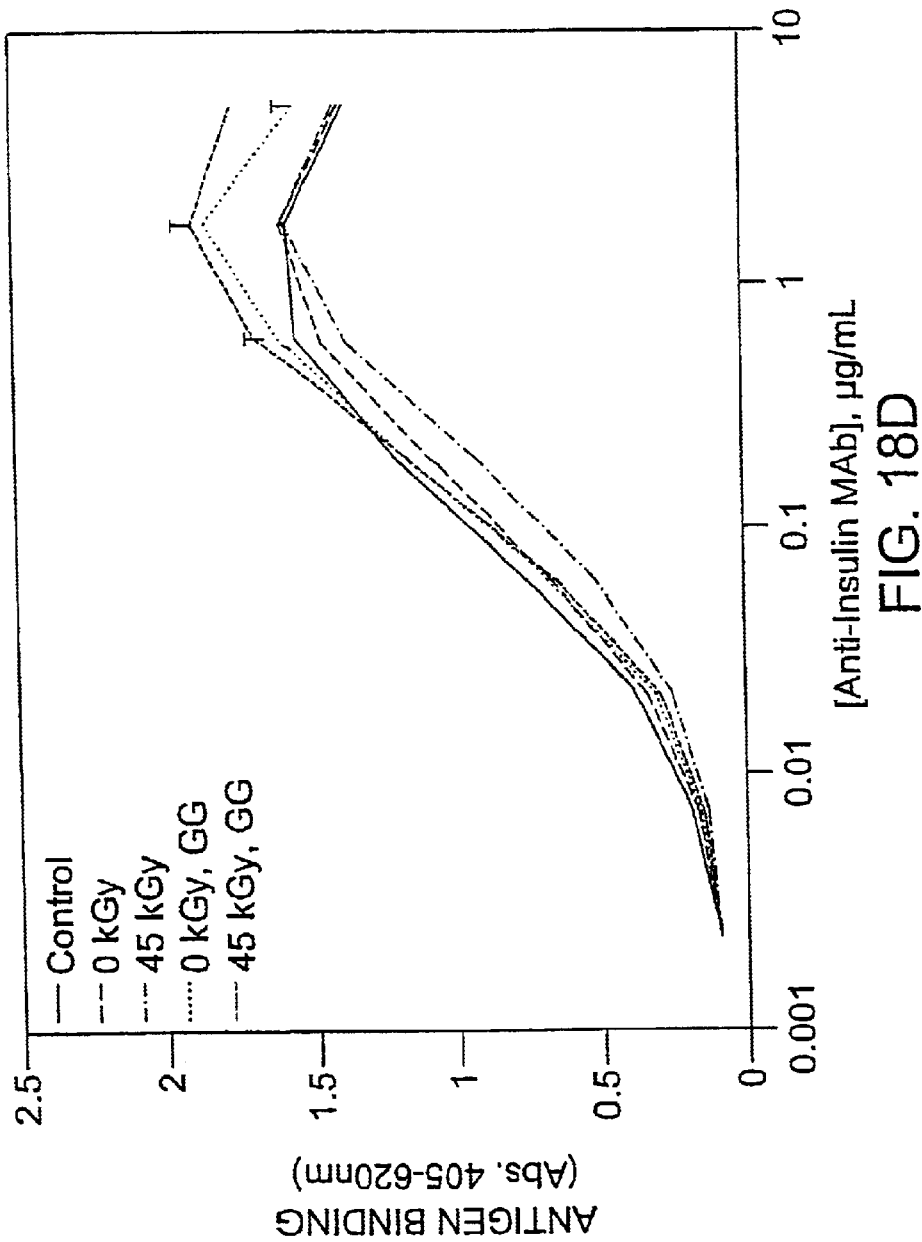
Figure 18E:
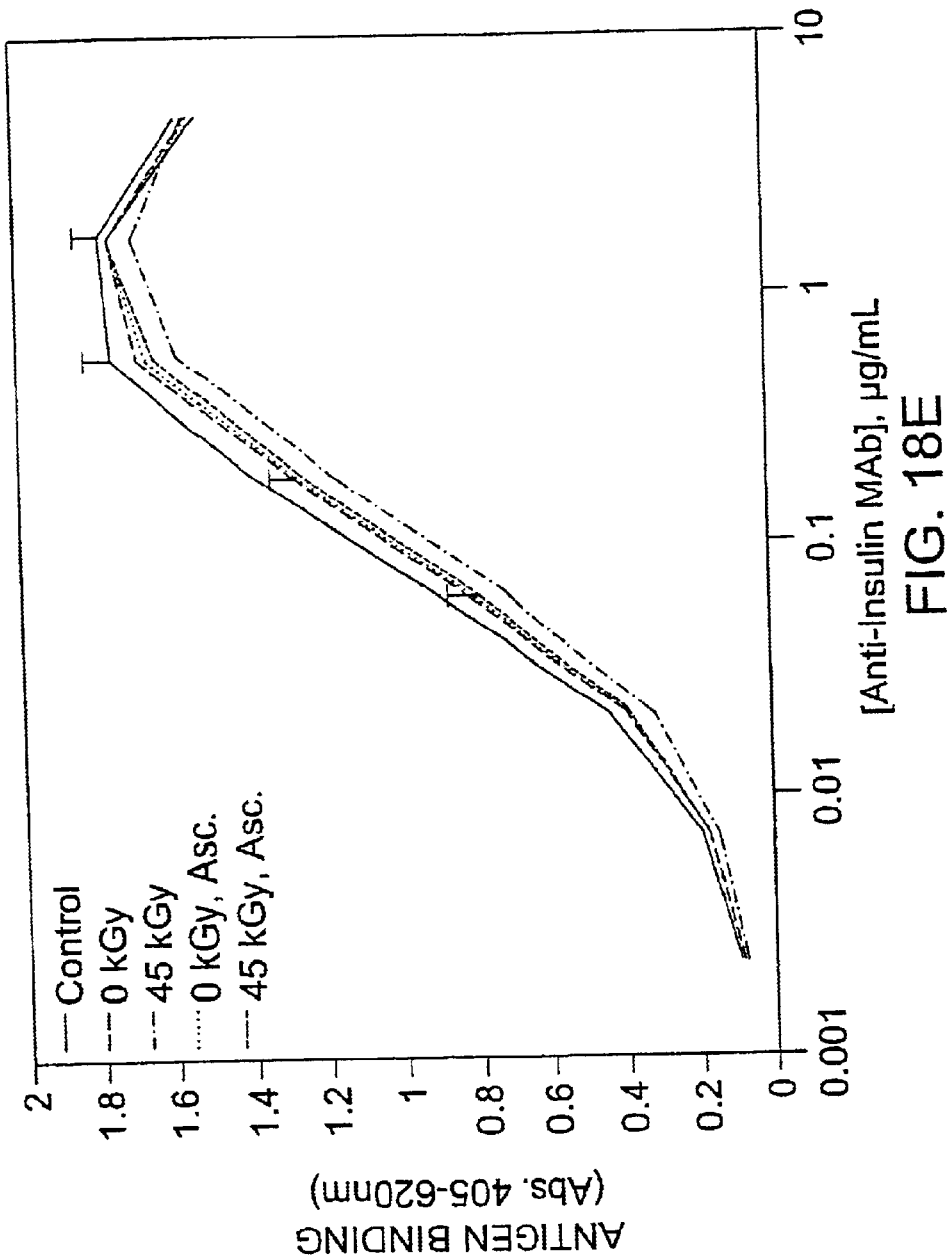
Figure 18F:
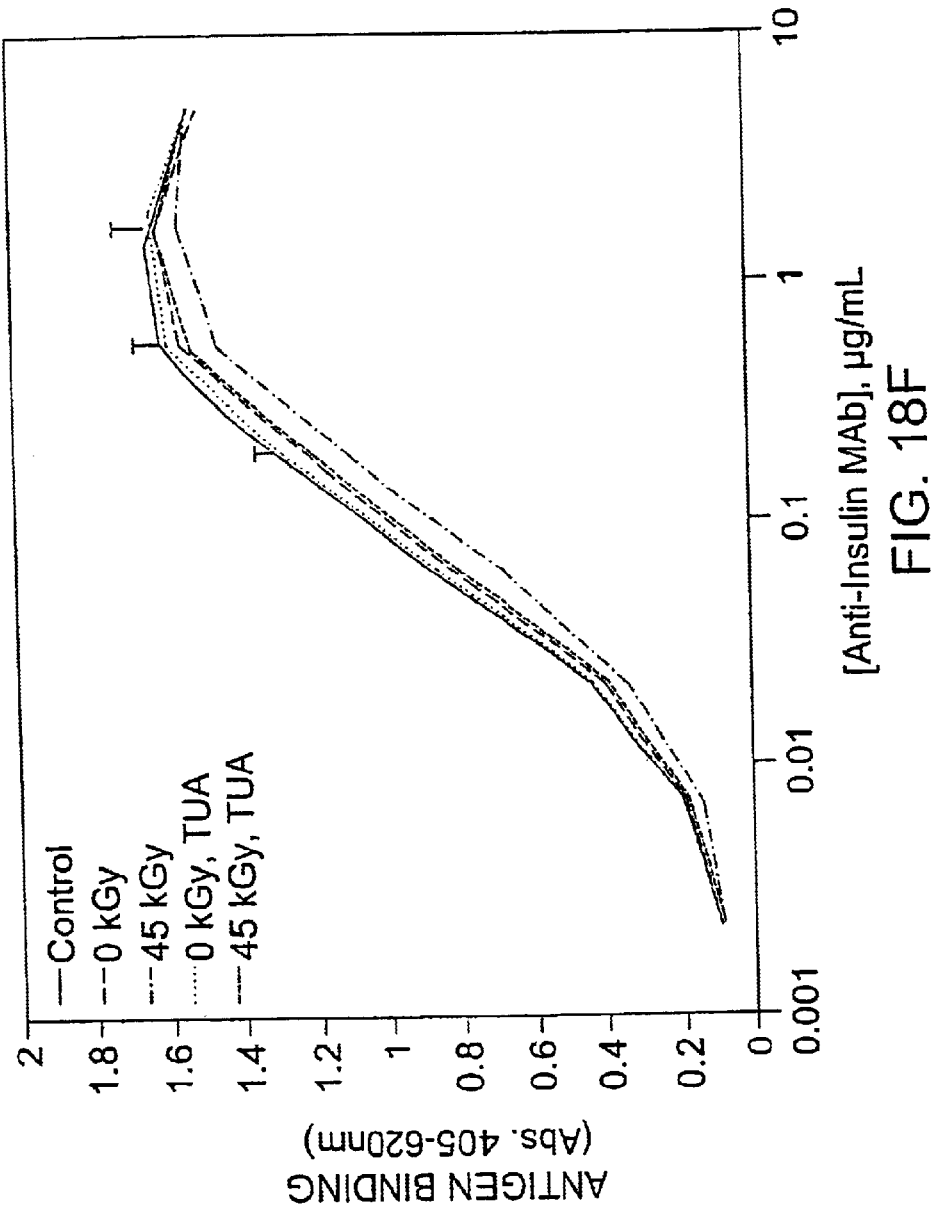
Figure 18G:
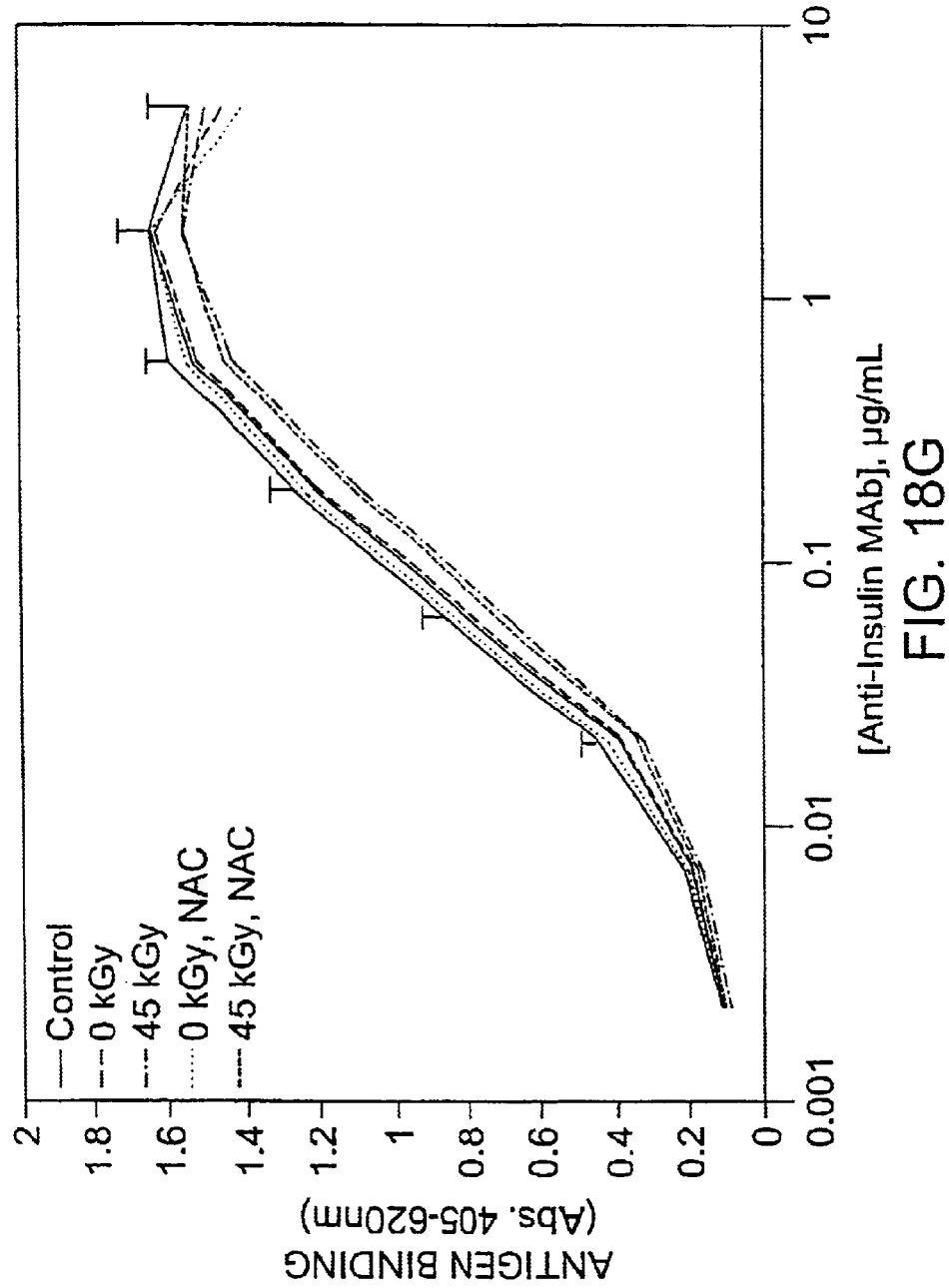
Figure 18H:
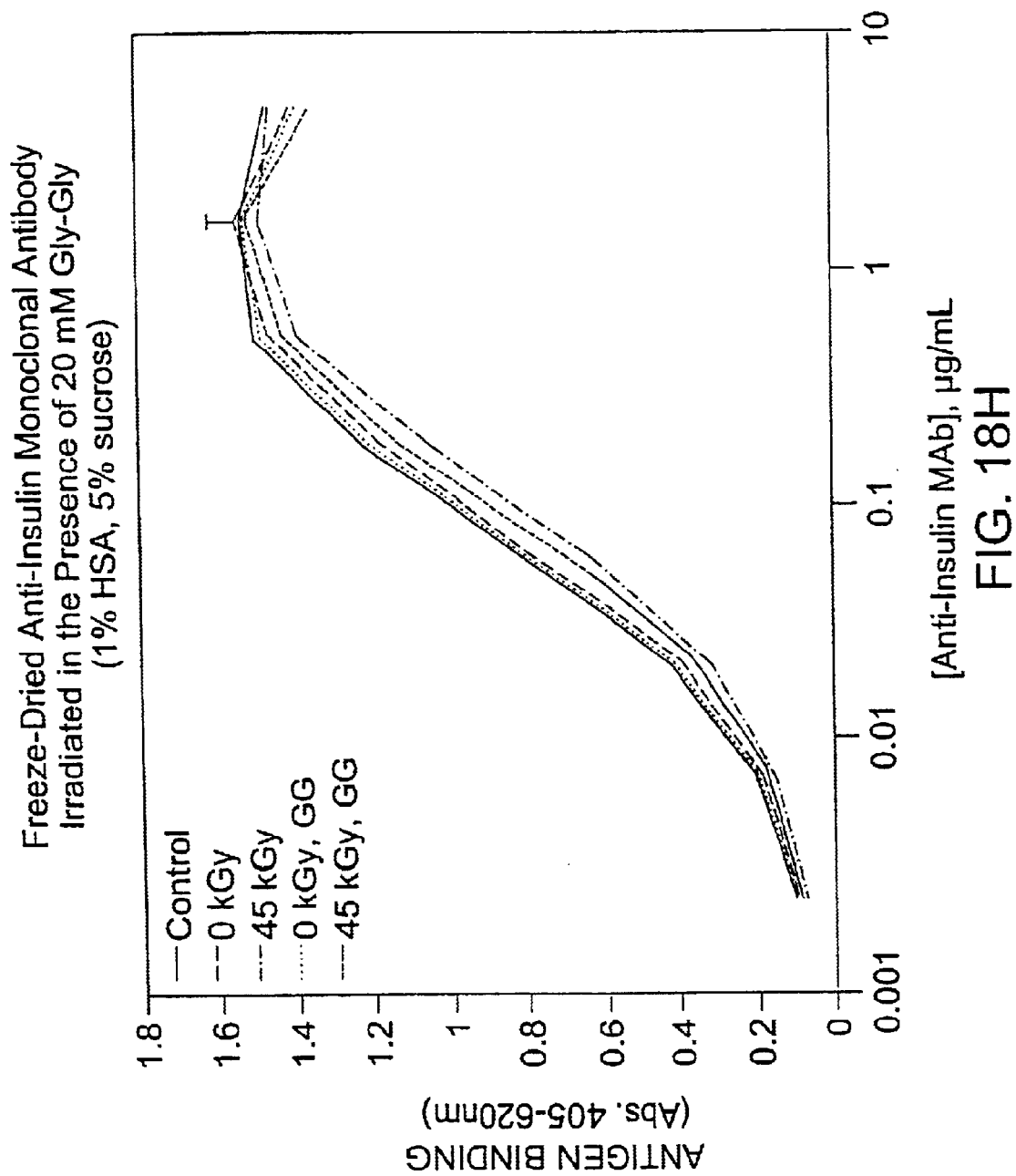
Figure 19B:
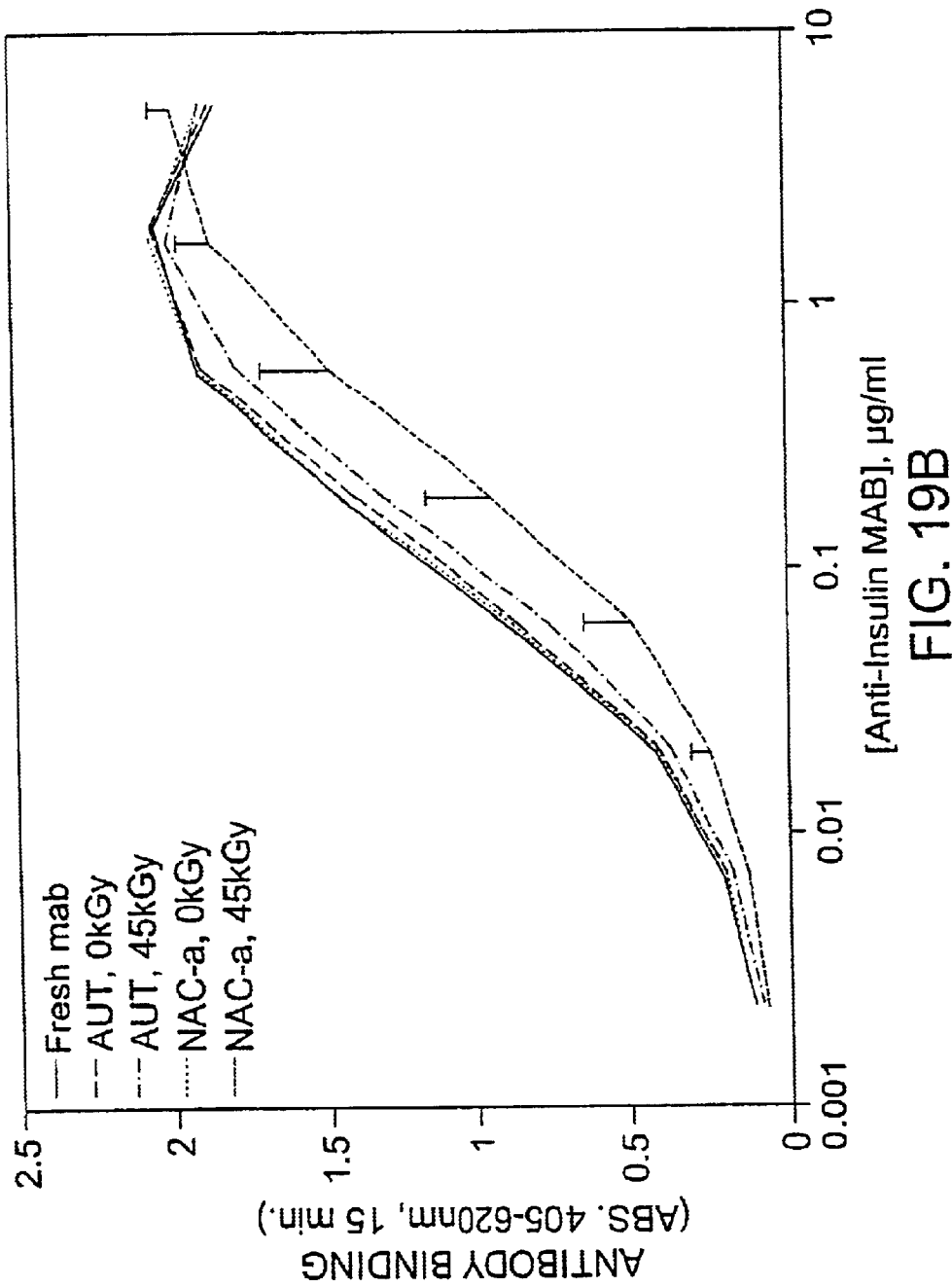
Figure 19C:
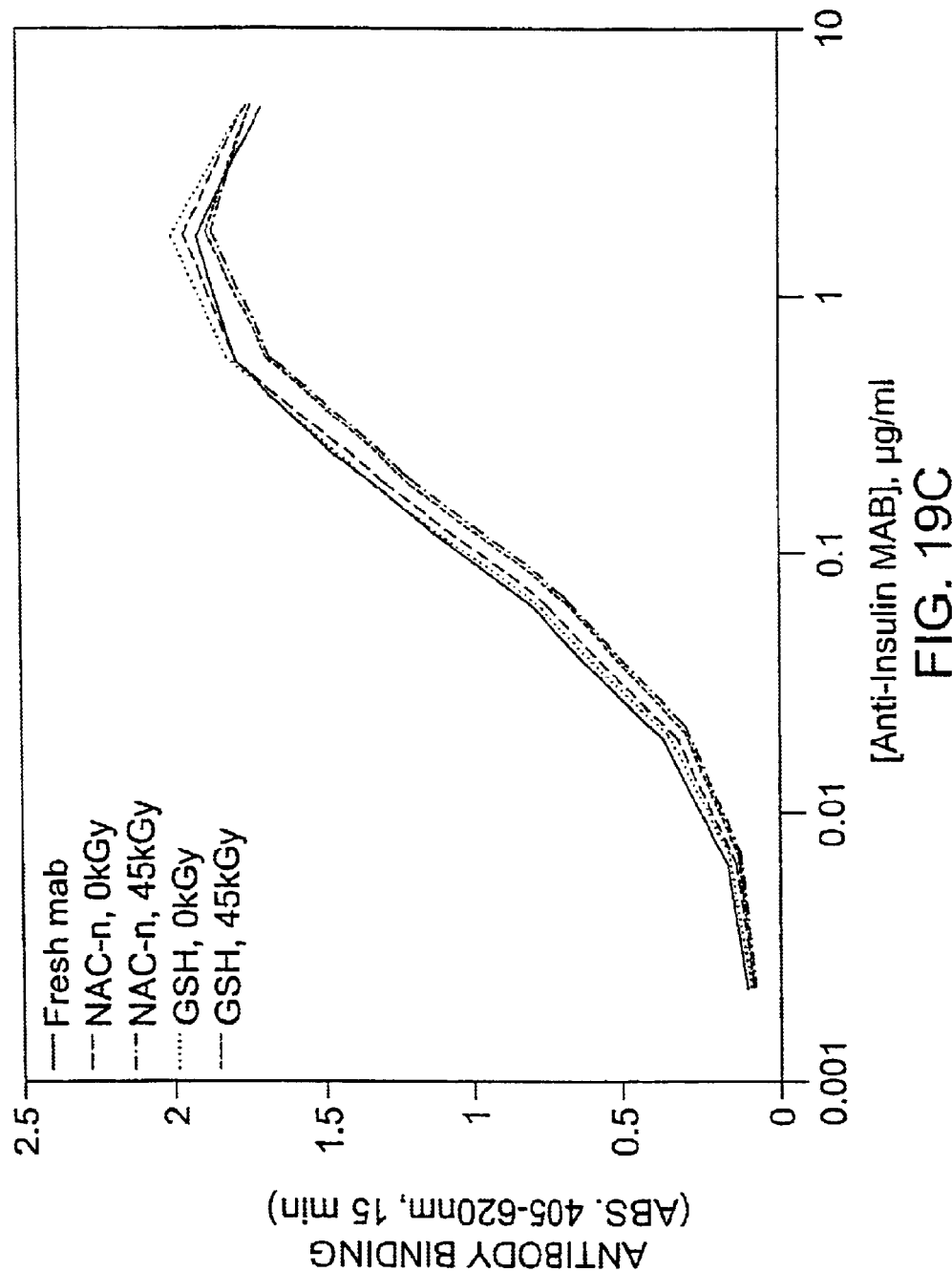
Figure 19E:
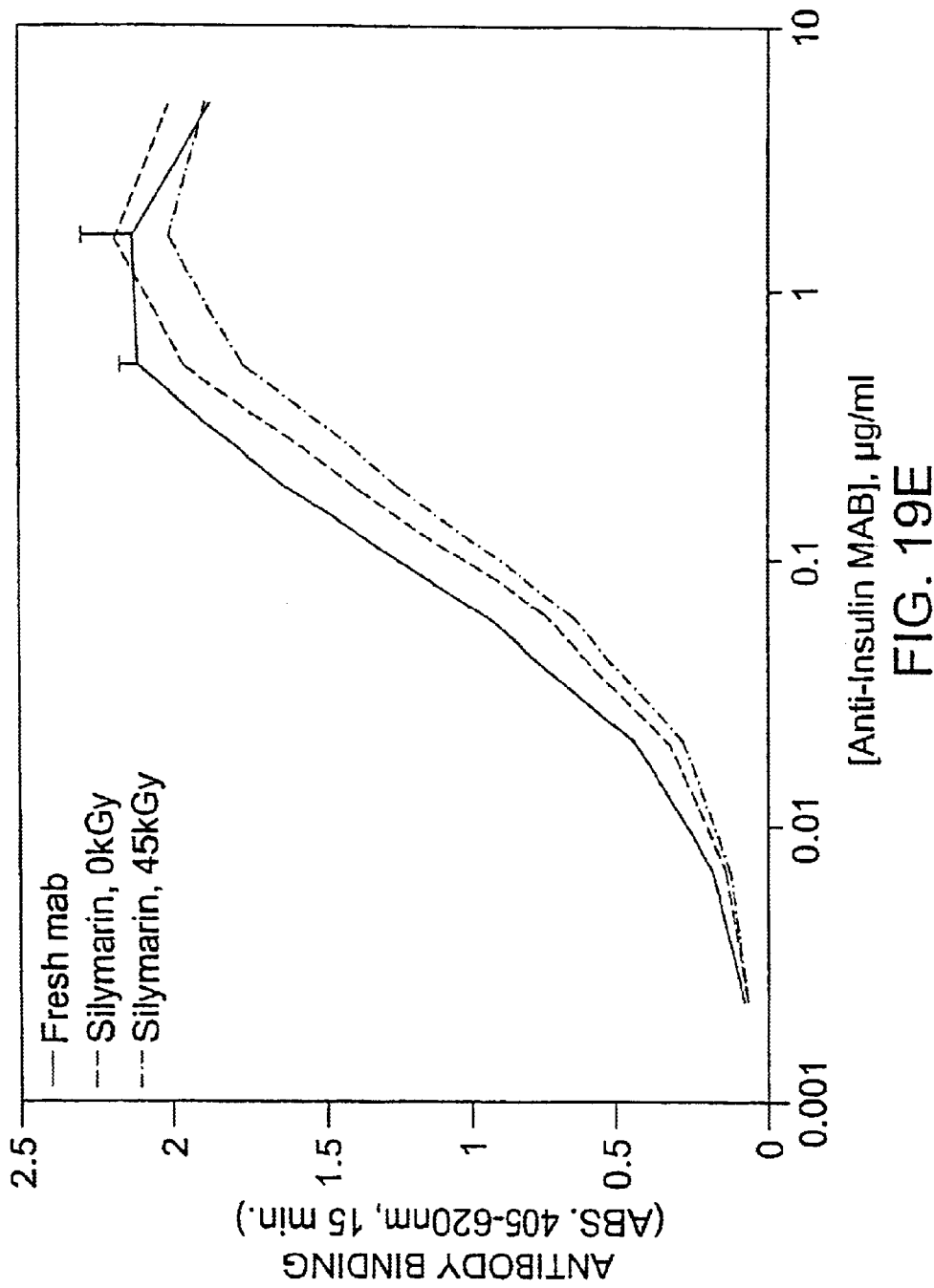
Figure 19F:
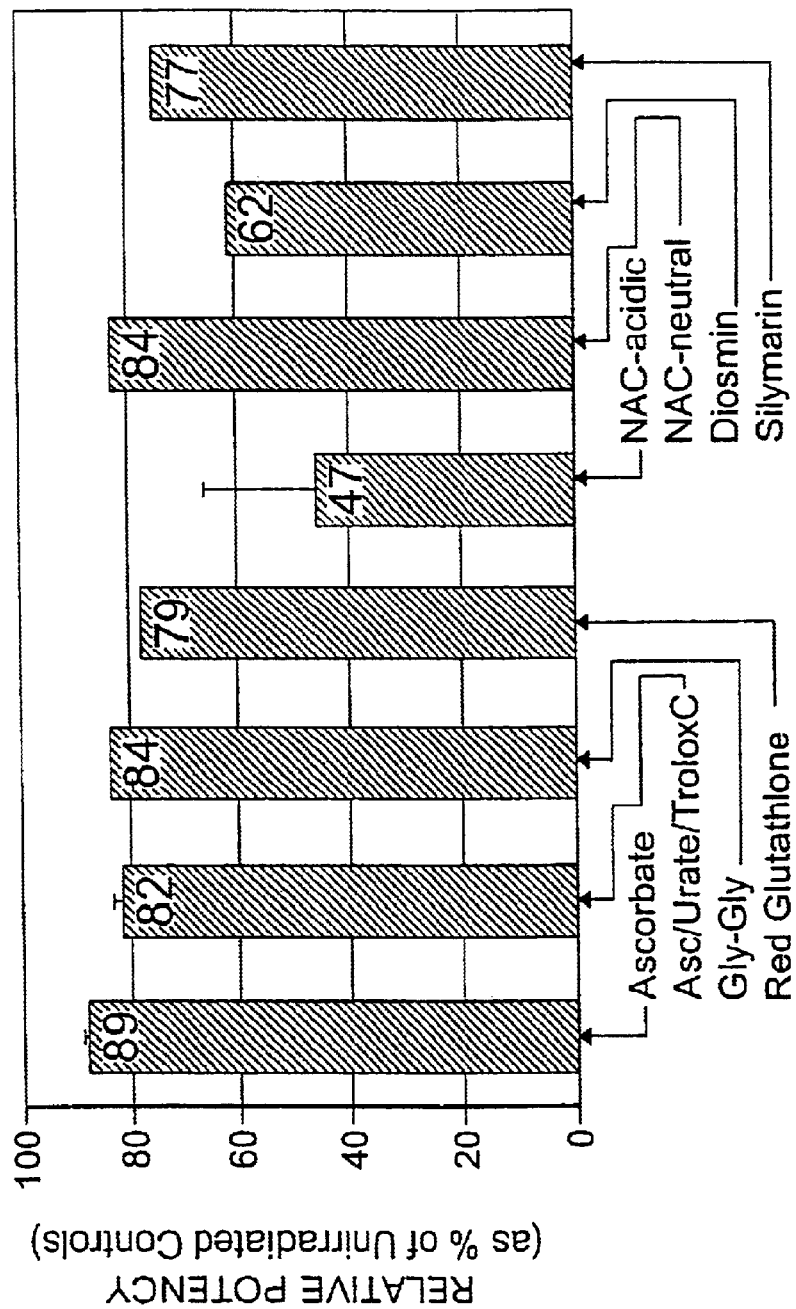

As illustrated in FIGS. 17A and 17B, the optimal concentration of sodium ascorbate necessary to provide maximum protection of immobilized anti-insulin monoclonal immunoglobulin in an aqueous environment (in the absence of uric acid) was determined to be approximately 70 mM. This contrasted with Example 8, which showed the optimal concentration of ascorbate to be approximately 150 mM. Approximately 100% recovery of anti-insulin binding activity was achieved in this example as opposed to approximately 50% recovery in Example 8. The addition of uric acid (2.25 mM) again resulted in a slight left shift of the ascorbate dose curve (~5 mM) and appeared to cause maximum recovery of activity to be achieved at a lower concentration of ascorbate (~25 mM). It was found that there is a biphasic nature to the irradiated samples without uric acid. Recovery improved significantly between 0–20 mM ascorbate, levelled off from 20–50 mM ascorbate, and then went up again until maximum recovery was observed at approximately 70 mM ascorbate.

Example 10

In this experiment, the protective effect of various stabilizers on gamma irradiated freeze-dried anti-insulin monoclonal immunoglobulin supplemented with 1% human serum albumin (HSA) and 5% sucrose was evaluated. The stabilizers tested were: ascorbate (20 mM); a mixture of trolox(200 mM), urate(1.5 uM), and ascorbate(20 mM); n-acetyl-l-cysteine(20 mM); reduced glutathione(20 mM); and the dipeptide, Gly-Gly(20mM).

Method

Samples were freeze-dried for approximately 64 hours and stoppered under vacuum and sealed with an aluminum, crimped seal. Samples were irradiated at a dose rate of 1.83–1.88 kGy/hr to a total dose of 45.1–46.2 kGy at 4° C.

Monoclonal immunoglobulin activity was determined by a standard ELISA protocol. Maxisorp plates were coated with human recombinant insulin at 2.5 µg/ml overnight at 4° C. The plate was blocked with 200 µl of blocking buffer (PBS, pH 7.4, 2% BSA) for two hours at 37° C. and then washed six times with wash buffer (TBS, pH 7, 0.05% TWEEN 20). Samples were re-suspended in 500 µl of high purity water (100 ng/µl), diluted to 5 µg/ml in a 300 µl U-bottomed plate coated for either overnight or two hours with blocking buffer. Serial 3-fold dilutions were performed, with a final concentration of 0.0022 µg/ml. Plates were incubated for one hour at 37° C. with agitation and then washed six times with a wash buffer. Phosphatase-labelled goat anti-mouse IgG (H+L) was diluted to 50 ng/ml in binding buffer and 100 µl was added to each well. The plate was incubated for one hour at 37° C. with agitation and washed six times with wash buffers. One hundred µl of Sigma-104 substrate (1 mg/ml in DEA buffer) was added to each well and reacted at room temperature. The plate was read on a Multiskan MCC/340 at 405 nM with the 620 nM absorbance subtracted.

Results

As shown in FIGS. 18A–18H, freeze-dried anti-insulin monoclonal immunoglobulin, supplemented with 1% HSA, gamma irradiated to 45 kGy resulted in an average loss in activity of 1.5 fold (average loss in avidity of 33%).

Samples irradiated to 45 kGy in the presence of stabilizers gave varying results:

20 mM ascorbate=~100% recovery 200 uM trolox, 1.5 mM urate, 20 mM ascorbate=~87% recovery 20 mM, n-acetyl-l-cysteine=~82% recovery 20 mM reduced glutathione=~76% recovery 20 mM Gly-Gly=~100% recovery Adding 5% sucrose to freeze-dried anti-insulin monoclonal immunoglobulin containing 1% HSA resulted in an average recovery of 70% of the activity in the sample irradiated to 45 kGy (average loss in activity of approximately 1.5 fold or approximately 30% loss in avidity).

The samples that radiated to 45 kGy in the presence of the aforementioned stabilizers had reduced activities upon addition of 5% sucrose:

20 mM ascorbate=~88% recovery 200 uM trolox, 1.5 mM urate, 20 mM ascorbate=~84% recovery 20 mM n-acetyl-l-cysteine=~72% recovery 20 mM reduced glutathione=~69% recovery 20 mM gly-gly=~79% recovery Similar results have been obtained upon the addition of 20 mM ascorbate, 20 mM Gly-Gly or the addition of 20 mM of both ascorbate and Gly-Gly to another monoclonal IgG preparation of different specificity (anti-Ig Lambda Light Chain).

Example 11

In this experiment, the protective effect of ascorbate(Asc, 20 mM), ascorbate(20 mM)/urate(1.5 mM)/trolox(200 uM) cocktail(AUT), n-acetyl-cysteine(neutral form: NAC-n, acidic form: NAC-a, both at 20 mM), Gly-Gly(20 mM), reduced glutathione(GSH, 20 mM), diosmin(39.3 uM) and silymarin(246 uM) on lyophilized anti-insulin monoclonal immunoglobulin was evaluated.

Method

In 3 ml glass vials, 1.0 ml total volume containing 100 µg anti-insulin monoclonal immunoglobulin, with 10 mg BSA (1%) and either no stabilizer or the stabilizer of interest was lyophilized. Samples were irradiated with gamma radiation (45 kGy total dose, dose rate 1.83 kGy/hr, temperature 4° C.) and then reconstituted with 1 ml of water. Karl Fischer moisture analysis was performed on the quadruplicate samples that did not contain immunoglobulin.

Immunoglobulin binding activity of independent duplicate samples was determined by a standard ELISA protocol: Maxisorp plates were coated overnight with 2.5 µg/ml insulin antigen. Three-fold serial dilutions of anti-insulin monoclonal immunoglobulin samples starting at 5 µg/ml were used. Goat anti-mouse phosphatase conjugate was used at 50 mg/ml. Relative potency values of irradiated samples compared to their corresponding unirradiated sample were calculated using the parallel line analysis software package (PLA 1.2 from Stegmann Systemberatung). Mass spectroscopy analysis was performed by M-scan, Inc. of Westchester Pa.

Results

As illustrated in FIGS. 19A–19F, irradiation of lyophilized anti-insulin monoclonal immunoglobulin in the presence of 1% bovine serum albumin resulted in the loss of approximately 30% avidity (relative to unirradiated samples) of the immunoglobulin for its immobilized antigen. The addition of ascorbate alone improved the recovery by 20%, such that there was approximately 90% avidity recovered after irradiation. The addition of ascorbate/urate/trolox cocktail, the dipeptide Gly-Gly, neutral n-acetyl-cysteine, reduced glutathione, or silymarin resulted in recovery of 77–84% avidity.

Similar results have been obtained upon the addition of 200 mM ascorbate, 200 mM Gly-Gly or the addition of 200 mM of both ascorbate and Gly-Gly to two other monoclonal IgG preparations of different specificity (anti-Ig Lambda Light Chain and anti-IgG1).

Example 12

In this experiment, the stability of anti-insulin monoclonal immunoglobulin irradiated in the liquid form in the presence or absence of ascorbate was evaluated.

Method

Anti-insulin monoclonal immunoglobulin was diluted to 1 mg/ml and irradiated at 4° C. in the presence or absence of 200 mM ascorbate to a total dose of 0, 15, or 45 kGy of gamma radiation.

Immunoglobulin binding activity of independent duplicate samples was determined by a standard direct ELISA protocol generally as described in the previous example.

Results

Figure 20A:
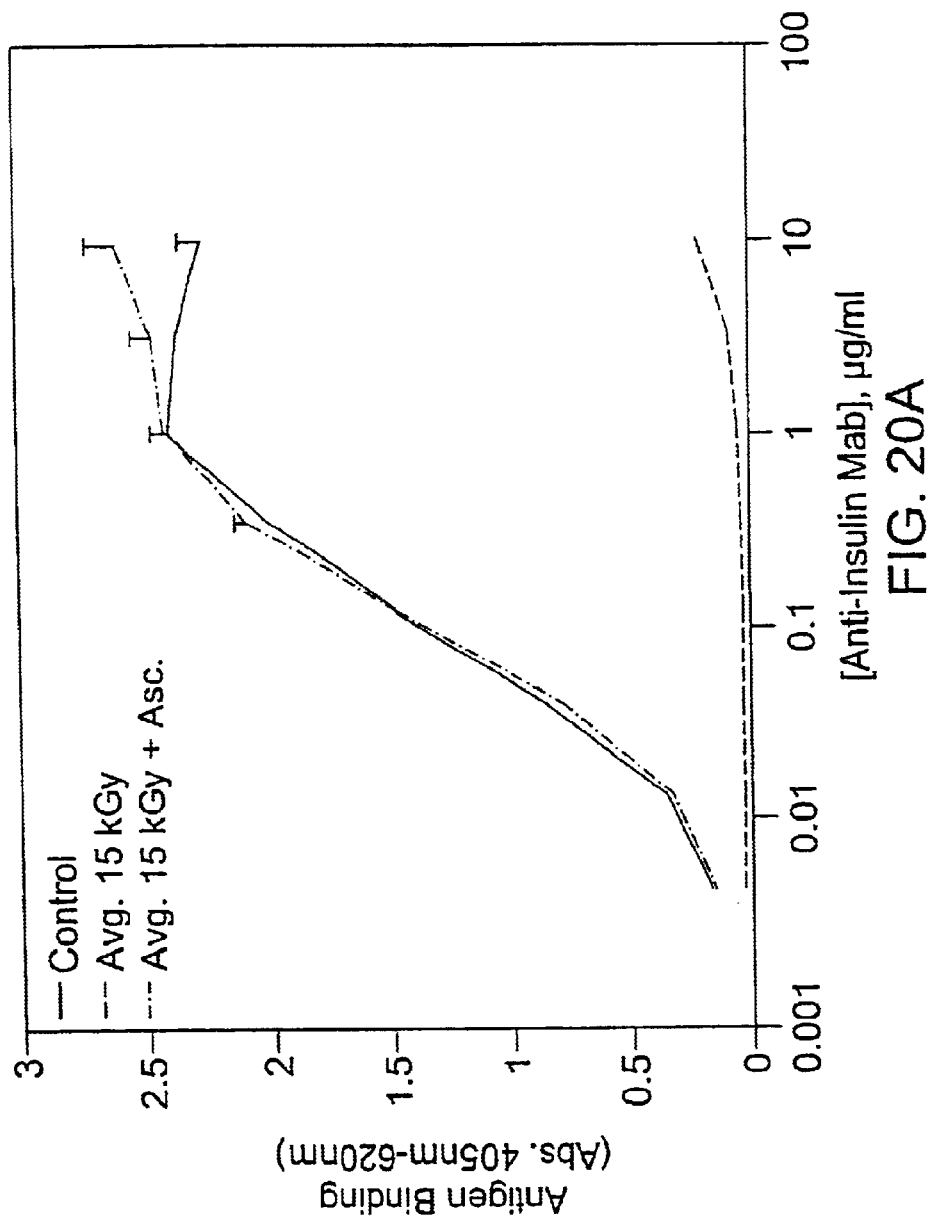
FIGS. 20A and 20B are graphs showing the effect of various doses of gamma radiation on anti-insulin monoclonal immunoglobulin, with and without ascorbate.
Figure 20B:
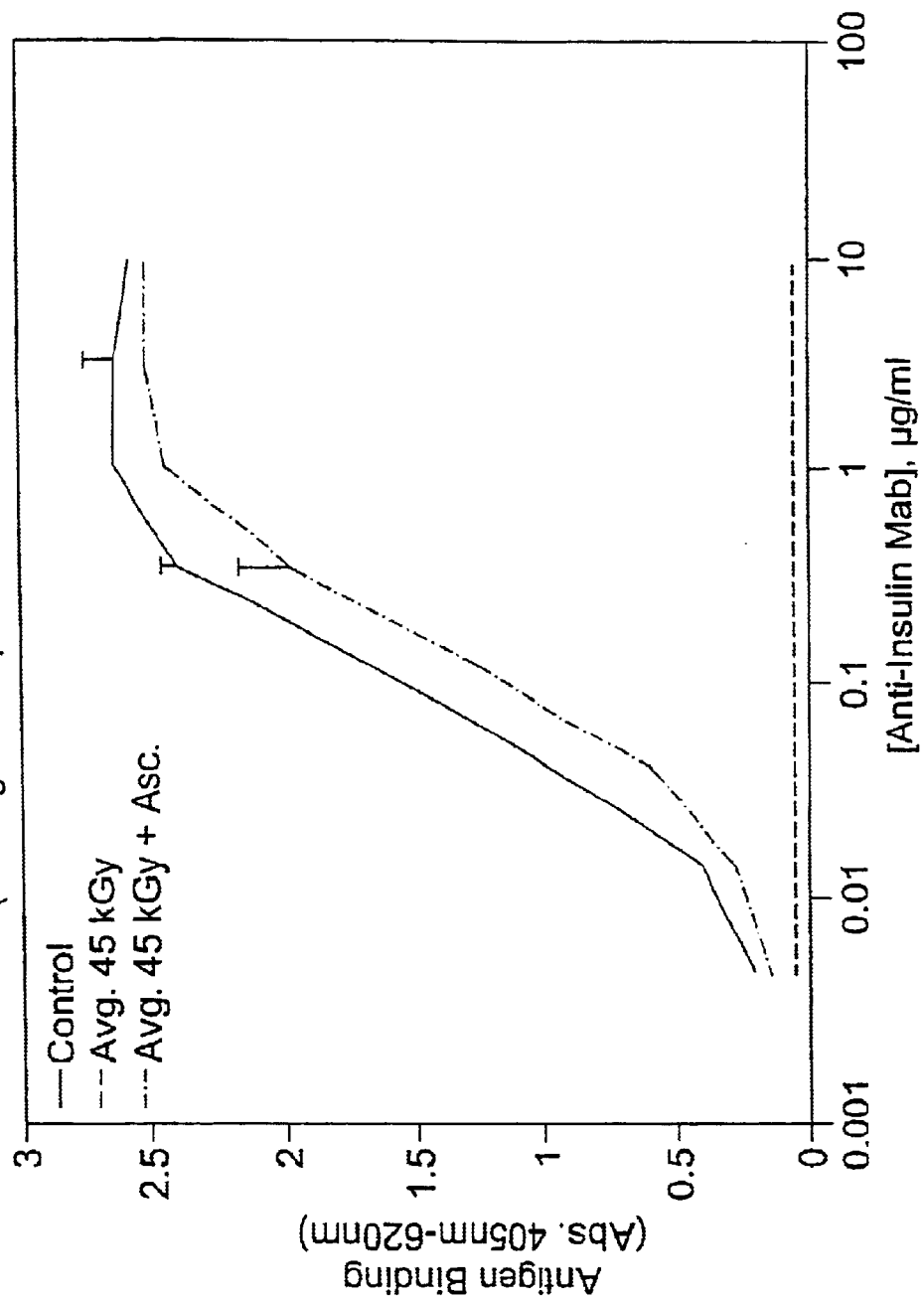

As shown in FIGS. 20A and 20B, the addition of 200 mM ascorbate resulted in recovery of 100% of immunoglobulin binding activity of samples irradiated with 15 kGy of radiation and recovery of 71.7% and 80.4% of the activity of samples radiated with 45 kGy of radiation compared to the in-house dilution control and the 0 kGy plus ascorbate control, respectively. As determined by polyacrylamide gel electrophoresis, irradiation of the anti-insulin immunoglobulins and the absence of the stabilizer resulted in protein aggregation as evidenced by high molecular weight bands on polyacrylamide gels. Additionally, a significant loss of material was apparent. The addition of 200 mM ascorbate had a protective effect on the immunoglobulins irradiated at 15 kGy and 45 kGy, as demonstrated by the recovery of an intact $IgG_1$ band and as well as heavy and light chain bands.

When duplicates of the 15 kGy plus 200 mM ascorbate samples were averaged, the antigen binding activity was not significantly different from that of the dilution control. In contrast, irradiating the samples containing ascorbate to 45 kGy resulted in an average 2- and 2.5-fold decrease in avidity when compared to the in-house dilution control and stock control, respectively. The SDS-PAGE analysis indicated that in the absence of ascorbate, irradiating the anti-insulin monoclonal immunoglobulins resulted in significant loss of material and a generation of high molecular weight aggregate. The addition of 200 mM ascorbate prevented aggregate formation and resulted in recovery of approximately 80% and approximately 50% of the immunoglobulins following irradiation to 15 kGy and 45 kGy, respectively.

Example 13

This experiment was conducted to determine whether low pH (4.5) diminishes the stabilizing effect of L-ascorbic acid on monoclonal immunoglobulin irradiated to 45 kGy with gamma radiation.

Method

An anti-human insulin monoclonal Ig (Anti-Human Insulin Monoclonal Immunoglobulin, Purified Clone #7F8; BioDesign International #E86102M, lot 7125000) was irradiated as a liquid at a rate of 1.774 kGy/hr ($^{60}$Co) in the presence and absence of 200 mM L-Ascorbic acid to a total dose of 45kGy, at pH 6.8 and 4.5. Following irradiation, the samples were assayed for their antigen-specific binding capability in an ELISA assay using insulin-coated plates as targets. Structural analysis of the Ig was done via standard SDS-PAGE electrophoresis under both reduced and non-reduced conditions.

Results

Figure 21A:
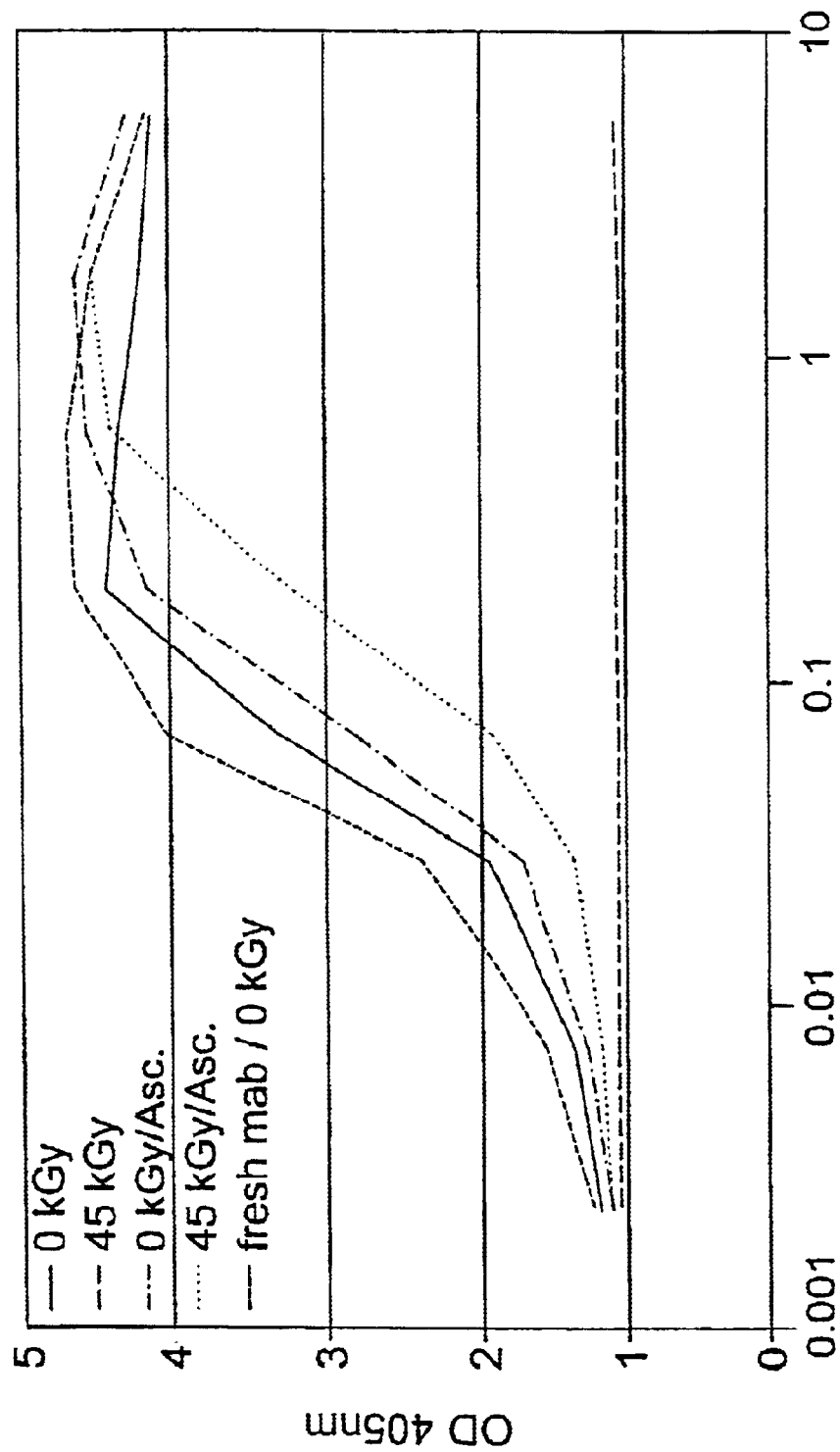

As illustrated in FIGS. 21A and 21B, the ELISA functional assay results clearly show that recovery of the monoclonal immunoglobulin in the presence of ascorbate is not dependent on pH. The graphs for pH 6.8 and 4.5 are virtually superimposable. A slight loss of activity is seen at both pH values upon the addition of ascorbic acid and again following irradiation, however the magnitude of this reduction is small in comparison to the complete loss of activity seen when irradiation takes place in the absence of ascorbate.

SDS-PAGE electrophoresis gels showed a complete destruction of the immunoglobulin at 45 kGy in the absence of ascorbic acid at both pH 3.8 and pH 4.5. The addition of 200 mM ascorbic acid maintained the same apparent structure upon irradiation. A pH of 4.5 may have inhibited aggregation.

These results indicate that, in the presence of 200 mM ascorbic acid, monoclonal Ig can be irradiated to at least 45 kGy while retaining structure and activity at both pH 6.7 and 4.5.

Example 14

In this experiment the level of viral inactivation and monoclonal immunoglobulin activity retention in anti-insulin monoclonal immunoglobulin infected with porcine parvovirus (PPV) irradiated with $^{60}$Co gamma radiation at an approximate rate of 1.8 kGy/hour at 4° C. was evaluated.

Method

PPV was utilized as a model virus for Human Parvovirus B19, a non-enveloped virus that is considered the most difficult virus of concern in human-sourced biologics and a close analog of the other members of the Parvovirus family that are also considered the most difficult viruses of concern in animal-sourced biologics.

A high titre PPV stock was spiked into a preparation of a monoclonal immunoglobulin directed against insulin. A protectant, (sodium ascorbate) was added to some samples at a final concentration of 200 mM.

The samples to be irradiated were exposed to $^{60}$Co radiation at an approximate rate of 1.8 kGy/hour at 4° C.

After irradiation of some of the samples, aliquots of the spiked samples were taken and used to titre the amount of remaining infective virus particles. Briefly, the samples were assayed in a viral detection bioassay known as a Cytopathic Effect test (CPE). A cell line capable of being infected by the PPV virus and lysed by it (Porcine Kidney cells, also known as PK-13 cells) were added to 96-well assay plates to form a monolayer of approximately 70% confluence. Quadruplicate aliquots of the samples were added to the wells in a limiting-dilution series (5-fold dilutions). The plates were then incubated for 7–8 days and then examined to determine if viable cells remained in the wells. The resulting data was analysed using a Limiting-Dilution method as described by Karber to determine the viral titer which is shown in the accompanying Figure as $Log_{10}TCID_{50}$ Titer per 0.1 ml.

Results

Figure 22:
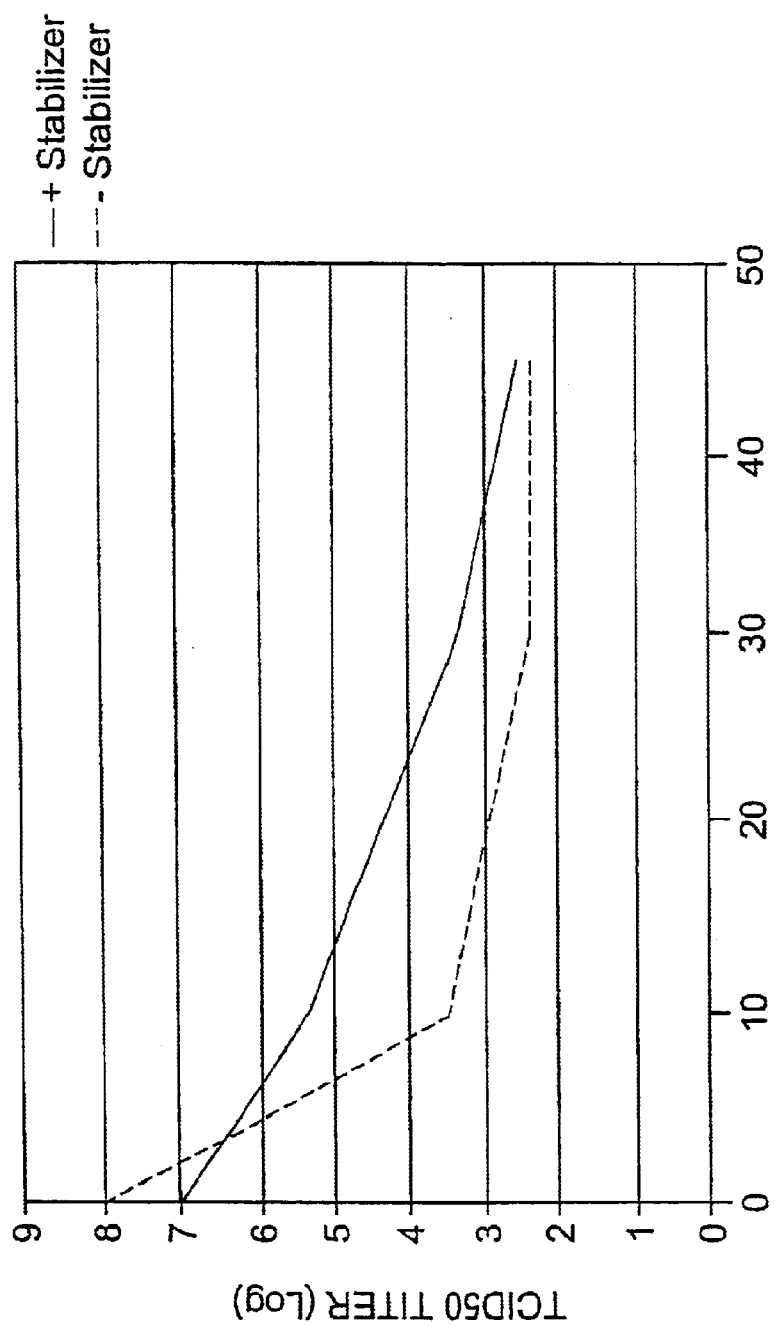
FIG. 22 is a graph showing the level of viral inactivation by irradiation with gamma radiation of an anti-insulin monoclonal immunoglobulin contaminated with porcine parvovirus (PPV).

As shown in Table 4 below and in FIG. 22, the application of gamma radiation effectively inactivated the virus in a dose-dependent manner. The addition of 200 mM sodium ascorbate to the monoclonal immunoglobulin resulted in a significant reduction in the viral inactivation at lower doses, but at higher doses this effect was much smaller. The application of 45 kGy of gamma radiation to samples containing ascorbate resulted in greater than 4 logs of viral inactivation.

TABLE 4

| γ Radiation Dose | Ascorbate | $TCID_{50}$ Titre/0.1 ml | $Log_{10}$ Reduction of Viral Titre |
|---|---|---|---|
| 0 kGy | − | 7.075 | |
| " | + | 7.95 | |
| 10 kGy | − | 5.4125 | 1.66 |
| " | + | 3.575 | 4.375 |
| 30 kGy | − | 3.4 | 3.675 |
| " | + | 2.35 | 5.6 |
| 45 kGy | − | 2.525 | 4.55 |
| " | + | 2.35 | 5.6 |

Example 15

This experiment was conducted to evaluate the level of activity retention achieved when irradiating monoclonal immunoglobulins in both liquid and lyophilized forms with e-beam radiation in the presence or absence of sodium ascorbate.

Method

Anti-Insulin $IgG_1$ was tested in liquid and after having been lyophilized. Samples were prepared both with and without 200 and 20 mM sodium ascorbate in the liquid and lyophilized state respectively.

The samples to be irradiated (both with and without ascorbate) were exposed to e-beam irradiation at an approximate rate of 45 kGy/hour at 77–88° F. The e-beam energy was 7 MeV and a total dose of approximately 45 kGy was given. Control samples consisted of unirradiated samples with and without ascorbate that traveled to and from the irradiation site, and a reference control sample that did not travel to the irradiation site. During transport the samples were kept at 4° C. The samples are shown in Table 5 below:

TABLE 5

Samples

| Sample Name | Physical State | Ascorbate | Travel to Irradiator | e-Beam Dose (kGy) |
|---|---|---|---|---|
| Fresh Ig | Liquid | | | 0 |
| L-I/0 | Liquid | | ✓ | 0 |
| L-I/45 | " | | ✓ | 45 |
| L-I/A/0 | " | ✓ | ✓ | 0 |
| L-I/A/45 | " | ✓ | ✓ | 45 |
| Fresh Ig | Lyophilized | | | 0 |
| fd-I/0 | Lyophilized | | ✓ | 0 |
| fd-I/45 | " | | ✓ | 45 |
| fd-I/A/0 | " | ✓ | ✓ | 0 |
| fd-I/A/45 | " | ✓ | ✓ | 45 |

After irradiation the lyophilized samples were reconstituted with distilled water. All samples were then tested in an anti-human insulin ELISA assay as described in Example 10. Approximate measures of the recovery of antigen-binding activity were performed by hand as the concentration of Ig that produced approximately 50% of the maximum OD.

Results

As seen Table 6 below, when in the liquid state the application of E-beam radiation completely inactivated the Ig. In the presence of ascorbate, there was a clear recovery of activity, but the magnitude was limited.

Figure 23A:
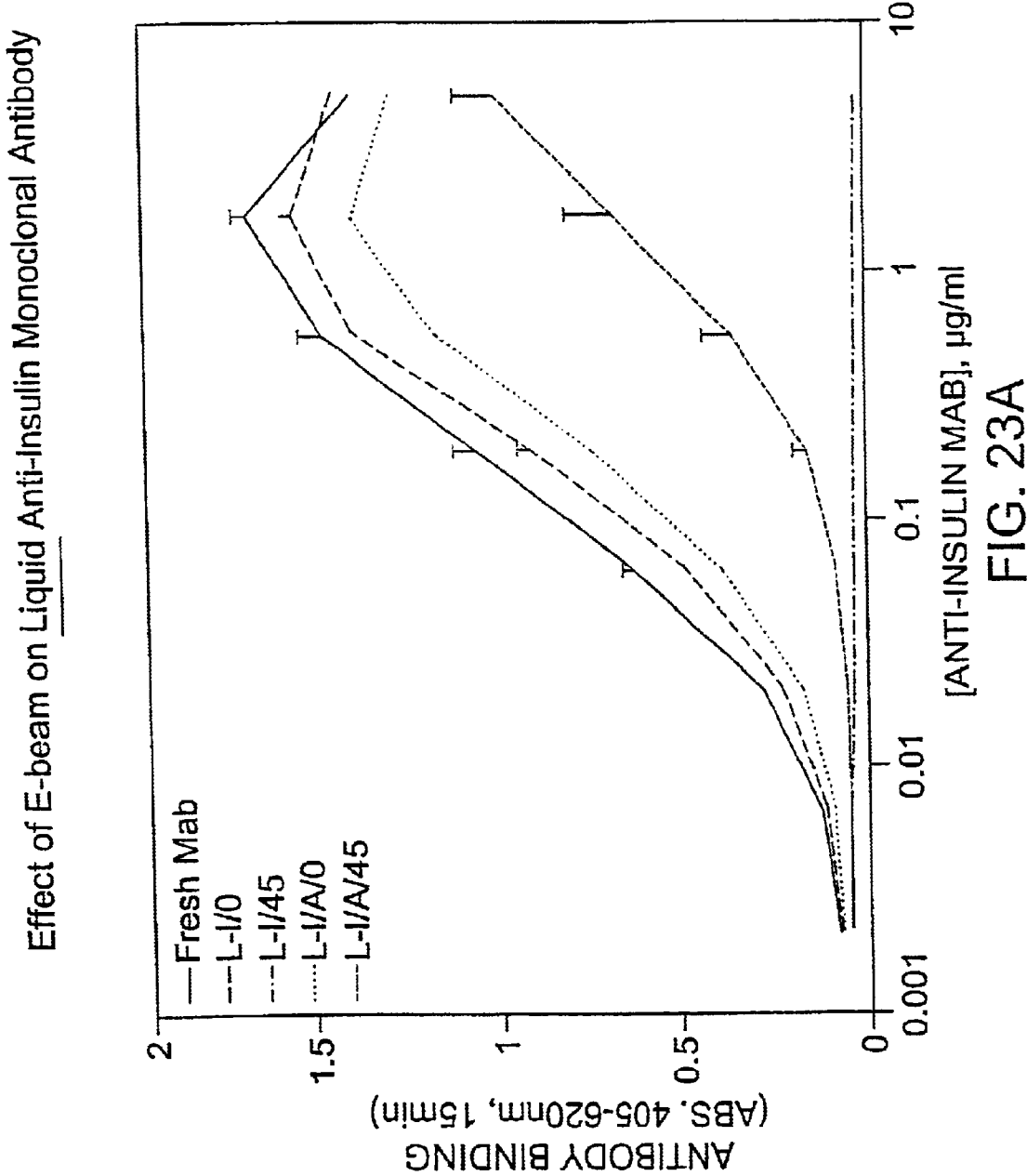

The lyophilization of the Ig prior to irradiation had a greater effect upon the recovery of activity than the addition of ascorbate alone to the liquid. Approximately 50% of the antigen-binding activity was retained when ascorbate-free Ig was irradiated. The addition of 20 mM ascorbate prior to lyophilization resulted in complete recovery of activity. The results of the ELISA are shown in FIGS. 23A and 23B.

TABLE 6

Approximate Antigen-Binding Activity

| Sample Name | Physical State | e-Beam Dose (kGy) | ≈50% of Max $OD_{405-620}$ | ≈ % Recovery of Activity |
|---|---|---|---|---|
| Fresh Ig | Liquid | 0 | 0.065 | |
| L-I/0 | Liquid | 0 | 0.12 | 100 |
| L-I/45 | " | 45 | ∞ | 0 |
| L-I/A/0 | " | 0 | 0.18 | 100 |
| L-I/A/45 | " | 45 | 1.8 | 10 |
| Fresh Ig | Lyophilized | 0 | 0.17 | |

TABLE 6-continued

Approximate Antigen-Binding Activity

| Sample Name | Physical State | e-Beam Dose (kGy) | ≈50% of Max $OD_{405-620}$ | ≈ % Recovery of Activity |
|---|---|---|---|---|
| fd-I/0 | Lyophilized | 0 | 0.21 | 100 |
| fd-I/45 | " | 45 | 0.45 | 50 |
| fd-I/A/0 | " | 0 | 0.22 | 100 |
| fd-I/A/45 | " | 45 | 0.21 | 100 |

Having now fully described this invention, it will be understood to those of ordinary skill in the art that the methods of the present invention can be carried out with a wide and equivalent range of conditions, formulations, and other parameters without departing from the scope of the invention or any embodiments thereof. All patents and publications cited herein are hereby fully incorporated by reference in their entirety. The citation of any publication is for its disclosure prior to the filing date and should not be construed as an admission that the present invention is not entitled to antedate such publication by virtue of prior invention.

What is claimed is:

1. A method for sterilizing a preparation of monoclonal immunoglobulins that is sensitive to radiation and has a residual solvent content, said method comprising:

(i) reducing said residual solvent content of a preparation of monoclonal immunoglobulins to a level effective to protect said preparation of monoclonal immunoglobulins from said radiation; and (ii) irradiating said preparation of monoclonal immunoglobulins with gamma radiation at an effective rate for a time effective to sterilize said preparation of monoclonal immunoglobulins, wherein the pH of said preparation of monoclonal immunoglobulins is less than 7.

2. A method for sterilizing a preparation of monoclonal immunoglobulins that is sensitive to radiation, said method comprising:

(i) adding to a preparation of monoclonal immunoglobulins at least one stabilizer in an amount effective to protect said preparation of monoclonal immunoglobulins from said radiation; and (ii) irradiating said preparation of monoclonal immunoglobulins with gamma radiation at an effective rate for a time effective to sterilize said preparation of monoclonal immunoglobulins wherein the pH of said preparation of monoclonal immunoglobulins is less than 7.

3. A method for sterilizing a preparation of monoclonal immunoglobulins that is sensitive to radiation, said method comprising:

(i) adding to a preparation of monoclonal immunoglobulins at least one stabilizer in an amount effective to protect said preparation of monoclonal immunoglobulins from said radiation; and (ii) irradiating said preparation of monoclonal immunoglobulins with gamma radiation at a low rate for a time effective to sterilize said preparation of monoclonal immunoglobulins wherein the pH of said preparation of monoclonal immunoglobulins is less than 7.

4. A method for sterilizing a preparation of monoclonal immunoglobulins that is sensitive to radiation and has a residual solvent content, said method comprising:

(i) reducing said residual solvent content of a preparation of monoclonal immunoglobulins to a level effective to protect said preparation of monoclonal immunoglobulins from said radiation; and (ii) irradiating said preparation of monoclonal 15 immunoglobulins with gamma radiation at a low rate for a time effective to sterilize said preparation of monoclonal immunoglobulins, wherein the pH of said preparation of monoclonal immunoglobulins is less than 7.

5. A method for sterilizing a preparation of monoclonal immunoglobulins that is sensitive to radiation and has a residual solvent content, said method comprising:

(i) reducing said residual solvent content of a preparation of monoclonal immunoglobulins to a level effective to protect said preparation of monoclonal immunoglobulins from said radiation;

(ii) adding to said preparation of monoclonal immunoglobulins at least one stabilizer in an amount effective to protect said preparation of monoclonal immunoglobulins from said radiation; and (iii) irradiating said preparation of monoclonal immunoglobulins with gamma radiation at an effective rate for a time effective to sterilize said preparation of monoclonal immunoglobulins, wherein steps (i) and (ii) may be performed in inverse order and further wherein the pH of said preparation of monoclonal immunoglobulins is less than 7.

6. A method for sterilizing a preparation of monoclonal immunoglobulins that is sensitive to radiation and has a residual solvent content, said method comprising:

(i) reducing said residual solvent content of a 10 preparation of monoclonal immunoglobulins to a level effective to protect said preparation of monoclonal immunoglobulins from said radiation;

(ii) adding to said preparation of monoclonal immunoglobulins at least one stabilizer in an amount effective to protect said preparation of monoclonal immunoglobulins from said radiation; and (iii) irradiating said preparation of monoclonal immunoglobulins with gamma radiation at a low rate for a time effective to sterilize said preparation of monoclonal immunoglobulins, wherein steps (i) and (ii) may be performed in inverse order and further wherein the pH of said preparation of monoclonal immunoglobulins is less than 7.

7. The method according to claim 1, wherein said solvent is water.

8. The method according to claim 4, wherein said solvent is water.

9. The method according to claim 5, wherein said solvent is water.

10. The method according to claim 6, wherein said solvent is water.

11. The method according to claim 7, wherein said residual water content is reduced by the addition of an organic solvent.

12. The method according to claim 8, wherein said residual water content is reduced by the addition of an organic solvent.

13. The method according to claim 9, wherein said residual water content is reduced by the addition of organic solvent.

14. The method to claim 10, wherein said residual water content is reduced by the addition of an organic solvent.

15. The method according to claim 1, wherein said solvent is an organic solvent.

16. The method according to claim 4, where in said solvent is an organic solvent.

17. The method according to claim 5, wherein said solvent is an organic solvent.

18. The method according to claim 6, wherein said solvent is an organic solvent.

19. The method according to claim 1, wherein said preparation of monoclonal immunoglobulins is suspended in an organic solvent following reduction of said residual solvent content.

20. The method according to claim 4, wherein said preparation of monoclonal immunoglobulins is suspended in an organic solvent following reduction of said residual solvent content.

21. The method according to claim 5, wherein said preparation of monoclonal immunoglobulins is suspended in an organic solvent following reduction of said residual solvent content.

22. The method according to claim 6, wherein said preparation of monoclonal immunoglobulins is suspended in an organic solvent following reduction of said residual solvent content.

23. The method according to claim 7, wherein said preparation of monoclonal immunoglobulins is suspended in an organic solvent following reduction of said residual solvent content.

24. The method according to claim 8, wherein said preparation of monoclonal immunoglobulins is suspended in an organic solvent following reduction of said residual solvent content.

25. The method according to claim 9, wherein said preparation of monoclonal immunoglobulins is suspended in an organic solvent following reduction of said residual solvent content.

26. The method according to claim 10, wherein said preparation of monoclonal immunoglobulins is suspended in an organic solvent following reduction of said residual solvent content.

27. The method according to claim 11, wherein said preparation of monoclonal immunoglobulins is suspended in an organic solvent following reduction of said residual solvent content.

28. The method according to claim 12, wherein said preparation of monoclonal immunoglobulins is suspended in an organic solvent following reduction of said residual solvent content.

29. The method according to claim 13, wherein said preparation of monoclonal immunoglobulins is suspended in an organic solvent following reduction of said residual solvent content.

30. The method according to claim 14, wherein said preparation of monoclonal immunoglobulins is suspended in an organic solvent following reduction of said residual solvent content.

31. The method according to claim 15, wherein said preparation of monoclonal immunoglobulins is suspended in an organic solvent following reduction of said residual solvent content.

32. The method according to claim 16, wherein said preparation of monoclonal immunoglobulins is suspended in an organic solvent following reduction of said residual solvent content.

33. The method according to claim 17, wherein said preparation of monoclonal immunoglobulins is suspended in an organic solvent following reduction of said residual solvent content.

34. The method according to claim 18, wherein said preparation of monoclonal immunoglobulins is suspended in an organic solvent following reduction of said residual solvent content.

35. The method according to any one of claims 1–6, wherein said monoclonal immunoglobulins are selected from the group consisting of: IgG and fragments, derivatives, and metabolites thereof; IgM and fragments, derivatives, and metabolites thereof; IgA and fragments, derivatives, and metabolites thereof; IgD and fragments, derivatives, and metabolites thereof; IgE and fragments, derivatives, and metabolites thereof; and mixtures thereof.

36. The method according to any one of claims 1–6, wherein said monoclonal immunoglobulins are IgG or fragments or derivatives or metabolites thereof.

37. The method according to any one of claims 1–6, wherein said monoclonal immunoglobulins are IgM or fragments or derivatives or metabolites thereof.

38. The method according to any one of claims 1–6, wherein said monoclonal immunoglobulins are IgA or fragments or derivatives or metabolites thereof.

39. The method according to any one of claims 1–6, wherein said monoclonal immunoglobulins are IgD or fragments or derivatives or metabolites thereof.

40. The method according to any one of claims 1–6, wherein said monoclonal immunoglobulins are IgE or fragments or derivatives or metabolites thereof.

41. The method according to any one of claims 1–6, wherein said monoclonal immunoglobulins comprise immunoglobulin fragments selected from the group consisting of $F(ab')_2$, Fab', Fab, Fc, Facb, pFc', and Fd; or metabolites or derivatives thereof.

42. The method according to any one of claims 1–6, wherein said rate is not more than about 3.0 kGy/hour.

43. The method according to any one of claims 1–6, wherein said rate is not more than about 2.0 kGy/hr.

44. The method according to any one of claims 1–6, wherein said rate is not more than about 1.0 kGy/hr.

45. The method according to any one of claims 1–6, wherein said rate is not more than about 0.3 kGy/hr.

46. The method according to any one of claims 1, 2, or 5, wherein said rate is more than about 3.0 kGy/hour.

47. The method according to any one of claims 1, 2, or 5, wherein said rate is at least about 6.0 kGy/hour.

48. The method according to any one of claims 1, 2, or 5, wherein said rate is at least about 18.0 kGy/hour.

49. The method according to any one of claims 1, 2, or 5, wherein said rate is at least about 45 kGy/hour.

50. The method according to any one of claims 1–6, wherein said preparation of monoclonal immunoglobulins is maintained in a low oxygen atmosphere.

51. The method according to any one of claims 1–6, wherein said preparation of monoclonal immunoglobulins is maintained in an argon atmosphere.

52. The method according to any one of claims 1–6, wherein said preparation of immunoglobulins is maintained in a vacuum.

53. The method according to any one of claims 1, 4, 5 or 6, wherein said residual solvent content is reduced by a method selected from the group consisting of lyophilization, drying, concentration, addition of solute, evaporation, chemical extraction, spray-drying, and vitrification.

54. The method according to any one of claims 1, 4, 5 or 6, wherein said residual solvent content is less than about 10%.

55. The method according to any one of claims 1, 4, 5 or 6, wherein said residual solvent content is less than about 5%.

56. The method according to any one of claims 1, 4, 5 or 6, wherein said residual solvent content is less than about 2%.

57. The method according to any one of claims 1, 4, 5 or 6, wherein said residual solvent content is less than about 1%.

58. The method according to any one of claims 1, 4, 5 or 6, wherein said residual solvent content is less than about 0.5%.

59. The method according to any one of claims 1–6, wherein at least one sensitizer is added to said preparation of monoclonal immunoglobulins prior to said step of irradiating said preparation of monoclonal immunoglobulins.

60. The method according to any one of claims 1–6, wherein said preparation of monoclonal immunoglobulins contains at least one prion as a biological contaminant.

61. The method according to any one of claims 1–6, wherein said preparation of monoclonal immunoglobulins contains at least one virus as a biological contaminant.

62. The method according to claim 1 or 4, wherein at least one stabilizer is added to said preparation of monoclonal immunoglobulins prior to said step of irradiating said preparation of monoclonal immunoglobulins.

63. The method according to any one of claims 2, 3, 5 or 6, wherein at least one of said stabilizers is an antioxidant.

64. The method according to any one of claims 2, 3, 5 or 6, wherein at least one of said stabilizers is a free radical scavenger.

65. The method according to any one of claims 2, 3, 5 or 6, wherein at least one of said stabilizers reduces damage due to reactive oxygen species.

66. The method according to any one of claims 2, 3, 5 or 6, wherein at least one of said stabilizers is selected from the group consisting of: ascorbic acid or a salt or ester thereof glutathione; 6-hydroxy-2,5,7,8-tetramethylchroman-2-carboxylic acid; uric acid or a salt or ester thereof methionine; histidine; N-acetyl cysteine; lipoic acid; sodium formaldehyde sulfoxylate; gallic acid or a derivative thereof propyl gallate and mixtures of two or more of said stabilizers.

67. The method according to claim 66, wherein said mixtures of two or more of said stabilizers are selected from the group consisting of: mixtures of ascorbic acid, or a salt or ester thereof, and uric acid, or a salt or ester thereof, mixtures of ascorbic acid, or a salt or ester thereof, and 6-hydroxy-2,5,7,8-tetramethylchroman-2-carboxylic acid; mixtures of ascorbic acid, or a salt or ester thereof, uric acid, or a salt or ester thereof, and 6-hydroxy-2,5,7,8-tetramethylchroman-2-carboxylic acid; and mixtures of uric acid, or a salt or ester thereof; lipoic acid; sodium formaldehyde sulfoxylate; gallic acid or a derivative thereof; propyl gallate and 6-hydroxy-2,5,7,8-tetramethylchroman-2-carboxylic acid.

68. The method according to any one of claims 2, 3, 5, or 6, at least one of said stabilizers comprises the dipeptide glycine-glycine.

69. The method according to any one of claims 2, 3, 5, or 6, wherein at least one of said stabilizers comprises diosmin.

70. The method according to any one of claims 2, 3, 5, or 6, wherein at least one of said stabilizers comprises silymarin.

71. The method according to any one of claims 1–6, wherein said irradiating is conducted at ambient temperature.

72. The method according to any one of claims 1–6, wherein said irradiating is conducted at a temperature below ambient temperature.

73. The method according to any one of claims 1–6, wherein said irradiating is conducted below the freezing point of the monoclonal immunoglobulin.

74. The method according to any one of claims 1–6, wherein said irradiating is conducted below the eutectic point of the monoclonal immunoglobulin.

75. The method according to any one of claims 1–6, wherein the pH of said preparation of monoclonal immunoglobulins is less than 6.

76. The method according to any one of claims 1–6, wherein the pH of said preparation of monoclonal immunoglobulins is less than 5.

77. The method according to any one of claims 1–6, wherein the pH of said preparation of monoclonal immunoglobulins is less than 4.

78. The method according to any one of claims 1–6, wherein the pH of said preparation of monoclonal immunoglobulins is less than 3.

* * * * *